US009555047B2

(12) United States Patent
Bodick et al.

(10) Patent No.: US 9,555,047 B2
(45) Date of Patent: Jan. 31, 2017

(54) CORTICOSTEROIDS FOR THE TREATMENT OF JOINT PAIN

(71) Applicant: Flexion Therapeutics, Inc., Burlington, MA (US)

(72) Inventors: Neil Bodick, Boston, MA (US); Robert C. Blanks, Auburndale, MA (US); Anjali Kumar, Belmont, MA (US); Michael D. Clayman, Gloucester, MA (US); Mark Moran, Orinda, CA (US)

(73) Assignee: FLEXION THERAPEUTICS, INC., Burlington, MA (US)

( * ) Notice: Subject to any disclaimer, the term of this patent is extended or adjusted under 35 U.S.C. 154(b) by 0 days.

(21) Appl. No.: 14/461,883

(22) Filed: Aug. 18, 2014

(65) Prior Publication Data

US 2015/0025050 A1 Jan. 22, 2015

Related U.S. Application Data

(60) Division of application No. 13/422,994, filed on Mar. 16, 2012, now Pat. No. 8,828,440, which is a continuation of application No. 13/198,168, filed on Aug. 4, 2011, now abandoned.

(60) Provisional application No. 61/370,666, filed on Aug. 4, 2010.

(51) Int. Cl.
| | | |
|---|---|---|
| A61K 9/14 | (2006.01) | |
| A61K 9/50 | (2006.01) | |
| A61K 31/56 | (2006.01) | |
| A61K 31/573 | (2006.01) | |
| A61K 9/16 | (2006.01) | |
| A61K 31/58 | (2006.01) | |
| A61K 9/00 | (2006.01) | |
| A61K 47/34 | (2006.01) | |

(52) U.S. Cl.
CPC ............. *A61K 31/58* (2013.01); *A61K 9/0019* (2013.01); *A61K 9/0024* (2013.01); *A61K 9/14* (2013.01); *A61K 9/1641* (2013.01); *A61K 9/1647* (2013.01); *A61K 9/1694* (2013.01); *A61K 31/573* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,293,539 A | 10/1981 | Ludwig et al. | |
| 4,530,840 A * | 7/1985 | Tice | A61K 9/1694 514/179 |
| 6,214,387 B1 * | 4/2001 | Berde | A61K 9/1641 424/426 |
| 7,153,520 B2 | 12/2006 | Seo et al. | |
| 7,261,529 B2 | 8/2007 | Persyn et al. | |
| 7,758,778 B2 | 7/2010 | Persyn et al. | |
| 8,828,440 B2 | 9/2014 | Bodick et al. | |
| 2004/0105821 A1 | 6/2004 | Bernstein et al. | |
| 2004/0224030 A1 | 11/2004 | Shastri | |
| 2005/0031549 A1 | 2/2005 | Quay et al. | |
| 2005/0043706 A1 | 2/2005 | Eaton et al. | |
| 2005/0069591 A1 | 3/2005 | Bernstein et al. | |
| 2007/0053990 A1 | 3/2007 | Persyn et al. | |
| 2007/0264343 A1 | 11/2007 | Bernstein et al. | |
| 2008/0248122 A1 | 10/2008 | Rashba-Step et al. | |
| 2008/0317805 A1 | 12/2008 | McKay et al. | |
| 2009/0035253 A1 | 2/2009 | Wright et al. | |
| 2009/0123546 A1 | 5/2009 | Ashton et al. | |
| 2009/0324678 A1 | 12/2009 | Thorne et al. | |
| 2010/0063179 A1 * | 3/2010 | Atkinson | A61K 9/5031 523/332 |
| 2011/0206773 A1 | 8/2011 | Lavik et al. | |
| 2012/0282298 A1 | 11/2012 | Bodick et al. | |
| 2012/0288534 A1 | 11/2012 | Bodick et al. | |
| 2014/0242170 A1 | 8/2014 | Bodick et al. | |
| 2014/0356437 A1 | 12/2014 | Bodick et al. | |

FOREIGN PATENT DOCUMENTS

| | | |
|---|---|---|
| CN | 1215589 A | 5/1999 |
| EP | 0911025 A1 | 4/1999 |
| JP | 2006-503865 A | 2/2006 |
| WO | WO 95/13799 A1 | 5/1995 |
| WO | WO-9513799 A1 | 5/1995 |
| WO | WO 99/12571 A1 | 3/1999 |
| WO | WO 02/36168 | 5/2002 |

(Continued)

OTHER PUBLICATIONS

Hickey, T, .et al., "Dexamethasone/PLGA microspheres for continuous delivery of an anti-inflammatory drug for implantable medical devices", Biomaterials, 23(7):1649-1656 (2002).

Horisawa, E., et al. "Prolonged anti-inflammatory action of DL-lactide/glycolide copolymer nanospheres containing betamethasone sodium phosphate for an intra-articular delivery system in antigen-induced arthritic rabbit", Pharmaceutical Research, 19(4):403-409 (2002).

Extended European Search Report in corresponding Application No. EP11815323.8, dated Dec. 17, 2013.

Aly, M N S, "Intra-articular drug delivery: A fast growing approach", Recent Patents on Drug Delivery & Formulation, Bentham Science Publishers Ltd., NL 2(3):231-237 (2008).

(Continued)

*Primary Examiner* — Tigabu Kassa
(74) *Attorney, Agent, or Firm* — Cooley LLP; Ivor R. Elrifi

(57) ABSTRACT

Corticosteroid microparticle formulations are provided for use for treating pain, including pain caused by inflammatory diseases such as osteoarthritis or rheumatoid arthritis, and for slowing, arresting or reversing structural damage to tissues caused by an inflammatory disease, for example damage to articular and/or peri-articular tissues caused by osteoarthritis or rheumatoid arthritis. Corticosteroid microparticle formulations are administered locally as a sustained release dosage form (with or without an immediate release component) that results in efficacy accompanied by clinically insignificant or no measurable effect on endogenous cortisol production.

9 Claims, 30 Drawing Sheets

(56) References Cited

FOREIGN PATENT DOCUMENTS

| WO | WO 2007/030545 A2 | 3/2007 |
|---|---|---|
| WO | WO 2008/157057 A2 | 12/2008 |
| WO | WO 2009/026539 | 2/2009 |
| WO | WO 2009/026539 A1 | 2/2009 |
| WO | WO 2009/150136 A1 | 12/2009 |
| WO | WO 2010/085609 | 7/2010 |
| WO | WO 2011/084518 | 7/2011 |
| WO | WO 2012/019009 A1 | 2/2012 |

OTHER PUBLICATIONS

Da Silva-Junior, A A et al., "Thermal behavior and stability of biodegradable spray-dried microparticles containing triamcinolone", International Journal of Pharmaceutics, Elsevier BV, NL, 368(1-2):45-55 (2009).
Cilurzo, F. et al: "Design of Methylprednisolone Biodegradable Microspheres Intended for Intra-articular Administration", AAPS Pharmscitech, val. 9, No. 4, Nov. 14, 2008 (Nov. 14, 2008), pp. 1136-1142.
Khaled K. A. et al., "Prednisolone-Loaded PLGA Microspheres. In Vitro Characterization and In Vivo Application in Adjuvant-Induced Arthritis in Mice," AAPS PharmSciTech., Jun. 19, 2010 (Jun. 19, 2010), pp. 859-869.
Anderson et al. "Biodegradation and Biocompatibility of PLA and PLGA Microspheres." *Adv. Drug Deliv. Rev.* 28(1997):5-24.
Ayral et al. "Synovitis: A Potential Predictive Factor of Structural Progression of Medial Tibiofemoral Knee Osteoarthritis—Results of a 1 Year Longitudinal Arthroscopic Study in 422 Patients." *OsteoArth. Cartilage.* 13(2005):361-367.
Bouissou et al. "Poly(lactic-co-glycolic acid) Microspheres." *Polymers in Drug Delivery.* Chapter 7(2006):81-99.
Cleek et al. "Microparticles of Poly(DL-lactic-co-glycolic acid)/poly(ethylene glycol) Blends for Controlled Drug Delivery." *J. Control. Relase.* 48(1997):259-268.
Coopman et al. "Identification of Cross-Reaction Patterns in Allergic Contact Dermatitis from Topical Corticosteroids." *Br. J. Dermatol.* 121(1989):27-34.
Derendorf et al. "Clinical PK/PD Modelling as a Tool in Drug Development of Corticosteroids." *Int. J. Clin. Pharmacol. Ther.* 35.10(1997):481-488.
Derendorf et al. "Pharmacokinetics and Pharmacodynamics of Glucocorticoid Suspensions After Intra-Articular Administration." *Clin. Pharmacol. Ther.* 39.3(1986):313-317.
Eckstein et al. "Magnetic Resonance Imaging (MRI) of Articular Cartilage in Knee Osteoarthritis (OA): Morphological Assessment." *OsteoArth. Cartilage.* 14(2006):A46-A75.
Foti et al. "Contact Allergy to Topical Corticosteroids: Update and Review on Cross-Sensitization." *Recent Pat. Inflamm. Allergy Drug Discov.* 3.1(2009):33-39.
Habib. "Systemic Effects of Intra-Articular Corticosteroids." *Clin. Rheumatol.* 28.7(2009):749-756.
Hepper et al. "The Efficacy and Duration of Intra-Articular Corticosteroid Injection for Knee Osteoarthritis: A Systematic Review of Level I Studies." *J. Am. Acad. Orthop. Surg.* 17.10(2009):638-646.
Hill et al. "Synovitis Detected on Magnetic Resonance Imaging and its Relation to Pain and Cartilage Loss in Knee Osteoarthritis." *Ann. Rheum. Dis.* 66(2007):1599-1603.
Hou et al. "In Situ Gelling Hydrogels Incorporating Microparticles as Drug Delivery Carriers for Regenerative Medicine." *J. Pharm. Sci.* 97.9(2008):3972-3980.
Kirwan et al. "Effects of Glucocorticoids on Radiological Progression in Rheumatoid Arthritis." *Cochrane Database Syst. Rev.* (2009).
La Rochelle et al. "Recovery of the Hypothalamic-Pituitary-Adrenal (HPA) Axis in Patients with Rheumatic Diseases Receiving Low-Dose Prednisone." *Am. J. Med.* 95(1993):258-264.
Lo et al. "Bone Marrow Lesions in the Knee are Associated with Increased Local Bone Density." *Arth. Rheum.* 52.9(2005):2814-2821.
Lo et al. "The Ratio of Medial to Lateral Tibial Plateau Bone Mineral Density and Compartment-Specific Tibiofemoral Osteoarthritis." *OsteoArth. Cartilage.* 14(2006):984-990.
Meibohm et al. "Mechanism-Based PK/PD Model for the Lymphocytopenia Induced by Endogenous and Exogenous Corticosteroids." *Int. J. Clin. Pharmacol. Ther.* 37.8(1999):367-376.
Morlock et al. "Erythropoietin Loaded Microspheres Prepared from Biodegradable LPLG-PEO-LPLG Triblock Copolymers: Protein Stabilization and in-vitro Release Properties." *J. Control. Release.* 56.1-3(1998):105-115.
Rojas et al. "Microdialysis of Triamcinolone Acetonide in Rat Muscle." *J. Pharm. Sci.* 92.2(2003):394-397.
van den Berg et al. "Synovial Mediators of Cartilage Damage and Repair in Osteoarthritis." *Osteoarthritis.* Brandt et al., eds. Oxford: Oxford University Press. 7.2.3 (2003):147-155.
Yeh. "The Stability of Insulin in Biodegradable Microparticles Based on Blends of Lactide Polymers and Polyethylene Glycol." *J. Microencapsul.* 17.6(2000):743-756.
Zentner et al. "Biodegradable Block Copolymers for Delivery of Proteins and Water-Insoluble Drugs." *J. Control. Release.* 72(2001):203-215.
Aly, M. N. S., "Intra-Articular Drug Delivery: A Fast Growing Approach," *Recent Patents on Drug Delivery & Formulation*, vol. 2(3):231-237 (2008).
Bandi, N. et al., "Intratracheal budesonide-poly(lactide-co-glycolide) microparticles reduce oxidative stress, VEGF expression, and vascular leakage in a benzo(a)pyrene-fed mouse model," *Journal of Pharmacy and Pharmacology*, vol. 57(7):851-860 (2005).
Chaw, C.S. et al., "Water soluble betamethasone-loaded poly(lactide-co-glycolide) hollow microparticles as a sustained release dosage form," *Journal of Encapsulation*, vol. 20(3):349-359 (2003).
Cilurzo, F. et al., "Design of methylprednisolone biodegradable microspheres intended for intra-articular administration," *AAPS Pharmscitech*, vol. 9(4):136-1142 (2008).
Da Silva-Junior, A. A. et al., "Thermal behavior and stability of biodegradable spray-dried microparticles containing triamcinolone," *International Journal of Pharmaceutics*, vol. 368(1-2):45-55 (2009).
Hickey, T. et al., "Dexamethasone/PLGA microspheres for continuous delivery of an anti-inflammatory drug for implantable medical devices," *Biomaterials*, vol. 23(7):1649-1656 (2002).
Horisawa, E., et al., "Prolonged anti-inflammatory action of DL-lactide/glycolide copolymer nanospheres containing betamethasone sodium phosphate for an intra-articular delivery system in antigen-induced arthritic rabbit," *Pharmaceutical Research*, vol. 19(4):403-409 (2002).
Jaraswekin, S. et al., "Effect of poly(lactide-co-glycolide) molecular weight on the release of dexamethasone sodium phosphate from microparticles," *Journal of Microencapsulation*, vol. 24(2):117-128 (2007).
Khaled, K. A. et al., "Prednisolone-loaded PLGA microspheres. In vitro characterization and in vivo application in adjuvant-induced arthritis in mice," *AAPS PharmSciTech*, vol. 111(2):859-869 (2010).
Yeo and Park, "Control of Encapsulation Efficiency and Initial Burst in Polymeric Microparticle Systems." Arch Pharm Res, vol. 27(1):1-12 (2004).

* cited by examiner

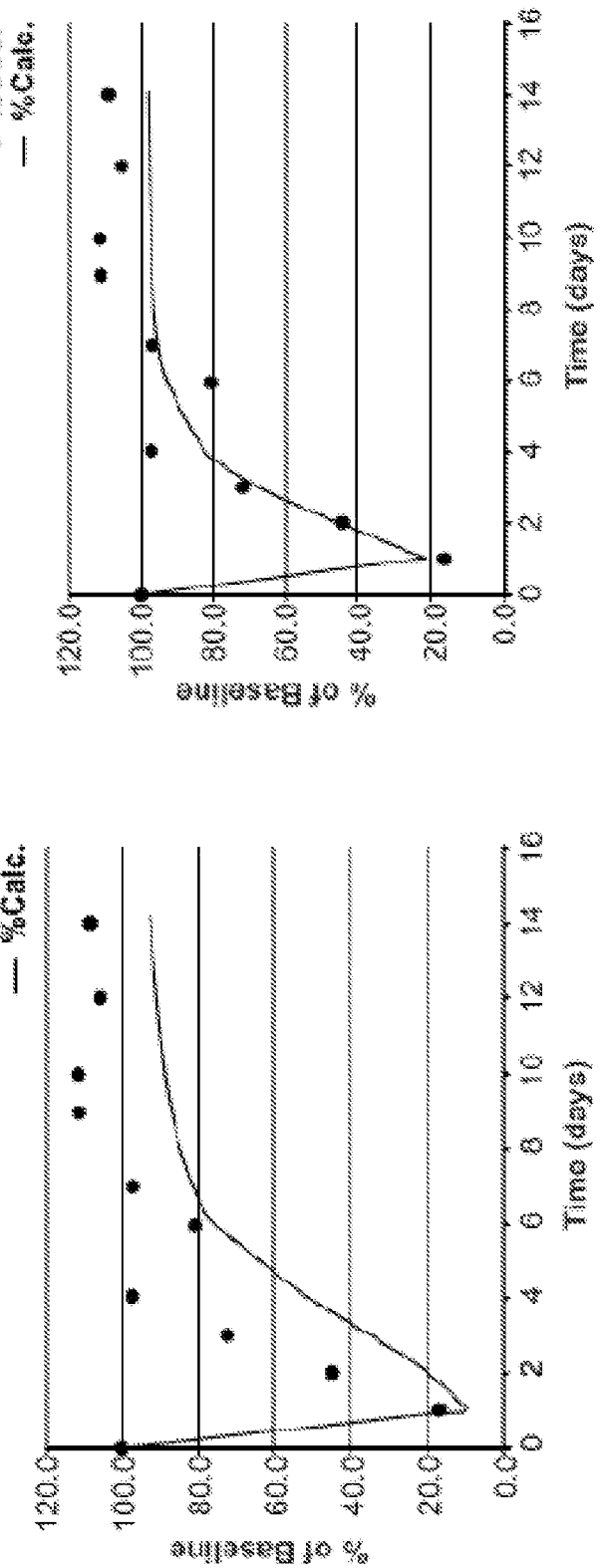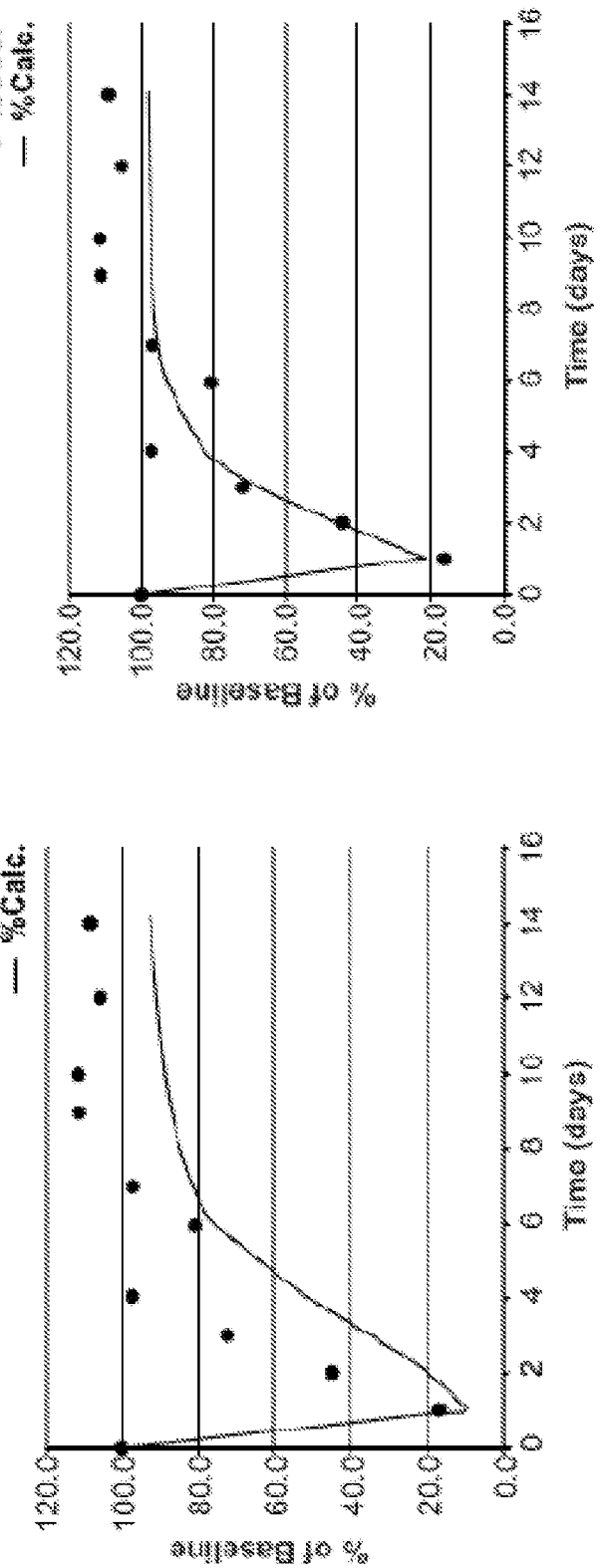
FIG. 4A — Observed vs. Predicted Without Correction for a Change in Sensitivity of the HPA Axis
FIG. 4B — Observed vs. Predicted With Correction for a Change in Sensitivity of the HPA Axis Peak pain response upon reactivation of knee arthritis

CORTICOSTEROIDS FOR THE TREATMENT OF JOINT PAIN

RELATED APPLICATIONS

This application is a divisional of U.S. patent application Ser. No. 13/422,994, now issued as U.S. Pat. No. 8,828,440, which is a continuation of U.S. patent application Ser. No. 13/198,168, filed Aug. 4, 2011, which claims the benefit of U.S. Provisional Application No. 61/370,666, filed Aug. 4, 2010. The contents of these applications are hereby incorporated by reference in their entireties.

FIELD OF THE INVENTION

This invention relates to the use of corticosteroids to treat pain, including pain caused by inflammatory diseases such as osteoarthritis or rheumatoid arthritis, and to slow, arrest or reverse structural damage to tissues caused by an inflammatory disease, for example damage to articular and/or peri-articular tissues caused by osteoarthritis or rheumatoid arthritis. More specifically, a corticosteroid is administered locally as a sustained release dosage form (with or without an immediate release component) that results in efficacy accompanied by clinically insignificant or no measurable effect on endogenous cortisol production.

BACKGROUND OF THE INVENTION

Corticosteroids influence all tissues of the body and produce various cellular effects. These steroids regulate carbohydrate, lipid, protein biosynthesis and metabolism, and water and electrolyte balance. Corticosteroids influencing cellular biosynthesis or metabolism are referred to as glucocorticoids while those affecting water and electrolyte balance are mineralocorticoids. Both glucocorticoids and mineralocorticoids are released from the cortex of the adrenal gland.

The administration of corticosteroids, particularly for extended periods of time, can have a number of unwanted side effects. The interdependent feedback mechanism between the hypothalamus, which is responsible for secretion of corticotrophin-releasing factor, the pituitary gland, which is responsible for secretion of adrenocorticotropic hormone, and the adrenal cortex, which secretes cortisol, is termed the hypothalamic-pituitary-adrenal (HPA) axis. The HPA axis may be suppressed by the administration of corticosteroids, leading to a variety of unwanted side effects.

Accordingly, there is a medical need to extend the local duration of action of corticosteroids, while reducing the systemic side effects associated with that administration. Thus, there is a need in the art for methods and compositions for the sustained local treatment of pain and inflammation, such as joint pain, with corticosteroids that results in clinically insignificant or no measurable HPA axis suppression. In addition, there is a medical need to slow, arrest, reverse or otherwise inhibit structural damage to tissues caused by inflammatory diseases such as damage to articular tissues resulting from osteoarthritis or rheumatoid arthritis.

SUMMARY OF THE INVENTION

Described herein are compositions and methods for the treatment of pain and inflammation using corticosteroids. The compositions and methods provided herein use one or more corticosteroids in a microparticle formulation. The corticosteroid microparticle formulations provided herein are effective at treating pain and/or inflammation with minimal long-term side effects of corticosteroid administration, including for example, prolonged suppression of the HPA axis. The corticosteroid microparticle formulations are suitable for administration, for example, local administration by injection into a site at or near the site of a patient's pain and/or inflammation. The corticosteroid microparticle formulations provided herein are effective in slowing, arresting, reversing or otherwise inhibiting structural damage to tissues associated with progressive disease with minimal long-term side effects of corticosteroid administration, including for example, prolonged suppression of the HPA axis. The corticosteroid microparticle formulations are suitable for administration, for example, local administration by injection into a site at or near the site of structural tissue damage. As used herein, "prolonged" suppression of the HPA axis refers to levels of cortisol suppression greater than 35% by day 14 post-administration, for example post-injection. The corticosteroid microparticle formulations provided herein deliver the corticosteroid in a dose and in a controlled or sustained release manner such that the levels of cortisol suppression are at or below 35% by day 14 post-administration, for example post-injection. In some embodiments, the corticosteroid microparticle formulations provided herein deliver the corticosteroid in a dose and in a controlled or sustained release manner such that the levels of cortisol suppression are negligible and/or undetectable by 14 post-administration, for example post-injection. In some embodiments, the corticosteroid microparticle formulations provided herein deliver the corticosteroid in a dose and in a controlled or sustained release manner such that the levels of cortisol suppression are negligible at any time post-injection. Thus, the corticosteroid microparticle formulations in these embodiments are effective in the absence of any significant HPA axis suppression. Administration of the corticosteroid microparticle formulations provided herein can result in an initial "burst" of HPA axis suppression, for example, within the first few days, within the first two days and/or within the first 24 hours post-injection, but by day 14 post-injection, suppression of the HPA axis is less than 35%.

In certain embodiments, a sustained release form of corticosteroids is administered locally to treat pain and inflammation. Local administration of a corticosteroid microparticle formulation can occur, for example, by injection into the intra-articular space, peri-articular space, soft tissues, lesions, epidural space, perineural space, or the foramenal space at or near the site of a patient's pain. In certain embodiments, the formulation additionally contains an immediate release component. In certain preferred embodiments of the invention, a sustained release form of corticosteroids is administered (e.g., by single injection or as sequential injections) into an intra-articular space for the treatment of pain, for example, due to osteoarthritis, rheumatoid arthritis, gouty arthritis, bursitis, tenosynovitis, epicondylitis, synovitis or other joint disorder. In certain preferred embodiments of the invention, a sustained release form of corticosteroids is administered (e.g., by single injection or as sequential injections) into soft tissues or lesions for the treatment of inflammatory disorders, for example, the inflammatory and pruritic manifestations of corticosteroid-responsive dermatoses such as psoriasis. In certain preferred embodiments of the invention, a sustained release form of corticosteroids is administered (e.g., by single injection or as sequential injections) into an epidural space, a perineural space, a foramenal space or other spinal space for the treatment of corticosteroid-responsive degenerative musculoskeletal disorders such as Neurogenic Claudication. In certain preferred embodiments of the invention, a sustained release form of corticosteroids is administered (e.g., by single injection or as sequential injections) into an intra-articular space or into soft tissues to slow, arrest, reverse or otherwise inhibit structural damage to tissues associated with progressive disease such as, for example, the damage to cartilage associated with progression of osteoarthritis.

In certain embodiments of the invention, a combination of an immediate release form and a sustained release form of corticosteroids is administered (e.g., by single injection or as sequential injections) into an intra-articular space for the treatment of pain, for example, due to osteoarthritis, rheumatoid arthritis or other joint disorder(s). In certain embodiments of the invention, a combination of an immediate release form and a sustained release form of corticosteroids is administered (e.g., by single injection or as sequential injections) into an intra-articular space or into soft tissues to slow, arrest, reverse or otherwise inhibit structural damage to tissues associated with progressive disease such as, for example, the damage to cartilage associated with progression of osteoarthritis. The formulations and methods of embodiments of the invention can achieve immediate relief of the acute symptoms (e.g., pain and inflammation) of these diseases or conditions and additionally provide a sustained or long term therapy (e.g., slowing, arresting, reversing or otherwise inhibiting structural damage to tissues associated with progressive disease), while avoiding long term systemic side effects associated with corticosteroid administration, including HPA suppression.

In one aspect, a formulation is provided wherein a microparticle matrix (such as PLGA, PLA, hydrogels, hyaluronic acid, etc.) incorporates a corticosteroid, and the corticosteroid microparticle formulation provides at least two weeks, preferably at least three weeks, including up to and beyond 30 days, or 60 days, or 90 days of a sustained, steady state release of the corticosteroid. In one aspect, a formulation is provided wherein a microparticle matrix (such as PLGA, PLA, hydrogels, hyaluronic acid, etc.) incorporates a corticosteroid, and the corticosteroid microparticle formulation provides at least two weeks, preferably at least three weeks, including up to and beyond 30 days, or 60 days, or 90 days of a sustained, steady state release of the corticosteroid at a rate that does not adversely suppress the HPA axis.

The corticosteroid microparticle formulation retains sustained efficacy even after the corticosteroid is no longer resident at the site of administration, for example, in the intra-articular space, and/or after the corticosteroid is no longer detected in the systemic circulation. The corticosteroid microparticle formulation retains sustained efficacy even after the corticosteroid microparticle formulation is no longer resident at the site of administration, for example, in the intra-articular space, and/or the corticosteroid microparticle formulation is no longer detected in the systemic circulation. The corticosteroid microparticle formulation retains sustained efficacy even after the corticosteroid microparticle formulation ceases to release therapeutically effective amounts of corticosteroid. For example, in some embodiments, the corticosteroid released by the microparticle formulation retains efficacy for at least one week, at least two weeks, at least three weeks, at least four weeks, at least five weeks, at least six weeks, at least seven weeks, at least eight weeks, at least nine weeks, at least twelve weeks, or more than twelve-weeks post-administration. In some embodiments, the corticosteroid released by the microparticle formulation retains efficacy for a time period that is at least twice as long, at least three times as long, or more than three times as long as the residency period for the corticosteroid and/or the corticosteroid microparticle formulation. In some embodiments, the sustained, steady state release of corticosteroid will not adversely suppress the HPA axis.

In some embodiments, a controlled or sustained-release formulation is provided wherein a microparticle matrix (such as PLGA, hydrogels, hyaluronic acid, etc.) incorporates a corticosteroid, and the formulation may or may not exhibit an initial rapid release, also referred to herein as an initial "burst" of the corticosteroid for a first length of time of between 0 and 14 days, for example, between the beginning of day 1 through the end of day 14, in addition to the sustained, steady state release of the corticosteroid for a second length of time of at least two weeks, preferably at least three weeks, including up to and beyond 30 days, or 60 days, or 90 days. It should be noted that when corticosteroid levels are measured in vitro, an occasional initial burst of corticosteroid release from the microparticle formulation can be seen, but this initial burst may or may not be seen in vivo. In another embodiment, a controlled or sustained-release formulation is provided wherein a microparticle matrix (such as PLGA, hydrogels, hyaluronic acid, etc.) incorporates a corticosteroid, and the formulation may or may not exhibit an initial rapid release, also referred to herein as an initial "burst" of the corticosteroid for a first length of time of between 0 and 14 days, e.g., between the beginning of day 1 through the end of day 14, in addition to the sustained, steady state release of the corticosteroid for a second length of time of at least two weeks, preferably at least three weeks, including up to and beyond 30 days, or 60 days, or 90 days where the sustained, steady state release of corticosteroid is released at a rate that does not suppress the HPA axis at a level greater than 50% at day 14 post-administration. In some embodiments, the sustained, steady state release of corticosteroid will not adversely suppress the HPA axis, for example, the level of HPA axis suppression at or less than 35% by day 14 post-administration. In some embodiments, the sustained, steady state release of corticosteroid does not significantly suppress the HPA axis, for example, the level of HPA axis suppression is negligible and/or undetectable by day 14 post-injection. In some embodiments, the sustained, steady state release of corticosteroid does not significantly suppress the HPA axis, for example, the level of HPA axis suppression is negligible at all times post-injection. In some embodiments, the length of sustained release is between 21 days and 90 days. In some embodiments, the length of sustained release is between 21 days and 60 days. In some embodiments, the length of sustained release is between 14 days and 30 days. In some embodiments, the length of release of the initial "burst" component is between 0 and 10 days, for example between the beginning of day 1 through the end of day 10. In some embodiments, the length of release of the initial "burst" component is between 0 and 6 days, for example between the beginning of day 1 through the end of day 6. In some embodiments, the length of initial "burst," component is between 0 and 2 days, for example between the beginning of day 1 through the end of day 2. In some embodiments, the length of initial "burst" component is between 0 and 1 day, for example between the beginning of day 1 through the end of day 1.

The corticosteroid microparticle formulations provided herein can be used in combination with any of a variety of therapeutics, also referred to herein as "co-therapies." For example, the corticosteroid microparticle formulations can be used in combination with an immediate release corticosteroid solution or suspension, which provides high local exposures for between 1 day and 14 days following administration and which produce systemic exposures that may be associated with transient suppression of the HPA axis. For example, 40 mg of immediate release triamcinolone acetonide co-administered with the corticosteroid microparticle formulation in the intra-articular space would be expected to produce high local concentrations lasting for about 12 days. These high local concentrations would be associated with peak plasma concentration of triamcinolone acetonide of approximately 10 ng/ml on day 1, and over the course of the first 12 days of release of the triamcinolone acetonide from the intra-articular space would be associated with transient suppression of the HPA axis with a maximal effect of approximately 60% suppression of cortisol on day 1-2 (Derendorf et al., "Pharmacokinetics and pharmacodynamics of glucocorticoid suspensions after intra-articular administration." *Clin Pharmacol Ther.* 39 (3) (1986):313-7). By day 12, the contribution of the immediate release component to the plasma concentration would be small, less than 0.1 ng/ml, and the contribution to the intra articular concentration of the immediate release component would also be small. However at day 12 and beyond, the corticosteroid microparticle formulation would continue to release corticosteroid in the intra articular space at a rate that extends the duration of therapeutic effect and does not suppress the HPA axis. In some embodiments, the same corticosteroid is used in both the immediate release and sustained release components. In some embodiments, the immediate release component contains a corticosteroid that is different from that of the sustained release component. In some embodiments, the sustained, steady state release of corticosteroid will not adversely suppress the HPA axis. In some embodiments, the period of sustained release is between 21 days and 90 days. In some embodiments, the period of sustained release is between 21 days and 60 days. In some embodiments, the period of sustained release is between 14 days and 30 days. In some embodiments, the high local exposure attributable to the immediate release component lasts for between 1 day and 14 days. In some embodiments, the high local exposure attributable to the immediate release component lasts for between 1 day and 10 days. In some embodiments, the high local exposure attributable to the immediate release component lasts between 1 days and 8 days. In some embodiments, the high local exposure attributable to the immediate release component lasts between 1 days and 6 days. In some embodiments, the high local exposure attributable to the immediate release component lasts for between 1 day and 4 days.

Upon administration, the corticosteroid microparticle formulation may provide an initial release of corticosteroid at the site of administration, for example, in the intra-articular space and/or peri-articular space. Once the initial release of corticosteroid has subsided, the controlled or sustained release of the corticosteroid microparticle formulations continues to provide therapeutic (e.g., intra-articular and/or peri-articular) concentrations of corticosteroid to suppress inflammation, maintain analgesia, and/or slow, arrest or reverse structural damage to tissues for an additional period of therapy following administration (FIG. 1, top tracings). However, the systemic exposure associated with the sustained release component does not suppress the HPA axis (FIG. 1, bottom tracings). Thus, the invention includes therapies and formulations that may exhibit an initial release of corticosteroid followed by controlled or sustained release where the therapy comprises a period of therapy wherein the corticosteroid is released from the sustained release component and the plasma levels of the corticosteroid does not adversely suppress the HPA axis.

In some embodiments, the length of sustained release is between 21 days and 90 days. In some embodiments, the length of sustained release is between 21 days and 60 days. In some embodiments, the length of sustained release is between 14 days and 30 days. In some embodiments, the length of release of the immediate release form is between 1 day and 14 days. In some embodiments, the length of release of the immediate release form is between 1 day and 10 days. In some embodiments, the length of release of the immediate release form is between 1 day and 8 days. In some embodiments, the length of release of the immediate release form is between 1 day and 6 days. In some embodiments, the length of release of the immediate release form is between 1 day and 4 days.

The invention provides populations of microparticles including a Class B corticosteroid or a pharmaceutically acceptable salt thereof incorporated in, admixed, encapsulated or otherwise associated with a lactic acid-glycolic acid copolymer matrix, wherein the Class B corticosteroid is between 22% to 28% of the microparticles.

The invention also provides controlled or sustained release preparation of a Class B corticosteroid that include a lactic acid-glycolic acid copolymer microparticle containing the Class B corticosteroid, wherein the Class B corticosteroid is between 22% to 28% of the lactic acid-glycolic acid copolymer microparticle matrix.

The invention also provides formulations that include (a) controlled- or sustained-release microparticles comprising a Class B corticosteroid and a lactic acid-glycolic acid copolymer matrix, wherein the Class B corticosteroid comprises between 22% to 28% of the microparticles and wherein the lactic acid-glycolic acid copolymer has one of more of the following characteristics: (i) a molecular weight in the range of about 40 to 70 kDa; (ii) an inherent viscosity in the range of 0.3 to 0.5 dL/g; (iii) a lactide:glycolide molar ratio of 80:20 to 60:40; and/or (iv) the lactic acid-glycolic acid copolymer is carboxylic acid endcapped.

In some embodiments of these populations, preparations and/or formulations, the copolymer is biodegradable. In some embodiments, the lactic acid-glycolic acid copolymer is a poly(lactic-co-glycolic) acid copolymer (PLGA). In some embodiments, the lactic acid-glycolic acid copolymer has a molar ratio of lactic acid:glycolic acid from the range of about 80:20 to 60:40. In some embodiments, the lactic acid-glycolic acid copolymer has a molar ratio of lactic acid:glycolic acid of 75:25.

The invention also provides populations of microparticles including a Class B corticosteroid or a pharmaceutically acceptable salt thereof incorporated in, admixed, encapsulated or otherwise associated with a mixed molecular weight lactic acid-glycolic acid copolymer matrix, wherein the Class B corticosteroid is between 12% to 28% of the microparticles. In some embodiments, the corticosteroid microparticle formulation includes a Class B corticosteroid and a microparticle made using 75:25 PLGA formulation with two PLGA polymers, one of low molecular weight and one of high molecular weight in a two to one ratio, respectively. The low molecular weight PLGA has a molecular weight of range of 15-35 kDa and an inherent viscosity range from 0.2 to 0.35 dL/g and the high molecular weight PLGA has a range of 70-95 kDa and an inherent viscosity range of 0.5 to 0.70 dL/g. In these TCA/75:25 PLGA corticosteroid microparticle formulations, the microparticles have a mean diameter in the range of 10-100 μM. In some embodiments, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

The invention also provides populations of microparticles including a Class B corticosteroid or a pharmaceutically acceptable salt thereof incorporated in, admixed, encapsulated or otherwise associated with a lactic acid-glycolic acid copolymer matrix containing 10-20% triblock (PEG-PLGA-PEG) having an inherent viscosity in the range from 0.6 to 0.8 dL/g, wherein the Class B corticosteroid is between 22% to 28% of the microparticles. In some embodiments, the corticosteroid microparticle formulation includes a Class B corticosteroid and a microparticle made using 75:25 PLGA formulation and containing 10-20% triblock (PEG-PLGA-PEG) having an inherent viscosity in the range from 0.6 to 0.8 dL/g. In these TCA/75:25 PLGA corticosteroid microparticle formulations, the microparticles have a mean diameter in the range of 10-100 μM. In some embodiments, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

These Class B corticosteroid microparticle formulations, preparations, and populations thereof, when administered to a patient, exhibit reduced undesirable side effects in patient, for example, undesirable effects on a patient's cartilage or other structural tissue, as compared to the administration, for example administration into the intra-articular space of a joint, of an equivalent amount of the Class B corticosteroid absent any microparticle or other type of incorporation, admixture, or encapsulation.

In some embodiments, the Class B corticosteroid is triamcinolone acetonide or a commercially available chemical analogue or a pharmaceutically-acceptable salt thereof. In some embodiments, the total dose of corticosteroid contained in the microparticles is in the range of 10-90 mg, where the Class B corticosteroid is between 12-28% of the microparticle, for example, between 22-28% of the microparticle (i.e., when the corticosteroid is 28% of the microparticle, the microparticle is in the range of 35.7-321.4 mgs, and so on for all values between 22-28% load dose, when the corticosteroid is 25% of the microparticle, the microparticle is in the range of 40-360 mgs, when the corticosteroid is 22% of the microparticle, the microparticle is in the range of 45.5-409.1 mgs, when the corticosteroid is 12% of the microparticle, the microparticle is in the range of 83.3-750 mgs, and so on for all values between 12-28% load dose). In some embodiments, the Class B corticosteroid contained in the microparticles is 12-28% of the microparticle, for example, between 22-28% of the microparticle and the total dose of corticosteroid is in a range selected from 10-80 mg, 10-70 mg, 10-60 mg, 10-50 mg, 10-40 mg, 10-30 mg, 10-20 mg, 20-90 mg, 20-80 mg, 20-70 mg, 20-60 mg, 20-50 mg, 20-40 mg, 20-30 mg, 30-90 mg, 30-80 mg, 30-70 mg, 30-60 mg, 30-50 mg, 30-40 mg, 40-90 mg, 40-80 mg, 40-70 mg, 40-60 mg, 40-50 mg, 50-90 mg, 50-80 mg, 50-70 mg, 50-60 mg, 60-90 mg, 60-80 mg, 60-70 mg, 70-90 mg, 70-80 mg, and 80-90 mg. In some embodiments, the Class B corticosteroid is released for between 14 days and 90 days.

In some embodiments, the microparticles have a mean diameter of between 10 μm to 100 μm, for example, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

In some embodiments, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

In one embodiment of these populations, preparations and/or formulations, the corticosteroid microparticle formulation includes triamcinolone acetonide (TCA) and a microparticle made using 75:25 PLGA formulation having an inherent viscosity in the range from 0.3 to 0.5 dL/g and/or a molecular weight in the range of 40-70 kDa, for example between 50-60 kDa. In these TCA/75:25 PLGA corticosteroid microparticle formulations, the microparticles have a mean diameter in the range of 10-100 μM. In some embodiments, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

For the TCA/75:25 PLGA microparticle formulations, the range of TCA load percentage is between 22-28%. In one embodiment, the load percentage of TCA in the microparticles in 25%.

The microparticles in the TCA PLGA microparticle formulations can be formulated using PLGA polymers having a range of molecular weights from 40 to 70 kDa, most preferably from 50 to 60 kDa and range of inherent viscosities from 0.5 to 0.5 dL/g, most preferably from 0.38 to 0.42 dL/g.

For the TCA/75:25 PLGA microparticle formulations, the total dose of corticosteroid contained in the microparticles is in the range of 10-90 mg, where TCA is between 22-28% of the microparticle (i.e., when TCA is 25% of the microparticle, the microparticle is in the range of 40-360 mgs, when TCA is 22% of the microparticle, the microparticle is in the range of 45.5-409.1 mgs, when TCA is 28% of the microparticle, the microparticle is in the range of 35.7-321.4 mgs, and so on for all values between 22-28% load dose). In some embodiments, total dose of corticosteroid contained in the microparticles is in a range selected from 10-80 mg, 10-70 mg, 10-60 mg, 10-50 mg, 10-40 mg, 10-30 mg, 10-20 mg, 20-90 mg, 20-80 mg, 20-70 mg, 20-60 mg, 20-50 mg, 20-40 mg, 20-30 mg, 30-90 mg, 30-80 mg, 30-70 mg, 30-60 mg, 30-50 mg, 30-40 mg, 40-90 mg, 40-80 mg, 40-70 mg, 40-60 mg, 40-50 mg, 50-90 mg, 50-80 mg, 50-70 mg, 50-60 mg, 60-90 mg, 60-80 mg, 60-70 mg, 70-90 mg, 70-80 mg, and 80-90 mg.

In some embodiments of the TCA/75:25 PLGA microparticle formulations, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

In one embodiment of these populations, preparations and/or formulations, the corticosteroid microparticle formulation includes triamcinolone acetonide (TCA) and a microparticle made using 75:25 PLGA formulation and containing 10-20% triblock (PEG-PLGA-PEG) having an inherent viscosity in the range from 0.6 to 0.8 dL/g. In these TCA/75:25 PLGA corticosteroid microparticle formulations, the microparticles have a mean diameter in the range of 10-100 µM. In some embodiments, the microparticles have a mean diameter in the range of 20-100 µM, 20-90 µM, 30-100 µM, 30-90 µM, or 10-90 µM. It is understood that these ranges refer to the mean diameter of all microparticles in a given population. The diameter of any given individual microparticle could be within a standard deviation above or below the mean diameter.

In one embodiment of these populations, preparations and/or formulations, the corticosteroid microparticle formulation includes triamcinolone acetonide (TCA) and a microparticle made using 75:25 PLGA formulation with two PLGA polymers, one of low molecular weight and one of high molecular weight in a two to one ratio, respectively. The low molecular weight PLGA has a molecular weight of range of 15-35 kDa and an inherent viscosity range from 0.2 to 0.35 dL/g and the high molecular weight PLGA has a range of 70-95 kDa and an inherent viscosity range of 0.5 to 0.70 dL/g. In these TCA/75:25 PLGA corticosteroid microparticle formulations, the microparticles have a mean diameter in the range of 10-100 µM. In some embodiments, the microparticles have a mean diameter in the range of 20-100 µM, 20-90 µM, 30-100 µM, 30-90 µM, or 10-90 µM. It is understood that these ranges refer to the mean diameter of all microparticles in a given population. The diameter of any given individual microparticle could be within a standard deviation above or below the mean diameter.

These TCA microparticle formulations, preparations, and populations thereof, when administered to a patient, exhibit reduced undesirable side effects in patient, for example, undesirable effects on a patient's cartilage or other structural tissue, as compared to the administration, for example administration into the intra-articular space of a joint, of an equivalent amount of TCA absent any microparticle or other type of incorporation, admixture, or encapsulation.

In another embodiment, the corticosteroid microparticle formulation includes a Class A, C, or D corticosteroid and a microparticle made using 50:50 PLGA formulation. For example, in some embodiments, the Class A corticosteroid is prednisolone. In some embodiments, the Class C corticosteroid is betamethasone. In some embodiments, the Class D corticosteroid is fluticasone or fluticasone propionate. In these Class A, C, or D corticosteroid microparticle formulations, the microparticles have a mean diameter in the range of 10-100 µM. In some embodiments, the microparticles have a mean diameter in the range of 20-100 µM, 20-90 µM, 30-100 µM, 30-90 µM, or 10-90 µM. It is understood that these ranges refer to the mean diameter of all microparticles in a given population. The diameter of any given individual microparticle could be within a standard deviation above or below the mean diameter.

For the Class A and/or Class C PLGA microparticle formulations, the range of corticosteroid load percentage is between 10-40%, for example, between 15%-30%. For the Class D PLGA microparticle formulations, the range of corticosteroid load percentage is between 8-20%.

The microparticles in the Class A, C or D PLGA microparticle formulations can be formulated using PLGA polymers having a range of inherent viscosities from 0.35 to 0.5 dL/g and approximated molecular weights from 40 kDa to 70 kDa.

These Class A, C or D corticosteroid microparticle formulations, preparations, and populations thereof, when administered to a patient, exhibit reduced undesirable side effects in patient, for example, undesirable effects on a patient's cartilage or other structural tissue, as compared to the administration, for example administration into the intra-articular space of a joint, of an equivalent amount of the Class A, C or D corticosteroid absent any microparticle or other type of incorporation, admixture, or encapsulation.

The invention provides populations of microparticles including a Class A corticosteroid or a pharmaceutically acceptable salt thereof incorporated in, admixed, encapsulated or otherwise associated with a lactic acid-glycolic acid copolymer matrix, wherein the Class A corticosteroid is between 15% to 30% of the microparticles.

The invention also provides controlled or sustained release preparations of a Class A corticosteroid including a lactic acid-glycolic acid copolymer microparticle containing the Class A corticosteroid, wherein the Class A corticosteroid is between 10% to 40%, for example between 15% to 30% of the lactic acid-glycolic acid copolymer microparticle matrix.

The invention provides formulations that include (a) controlled- or sustained-release microparticles including a Class A corticosteroid and a lactic acid-glycolic acid copolymer matrix, wherein the Class A corticosteroid is between 15% to 30% of the microparticles and wherein the lactic acid-glycolic acid copolymer has one of more of the following characteristics: (i) a molecular weight in the range of about 40 to 70 kDa; (ii) an inherent viscosity in the range of 0.35 to 0.5 dL/g; (iii) a lactide:glycolide molar ratio of 60:40 to 45:55; and/or (iv) the lactic acid-glycolic acid copolymer is carboxylic acid endcapped In some embodiments, the copolymer is biodegradable. In some embodiments, the lactic acid-glycolic acid copolymer is a poly(lactic-co-glycolic) acid copolymer (PLGA). In some embodiments, the lactic acid-glycolic acid copolymer has a molar ratio of lactic acid:glycolic acid from the range of about 60:40 to 45:55. In some embodiments, the lactic acid-glycolic acid copolymer has a molar ratio of lactic acid:glycolic acid of 50:50.

In some embodiments, the Class A corticosteroid is prednisolone or a commercially available chemical analogue or a pharmaceutically-acceptable salt thereof. In some embodiments, total dose of the Class A corticosteroid contained in the microparticles is in a range selected from 10-250 mg, where the Class A corticosteroid is between 10-40%, for example, between 15-30% of the microparticle (i.e., when the corticosteroid is 10% of the microparticle, the microparticle is in the range of 100-2500 mgs, when the corticosteroid is 15% of the microparticle, the microparticle is in the range of 66.7-1666.7 mgs, when the corticosteroid is 20% of the microparticle, the microparticle is in the range of 50-1250 mgs, when the corticosteroid is 25% of the microparticle, the microparticle is in the range of 40-1000 mgs, when the corticosteroid is 30% of the microparticle, the microparticle is in the range of 33.3-833.3 mgs, when the corticosteroid is 40% of the microparticle, the microparticle is in the range of 25-625 mgs and so on for all values between 10-40% load dose). For example, in some embodiments, the total dose of corticosteroid is in the range of 10-225 mg, 10-200 mg, 10-175 mg, 10-150 mg, 10-120 mg, 10-100 mg, 10-75 mg, 10-50 mg, 10-25 mg, 20-250 mg, 20-225 mg, 20-200 mg, 20-175 mg, 20-150 mg, 20-125 mg, 20-100 mg, 20-75 mg, 20-50 mg, 30-250 mg, 30-225 mg, 30-200 mg, 30-175 mg, 30-150 mg, 30-120 mg, 30-100 mg, 30-75 mg, 30-50 mg, 40-250 mg, 40-225 mg, 40-200 mg, 40-175 mg, 40-150 mg, 40-120 mg, 40-100 mg, 40-75 mg, 50-250 mg, 50-225 mg, 50-200 mg, 50-175 mg, 50-150 mg, 50-120 mg, 50-100 mg, 50-75 mg, 60-250 mg, 60-225 mg, 60-200 mg, 60-175 mg, 60-150 mg, 60-120 mg, 60-100 mg, 60-75 mg, 70-250 mg, 70-225 mg, 70-200 mg, 70-175 mg, 70-150 mg, 70-120 mg, 70-100 mg, 80-250 mg, 80-225 mg, 80-200 mg, 80-175 mg, 80-150 mg, 80-120 mg, 80-100 mg, 90-250 mg, 90-225 mg, 90-200 mg, 90-175 mg, 90-150 mg, or 90-120 mg. In some embodiments, the Class A corticosteroid is released for between 14 days and 90 days.

In some embodiments, the microparticles have a mean diameter of between 10 μm to 100 μm, for example, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

In some embodiments, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

In one embodiment of these populations, preparations and/or formulations, the corticosteroid microparticle formulation includes prednisolone and a microparticle made using 50:50 PLGA formulation having a molecular weight in the range of 40 kDa to 70 kDa. In these prednisolone/50:50 PLGA corticosteroid microparticle formulations, the microparticles have a mean diameter in the range of 10-100 μM. In some embodiments, the microparticles have a mean diameter in the range of 20-100 μM, 20-90 μM, 30-100 μM, 30-90 μM, or 10-90 μM.

For the prednisolone/50:50 PLGA microparticle formulations, the range of prednisolone load percentage is between 10-40%, for example, between 15-30%.

In some embodiments of the prednisolone/50:50 PLGA microparticle formulations, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

The invention provides populations of microparticles including a Class C corticosteroid or a pharmaceutically acceptable salt thereof incorporated in, admixed, encapsulated or otherwise associated with a lactic acid-glycolic acid copolymer matrix, wherein the Class C corticosteroid is between 10% to 40% of the microparticles, for example between 15% to 30% of the microparticles.

The invention also provides controlled or sustained release preparations of a Class C corticosteroid including a lactic acid-glycolic acid copolymer microparticle containing the Class C corticosteroid, wherein the Class C corticosteroid is between 15% to 30% of the lactic acid-glycolic acid copolymer microparticle matrix.

The invention provides formulations that include (a) controlled- or sustained-release microparticles having a Class C corticosteroid and a lactic acid-glycolic acid copolymer matrix, wherein the Class C corticosteroid is between 15% to 30% of the microparticles and wherein the lactic acid-glycolic acid copolymer has one of more of the following characteristics: (i) a molecular weight in the range of about 40 to 70 kDa; (ii) an inherent viscosity in the range of 0.35 to 0.5 dL/g; (iii) a lactide:glycolide molar ratio of 60:40 to 45:55; and/or (iv) the lactic acid-glycolic acid copolymer is carboxylic acid endcapped.

In one embodiment of these populations, preparations and/or formulations, the copolymer is biodegradable. In some embodiments, the lactic acid-glycolic acid copolymer is a poly(lactic-co-glycolic) acid copolymer (PLGA). In some embodiments, the lactic acid-glycolic acid copolymer has a molar ratio of lactic acid:glycolic acid from the range of about 60:40 to 45:55. In some embodiments, the lactic acid-glycolic acid copolymer has a molar ratio of lactic acid:glycolic acid of 50:50.

In some embodiments, the Class C corticosteroid is betamethasone or a commercially available chemical analogue or a pharmaceutically-acceptable salt thereof. In some embodiments, total dose of the Class C corticosteroid contained in the microparticles is in a range selected from 2-250 mg, where the Class C corticosteroid is between 10-40%, for example, between 15-30% of the microparticle (i.e., when the corticosteroid is 10% of the microparticle, the microparticle is in the range of 20-2500 mgs, when the corticosteroid is 15% of the microparticle, the microparticle is in the range of 13.3-1666.7 mgs, when the corticosteroid is 20% of the microparticle, the microparticle is in the range of 10-1250 mgs, when the corticosteroid is 25% of the microparticle, the microparticle is in the range of 8-1000 mgs, when the corticosteroid is 30% of the microparticle, the microparticle is in the range of 6.67-833.3 mgs, when the corticosteroid is 40% of the microparticle, the microparticle is in the range of 5-625 mgs and so on for all values between 10-40% load dose). For example, in some embodiments, the total dose of corticosteroid is in the range of 2-225 mg, 2-200 mg, 2-175 mg, 2-150 mg, 2-120 mg, 2-100 mg, 2-75 mg, 2-60 mg, 2-55 mg, 2-50 mg, 2-45 mg, 2-40 mg, 2-35 mg, 2-30 mg, 2-25 mg, 2-20 mg, 2-15 mg, 2-10 mg, 4-225 mg, 4-200 mg, 4-175 mg, 4-150 mg, 4-120 mg, 4-100 mg, 4-75 mg, 4-60 mg, 4-55 mg, 4-50 mg, 4-45 mg, 4-40 mg, 4-35 mg, 4-30 mg, 4-25 mg, 4-20 mg, 4-15 mg, 4-10 mg, 5-225 mg, 5-200 mg, 5-175 mg, 5-150 mg, 5-120 mg, 5-100 mg, 5-75 mg, 5-60 mg, 5-55 mg, 5-50 mg, 5-45 mg, 5-40 mg, 5-35 mg, 5-30 mg, 5-25 mg, 5-20 mg, 5-15 mg, 5-10 mg, 6-225 mg, 6-200 mg, 6-175 mg, 6-150 mg, 6-120 mg, 6-100 mg, 6-75 mg, 6-60 mg, 6-55 mg, 6-50 mg, 6-45 mg, 6-40 mg, 6-35 mg, 6-30 mg, 6-25 mg, 6-20 mg, 6-15 mg, 6-10 mg, 8-225 mg, 8-200 mg, 8-175 mg, 8-150 mg, 8-120 mg, 8-100 mg, 8-75 mg, 8-60 mg, 8-55 mg, 8-50 mg, 8-45 mg, 8-40 mg, 8-35 mg, 8-30 mg, 8-25 mg, 8-20 mg, 8-15 mg, 8-10 mg, 10-225 mg, 10-200 mg, 10-175 mg, 10-150 mg, 10-120 mg, 10-100 mg, 10-75 mg, 10-50 mg, 10-25 mg, 20-250 mg, 20-225 mg, 20-200 mg, 20-175 mg, 20-150 mg, 20-125 mg, 20-100 mg, 20-75 mg, 20-50 mg, 30-250 mg, 30-225 mg, 30-200 mg, 30-175 mg, 30-150 mg, 30-120 mg, 30-100 mg, 30-75 mg, 30-50 mg, 40-250 mg, 40-225 mg, 40-200 mg, 40-175 mg, 40-150 mg, 40-120 mg, 40-100 mg, 40-75 mg, 50-250 mg, 50-225 mg, 50-200 mg, 50-175 mg, 50-150 mg, 50-120 mg, 50-100 mg, 50-75 mg, 60-250 mg, 60-225 mg, 60-200 mg, 60-175 mg, 60-150 mg, 60-120 mg, 60-100 mg, 60-75 mg, 70-250 mg, 70-200 mg, 70-175 mg, 70-150 mg, 70-120 mg, 70-100 mg, 80-250 mg, 80-225 mg, 80-200 mg, 80-175 mg, 80-150 mg, 80-120 mg, 80-100 mg, 90-250 mg, 90-225 mg, 90-200 mg, 90-175 mg, 90-150 mg, or 90-120 mg. In some embodiments, the Class C corticosteroid is released for between 14 days and 90 days.

In some embodiments, the microparticles have a mean diameter of between 10 µm to 100 µm, for example, the microparticles have a mean diameter in the range of 20-100 µM, 20-90 µM, 30-100 µM, 30-90 µM, or 10-90 µM. It is understood that these ranges refer to the mean diameter of all microparticles in a given population. The diameter of any given individual microparticle could be within a standard deviation above or below the mean diameter.

In some embodiments, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

In one embodiment of these populations, preparations and/or formulations, the corticosteroid microparticle formulation includes betamethasone and a microparticle made using 50:50 PLGA formulation having a molecular weight in the range of 40 kDa to 70 kDa. In these betamethasone/50:50 PLGA corticosteroid microparticle formulations, the microparticles have a mean diameter in the range of 10-100 µM. In some embodiments, the microparticles have a mean diameter in the range of 20-100 µM, 20-90 µM, 30-100 µM, 30-90 µM, or 10-90 µM. It is understood that these ranges refer to the mean diameter of all microparticles in a given population. The diameter of any given individual microparticle could be within a standard deviation above or below the mean diameter.

For the betamethasone/50:50 PLGA microparticle formulations, the range of prednisolone load percentage is between 10-40%, for example, between 15-30%.

In some embodiments of the betamethasone/50:50 PLGA microparticle formulations, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

The invention provides populations of microparticles including a Class D corticosteroid or a pharmaceutically acceptable salt thereof incorporated in, admixed, encapsulated or otherwise associated with a lactic acid-glycolic acid copolymer matrix, wherein the Class D corticosteroid is between 8% to 20% of the microparticles, for example, between 10% to 20% of the microparticles.

The invention also provides controlled or sustained release preparation of a Class D corticosteroid including a lactic acid-glycolic acid copolymer microparticle containing the Class D corticosteroid, wherein the Class D corticosteroid is between 8% to 20%, for example, between 10% to 20% of the microparticles of the lactic acid-glycolic acid copolymer microparticle matrix.

The invention provides formulations including (a) controlled- or sustained-release microparticles having a Class D corticosteroid and a lactic acid-glycolic acid copolymer matrix, wherein the Class D corticosteroid is between 8% to 20% of the microparticles, for example, between 10% to 20% of the microparticles, and wherein the lactic acid-glycolic acid copolymer has one of more of the following characteristics: (i) a molecular weight in the range of about 40 to 70 kDa; (ii) an inherent viscosity in the range of 0.35 to 0.5 dL/g; (iii) a lactide:glycolide molar ratio of 60:40 to 45:55; and/or (iv) the lactic acid-glycolic acid copolymer is carboxylic acid endcapped.

In one embodiment of these populations, preparations and/or formulations, the copolymer is biodegradable. In some embodiments, the lactic acid-glycolic acid copolymer is a poly(lactic-co-glycolic) acid copolymer (PLGA). In some embodiments, the lactic acid-glycolic acid copolymer has a molar ratio of lactic acid:glycolic acid from the range of about 60:40 to 45:55. In some embodiments, the lactic acid-glycolic acid copolymer has a molar ratio of lactic acid:glycolic acid of 50:50.

In some embodiments, the Class D corticosteroid is fluticasone propionate, fluticasone, or a commercially available chemical analogue or a pharmaceutically-acceptable salt thereof. In some embodiments, total dose of the Class D corticosteroid contained in the microparticles is in a range selected from 1-250 mg, where the Class D corticosteroid is between 8-20% of the microparticle (i.e., when the corticosteroid is 8% of the microparticle, the microparticle is in the range of 12.5-3125 mgs, when the corticosteroid is 10% of the microparticle, the microparticle is in the range of 10-2500 mgs, when the corticosteroid is 15% of the microparticle, the microparticle is in the range of 6.67-1666.7 mgs, when the corticosteroid is 20% of the microparticle, the microparticle is in the range of 5-1250 mgs, and so on for all values between 10-20% load dose). For example, in some embodiments, the total dose of corticosteroid is in the range of 1-225 mg, 1-200 mg, 1-175 mg, 1-150 mg, 1-120 mg, 1-100 mg, 1-75 mg, 1-60 mg, 1-55 mg, 1-50 mg, 1-45 mg, 1-40 mg, 1-35 mg, 1-30 mg, 1-25 mg, 1-20 mg, 1-15 mg, 1-10 mg, 2-225 mg, 2-200 mg, 2-175 mg, 2-150 mg, 2-120 mg, 2-100 mg, 2-75 mg, 2-60 mg, 2-55 mg, 2-50 mg, 2-45 mg, 2-40 mg, 2-35 mg, 2-30 mg, 2-25 mg, 2-20 mg, 2-15 mg, 2-10 mg, 3-225 mg, 3-200 mg, 3-175 mg, 3-150 mg, 3-120 mg, 3-100 mg, 3-75 mg, 3-60 mg, 3-55 mg, 3-50 mg, 3-45 mg, 3-40 mg, 3-35 mg, 3-30 mg, 3-25 mg, 3-20 mg, 3-15 mg, 3-10 mg, 4-225 mg, 4-200 mg, 4-175 mg, 4-150 mg, 4-120 mg, 4-100 mg, 4-75 mg, 4-60 mg, 4-55 mg, 4-50 mg, 4-45 mg, 4-40 mg, 4-35 mg, 4-30 mg, 4-25 mg, 4-20 mg, 4-15 mg, 4-10 mg, 5-225 mg, 5-200 mg, 5-175 mg, 5-150 mg, 5-120 mg, 5-100 mg, 5-75 mg, 5-60 mg, 5-55 mg, 5-50 mg, 5-45 mg, 5-40 mg, 5-35 mg, 5-30 mg, 5-25 mg, 5-20 mg, 5-15 mg, 5-10 mg, 6-225 mg, 6-200 mg, 6-175 mg, 6-150 mg, 6-120 mg, 6-100 mg, 6-75 mg, 6-60 mg, 6-55 mg, 6-50 mg, 6-45 mg, 6-40 mg, 6-35 mg, 6-30 mg, 6-25 mg, 6-20 mg, 6-15 mg, 6-10 mg, 8-225 mg, 8-200 mg, 8-175 mg, 8-150 mg, 8-120 mg, 8-100 mg, 8-75 mg, 8-60 mg, 8-55 mg, 8-50 mg, 8-45 mg, 8-40 mg, 8-35 mg, 8-30 mg, 8-25 mg, 8-20 mg, 8-15 mg, 8-10 mg, 10-225 mg, 10-200 mg, 10-175 mg, 10-150 mg, 10-120 mg, 10-100 mg, 10-75 mg, 10-50 mg, 10-25 mg, 20-250 mg, 20-225 mg, 20-200 mg, 20-175 mg, 20-150 mg, 20-125 mg, 20-100 mg, 20-75 mg, 20-50 mg, 30-250 mg, 30-225 mg, 30-200 mg, 30-175 mg, 30-150 mg, 30-120 mg, 30-100 mg, 30-75 mg, 30-50 mg, 40-250 mg, 40-225 mg, 40-200 mg, 40-175 mg, 40-150 mg, 40-120 mg, 40-100 mg, 40-75 mg, 50-250 mg, 50-225 mg, 50-200 mg, 50-175 mg, 50-150 mg, 50-120 mg, 50-100 mg, 50-75 mg, 60-250 mg, 60-225 mg, 60-200 mg, 60-175 mg, 60-150 mg, 60-120 mg, 60-100 mg, 60-75 mg, 70-250 mg, 70-225 mg, 70-200 mg, 70-175 mg, 70-150 mg, 70-120 mg, 70-100 mg, 80-250 mg, 80-225 mg, 80-200 mg, 80-175 mg, 80-150 mg, 80-120 mg, 80-100 mg, 90-250 mg, 90-225 mg, 90-200 mg, 90-175 mg, 90-150 mg, or 90-120 mg. In some embodiments, the Class D corticosteroid is released for between 14 days and 90 days.

In some embodiments, the microparticles have a mean diameter of between 10 μm to 100 μm, for example, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

In some embodiments, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

In one embodiment of these populations, preparations and/or formulations, the corticosteroid microparticle formulation includes fluticasone propionate or fluticasone, and a microparticle made using 50:50 PLGA formulation having a molecular weight in the range of 40 kDa to 70 kDa. In these fluticasone or fluticasone propionate/50:50 PLGA corticosteroid microparticle formulations, the microparticles have a mean diameter in the range of 10-100 μM. In some embodiments, the microparticles have a mean diameter in the range of 20-100 μM, 20-90 μM, 30-100 μM, 30-90 μM, or 10-90 μM. It is understood that these ranges refer to the mean diameter of all microparticles in a given population. The diameter of any given individual microparticle could be within a standard deviation above or below the mean diameter.

For the fluticasone or fluticasone propionate/50:50 PLGA microparticle formulations, the range of prednisolone load percentage is between 10-20%.

In some embodiments of the fluticasone or fluticasone propionate/50:50 PLGA microparticle formulations, the microparticles further comprise a polyethylene glycol (PEG) moiety, wherein the PEG moiety comprises between 25% to 0% weight percent of the microparticle. In some embodiments of the microparticles that include a PEG moiety, the populations, preparations and/or formulations of the invention do not require the presence of PEG to exhibit the desired corticosteroid sustained release kinetics and bioavailability profile.

These embodiments of corticosteroid microparticle formulations have been selected because the combination of class of corticosteroid, type of microparticle, molecular weight of polymers used to create the microparticles lactide: glycolide molar ratio, and/or load percentage of the corticosteroid exhibit the desired release kinetics. These embodiments also exhibit the desired release kinetics with minimal prolonged HPA axis suppression.

The invention provides methods of treating pain or inflammation in a patient comprising administering to said patient a therapeutically effective amount of a population of microparticles selected from the following populations: (i) a population of microparticles comprising a Class B corticosteroid or a pharmaceutically acceptable salt thereof incorporated in a lactic acid-glycolic acid copolymer matrix, wherein the Class B corticosteroid comprises between 22% to 28% of the microparticles; (ii) a population of microparticles comprising a Class A corticosteroid or a pharmaceutically acceptable salt thereof incorporated in a lactic acid-glycolic acid copolymer matrix, wherein the Class A corticosteroid comprises between 15% to 30% of the microparticles; (iii) a population of microparticles comprising a Class C corticosteroid or a pharmaceutically acceptable salt thereof incorporated in a lactic acid-glycolic acid copolymer matrix, wherein the Class C corticosteroid comprises between 15% to 30% of the microparticles; and (iv) a population of microparticles comprising a Class D corticosteroid or a pharmaceutically acceptable salt thereof incorporated in a lactic acid-glycolic acid copolymer matrix, wherein the Class D corticosteroid comprises between 8% to 20% of the microparticles. In some embodiments, the population of microparticles releases the corticosteroid for at least 14 days at a rate that does not adversely suppress the hypothalamic-pituitary-adrenal axis (HPA axis). In some embodiments, the population of microparticles releases the corticosteroid in a controlled or sustained release manner such that the levels of cortisol suppression are at or below 35% by day 14 post-administration, for example post-administration. In some embodiments, the population of microparticles releases the corticosteroid in a controlled or sustained release manner such that the levels of cortisol suppression are negligible and/or undetectable by 14 post-administration. In some embodiments, the population of microparticles releases the corticosteroid in a controlled or sustained release manner such that the levels of cortisol suppression are negligible at any time post-administration.

The invention provides methods of treating pain or inflammation in a patient comprising administering to said patient a therapeutically effective amount of a controlled or sustained release preparation selected from the following preparations: (i) a controlled or sustained release preparation of a Class B corticosteroid comprising a lactic acid-glycolic acid copolymer microparticle containing the Class B corticosteroid, wherein the Class B corticosteroid comprises between 22% to 28% of the lactic acid-glycolic acid copolymer microparticle matrix; (ii) a controlled or sustained release preparation of a Class A corticosteroid comprising a lactic acid-glycolic acid copolymer microparticle containing the Class A corticosteroid, wherein the Class A corticosteroid comprises between 15% to 30% of the lactic acid-glycolic acid copolymer microparticle matrix; (iii) a controlled or sustained release preparation of a Class C corticosteroid comprising a lactic acid-glycolic acid copolymer microparticle containing the Class C corticosteroid, wherein the Class C corticosteroid comprises between 15% to 30% of the lactic acid-glycolic acid copolymer microparticle matrix; and (iv) a controlled or sustained release preparation of a Class D corticosteroid comprising a lactic acid-glycolic acid copolymer microparticle containing the Class D corticosteroid, wherein the Class D corticosteroid comprises between 8% to 20% of the lactic acid-glycolic acid copolymer microparticle matrix. In some embodiments, the controlled or sustained release preparation releases the corticosteroid for at least 14 days at a rate that does not adversely suppress the hypothalamic-pituitary-adrenal axis (HPA axis). In some embodiments, the controlled or sustained release preparation releases the corticosteroid in a controlled or sustained release manner such that the levels of cortisol suppression are at or below 35% by day 14 post-administration, for example post-administration. In some embodiments, the controlled or sustained release preparation releases the corticosteroid in a controlled or sustained release manner such that the levels of cortisol suppression are negligible and/or undetectable by 14 post-administration. In some embodiments, the controlled or sustained release preparation releases the corticosteroid in a controlled or sustained release manner such that the levels of cortisol suppression are negligible at any time post-administration.

The invention provides methods of treating pain or inflammation in a patient comprising administering to said patient a therapeutically effective amount of a formulation selected from the following preparations: (i) a formulation comprising (a) controlled- or sustained-release microparticles comprising a Class B corticosteroid and a lactic acid-glycolic acid copolymer matrix, wherein the Class B corticosteroid comprises between 22% to 28% of the microparticles and wherein the lactic acid-glycolic acid copolymer has one of more of the following characteristics: (1) a molecular weight in the range of about 40 to 70 kDa; (2) an inherent viscosity in the range of 0.5 to 0.5 dL/g; or (3) a lactide:glycolide molar ratio of 80:20 to 60:40; (ii) a formulation comprising (a) controlled- or sustained-release microparticles comprising a Class A corticosteroid and a lactic acid-glycolic acid copolymer matrix, wherein the Class A corticosteroid comprises between 15% to 30% of the microparticles and wherein the lactic acid-glycolic acid copolymer has one of more of the following characteristics: (1) a molecular weight in the range of about 40 to 70 kDa; (2) an inherent viscosity in the range of 0.35 to 0.5 dL/g; or (3) a lactide:glycolide molar ratio of 60:40 to 45:55; (iii) a formulation comprising (a) controlled- or sustained-release microparticles comprising a Class C corticosteroid and a lactic acid-glycolic acid copolymer matrix, wherein the Class C corticosteroid comprises between 15% to 30% of the microparticles and wherein the lactic acid-glycolic acid copolymer has one of more of the following characteristics: (1) a molecular weight in the range of about 40 to 70 kDa; (2) an inherent viscosity in the range of 0.35 to 0.5 dL/g; or (3) a lactide:glycolide molar ratio of 60:40 to 45:55; and (iv) a formulation comprising (a) controlled- or sustained-release microparticles comprising a Class D corticosteroid and a lactic acid-glycolic acid copolymer matrix, wherein the Class D corticosteroid comprises between 8% to 20% of the microparticles and wherein the lactic acid-glycolic acid copolymer has one of more of the following characteristics: (1) a molecular weight in the range of about 40 to 70 kDa; (2) an inherent viscosity in the range of 0.35 to 0.5 dL/g; or (3) a lactide:glycolide molar ratio of 60:40 to 45:55. In some embodiments, the formulation releases the corticosteroid for at least 14 days at a rate that does not adversely suppress the hypothalamic-pituitary-adrenal axis (HPA axis). In some embodiments, the formulation releases the corticosteroid in a controlled or sustained release manner such that the levels of cortisol suppression are at or below 35% by day 14 post-administration, for example post-administration. In some embodiments, the formulation releases the corticosteroid in a controlled or sustained release manner such that the levels of cortisol suppression are negligible and/or undetectable by 14 post-administration. In some embodiments, the formulation releases the corticosteroid in a controlled or sustained release manner such that the levels of cortisol suppression are negligible at any time post-administration.

In some embodiments, the population of microparticles, the controlled or sustained release preparation or formulation is administered as one or more intra-articular injections. In some embodiments, the patient has osteoarthritis, rheumatoid arthritis, acute gouty arthritis, and synovitis. In some embodiments, the patient has acute bursitis, sub-acute bursitis, acute nonspecific tenosynovitis, or epicondylitis.

In one aspect, a method of treating pain and/or inflammation in a joint of a patient is provided that includes administering intra-articularly (e.g., by one or more injections) to a patient with joint disease (e.g., osteoarthritis or rheumatoid arthritis) a formulation that contains one or more corticosteroids, such as those formulations described herein. Therapeutically effective amounts of the one or more corticosteroids are released for a period of time at a rate that does not suppress (e.g., adversely and/or measurably) the HPA axis.

In another aspect, a method of treating pain and/or inflammation in a joint of a patient is provided that includes administering intra-articularly (e.g., by one or more injections) a therapeutically effective amount of one or more corticosteroids in a formulation to a patient with joint disease (e.g., osteoarthritis or rheumatoid arthritis). The formulation has a sustained release microparticle formulation that may or may not release detectable levels of corticosteroid for a length of time following administration and that releases a detectable amount of corticosteroid(s) following administration, where the rate of corticosteroid release from the sustained release microparticle formulation does not adversely suppress the HPA axis. In some embodiments, corticosteroid released from the sustained release microparticle formulation will not measurably suppress the HPA axis.

According to certain embodiments of the foregoing methods, the formulation comprises a population of biodegradable polymer microparticles that contain the corticosteroids. In some embodiments, the corticosteroids are 2% to 75% (w/w) of the microparticles, preferably about 5% to 50% (w/w) of the microparticles, and more preferably 5% to 40% or 10% to 30% (w/w) of the microparticles. In some embodiments, the microparticles have a mass mean diameter of between 10 μm to 100 μm. In some embodiments, the microparticles are formed from a hydrogel, hyaluronic acid, PLA or PLGA. For example, the microparticles are formed from PLGA with a lactide to glycolide co-polymer ratio of about 45:55 to about 80:20. In some embodiments, the corticosteroid is betamethasone, dexamethasone, triamcinolone acetonide, triamcinolone hexacetonide, prednisolone, methylprednisolone, budenoside, mometasone, ciclesonide, fluticasone, salts thereof, esters thereof or combinations thereof.

In yet another aspect, a composition is provided that includes a population of biodegradable polymer microparticles that contain corticosteroid(s). For example, the corticosteroid is betamethasone, dexamethasone, triamcinolone acetonide, triamcinolone hexacetonide, prednisolone, methylprednisolone, budenoside, mometasone, ciclesonide, fluticasone, salts thereof, esters thereof or combinations thereof. When the composition is administered intra-articularly (e.g., by one or more injections), a therapeutically effective amount of corticosteroid(s) is released for a period of time at a rate that does not suppress the HPA axis. In some embodiments, the corticosteroid(s) released will not adversely suppress the HPA axis. In some embodiments, the corticosteroid(s) released will not measurably suppress the HPA axis.

In yet a further aspect, a composition is provided that includes a population of biodegradable polymer microparticles that contain corticosteroid(s). For example, the corticosteroid is betamethasone, dexamethasone, triamcinolone acetonide, triamcinolone hexacetonide, prednisolone, methylprednisolone, budenoside, mometasone, ciclesonide, fluticasone, salts thereof, esters thereof or combinations thereof. When the composition is administered intra-articularly (e.g., by one or more injections), therapeutically effective amounts of corticosteroid(s) are released following administration from a first component for a first length of time and from a sustained release component for a second length of time. Furthermore, the rate of corticosteroid(s) released from the sustained release component does not suppress the HPA axis. In some embodiments, the corticosteroid(s) released from the sustained release component during the second length of time will not adversely suppress the HPA axis. In some embodiments, the corticosteroid(s) released from the sustained release component during the second length of time will not measurably suppress the HPA axis. In some embodiments, the first component comprises a corticosteroid containing solution or suspension. In some embodiments, the first component contains a corticosteroid that is different from that of the sustained release component. In other embodiments, the same corticosteroid is used in both the first and sustained release components.

According to certain embodiments of the foregoing compositions, the corticosteroids are 2% to 75% (w/w) of the microparticles, preferably about 5% to 50% (w/w) of the microparticles, and more preferably 5% to 40% (w/w) of the microparticles. In some embodiments, the microparticles have a mass mean diameter of between 10 µm to 100 µm. In some embodiments, the microparticles are formed from a hydrogel, hyaluronic acid, PLA or PLGA. For example, the microparticles are formed from PLGA with a lactide to glycolide co-polymer ratio of about 45:55 to about 80:20. In some embodiments, the compositions further comprise a corticosteroid containing solution or suspension. In some embodiments, the corticosteroid containing solution or suspension contains a corticosteroid that is different from that found in the microparticles.

The invention also provides methods of slowing, arresting or reversing progressive structural tissue damage associated with chronic inflammatory disease in a patient comprising administering to said patient a therapeutically effective amount of a population of microparticles selected from the following populations: (i) a population of microparticles comprising a Class B corticosteroid or a pharmaceutically acceptable salt thereof incorporated in a lactic acid-glycolic acid copolymer matrix, wherein the Class B corticosteroid comprises between 22% to 28% of the microparticles; (ii) a population of microparticles comprising a Class A corticosteroid or a pharmaceutically acceptable salt thereof incorporated in a lactic acid-glycolic acid copolymer matrix, wherein the Class A corticosteroid comprises between 15% to 30% of the microparticles; (iii) a population of microparticles comprising a Class C corticosteroid or a pharmaceutically acceptable salt thereof incorporated in a lactic acid-glycolic acid copolymer matrix, wherein the Class C corticosteroid comprises between 15% to 30% of the microparticles; and (iv) a population of microparticles comprising a Class D corticosteroid or a pharmaceutically acceptable salt thereof incorporated in a lactic acid-glycolic acid copolymer matrix, wherein the Class D corticosteroid comprises between 8% to 20% of the microparticles. In some embodiments, the population of microparticles releases the corticosteroid for at least 14 days at a rate that does not adversely suppress the hypothalamic-pituitary-adrenal axis (HPA axis).

The invention also provides methods of slowing, arresting or reversing progressive structural tissue damage associated with chronic inflammatory disease in a patient comprising administering to said patient a therapeutically effective amount of a controlled or sustained release preparation selected from the following preparations: (i) a controlled or sustained release preparation of a Class B corticosteroid comprising a lactic acid-glycolic acid copolymer microparticle containing the Class B corticosteroid, wherein the Class B corticosteroid comprises between 22% to 28% of the lactic acid-glycolic acid copolymer microparticle matrix; (ii) a controlled or sustained release preparation of a Class A corticosteroid comprising a lactic acid-glycolic acid copolymer microparticle containing the Class A corticosteroid, wherein the Class A corticosteroid comprises between 15% to 30% of the lactic acid-glycolic acid copolymer microparticle matrix; (iii) a controlled or sustained release preparation of a Class C corticosteroid comprising a lactic acid-glycolic acid copolymer microparticle containing the Class C corticosteroid, wherein the Class C corticosteroid comprises between 15% to 30% of the lactic acid-glycolic acid copolymer microparticle matrix; and (iv) a controlled or sustained release preparation of a Class D corticosteroid comprising a lactic acid-glycolic acid copolymer microparticle containing the Class D corticosteroid, wherein the Class D corticosteroid comprises between 8% to 20% of the lactic acid-glycolic acid copolymer microparticle matrix. In some embodiments, the controlled or sustained release preparation releases the corticosteroid for at least 14 days at a rate that does not adversely suppress the hypothalamic-pituitary-adrenal axis (HPA axis).

The invention also provides methods of slowing, arresting or reversing progressive structural tissue damage associated with chronic inflammatory disease in a patient comprising administering to said patient a therapeutically effective amount of a formulation selected from the following preparations: (i) a formulation comprising (a) controlled- or sustained-release microparticles comprising a Class B corticosteroid and a lactic acid-glycolic acid copolymer matrix, wherein the Class B corticosteroid comprises between 22% to 28% of the microparticles and wherein the lactic acid-glycolic acid copolymer has one of more of the following characteristics: (1) a molecular weight in the range of about 40 to 70 kDa; (2) an inherent viscosity in the range of 0.3 to 0.5 dL/g; or (3) a lactide:glycolide molar ratio of 80:20 to 60:40; (ii) a formulation comprising (a) controlled- or sustained-release microparticles comprising a Class A corticosteroid and a lactic acid-glycolic acid copolymer matrix, wherein the Class A corticosteroid comprises between 15% to 30% of the microparticles and wherein the lactic acid-glycolic acid copolymer has one of more of the following characteristics: (1) a molecular weight in the range of about 40 to 70 kDa; (2) an inherent viscosity in the range of 0.35 to 0.5 dL/g; or (3) a lactide:glycolide molar ratio of 60:40 to 50:50; (iii) a formulation comprising (a) controlled- or sustained-release microparticles comprising a Class C corticosteroid and a lactic acid-glycolic acid copolymer matrix, wherein the Class C corticosteroid comprises between 15% to 30% of the microparticles and wherein the lactic acid-glycolic acid copolymer has one of more of the following characteristics: (1) a molecular weight in the range of about 40 to 70 kDa; (2) an inherent viscosity in the range of 0.35 to 0.5 dL/g; or (3) a lactide:glycolide molar ratio of 60:40 to 50:50; and (iv) a formulation comprising (a) controlled- or sustained-release microparticles comprising a Class D corticosteroid and a lactic acid-glycolic acid copolymer matrix, wherein the Class D corticosteroid comprises between 8% to 20% of the microparticles and wherein the lactic acid-glycolic acid copolymer has one of more of the following characteristics: (1) a molecular weight in the range of about 40 to 70 kDa; (2) an inherent viscosity in the range of 0.35 to 0.5 dL/g; or (3) a lactide:glycolide molar ratio of 60:40 to 50:50. In some embodiments, the formulation releases the corticosteroid for at least 14 days at a rate that does not adversely suppress the hypothalamic-pituitary-adrenal axis (HPA axis).

In some embodiments, the population of microparticles, the controlled or sustained release preparation or formulation is administered as one or more intra-articular injections. In some embodiments, the patient has osteoarthritis, rheumatoid arthritis, acute gouty arthritis, and synovitis. In some embodiments, the patient has acute bursitis, sub-acute bursitis, acute nonspecific tenosynovitis, or epicondylitis.

The invention also provides methods to slow, arrest, reverse or otherwise inhibit progressive structural tissue damage associated with chronic inflammatory disease, for example, damage to cartilage associated with osteoarthritis. In one embodiment, the method includes the administration to a patient, for example local administration, of a therapeutically effective amount of one or more corticosteroids in a formulation, wherein the formulation releases the corticosteroid(s) for at least 14 days at a rate that does not adversely suppress the hypothalamic-pituitary-adrenal axis (HPA axis). The methods to assess the effect of corticosteroid formulations on disease progression include controlled clinical studies that assess clinical end points and/or employ imaging technologies such as, for example Magnetic Resonance Imaging (MRI), to determine effects on the structure in chronically inflamed tissues, for example the effects on cartilage volume and other articular and peri-articular structures in osteoarthritis and rheumatoid arthritis. (See e.g., Eckstein F, et al. "Magnetic resonance imaging (MRI) of articular cartilage in knee osteoarthritis (OA): morphological assessment." *Osteoarthritis Cartilage* 14 Suppl A (2006): A46-75; Lo G H, et al. "Bone marrow lesions in the knee are associated with increased local bone density." *Arthritis Rheum* 52 (2005): 2814-21; and Lo G H, et al. "The ratio of medial to lateral tibial plateau bone mineral density and compartment-specific tibiofemoral osteoarthritis." *Osteoarthritis Cartilage* 14 (2006): 984-90 the contents of each of which are hereby incorporated by reference in their entirety.) The corticosteroid microparticle formulations provided herein appear to exhibit little to no negative effects, e.g., structural tissue damage, and from preliminary data and studies described in the Examples below, these corticosteroid microparticle formulations appear to have a positive effect, e.g., slowing, arresting or reversing structural tissue damage.

The invention also provides methods of treating pain and/or inflammation of a patient by administering to the patient a therapeutically effective amount of one or more corticosteroids in a formulation, wherein the formulation releases the corticosteroid(s) for at least 14 days at a rate that does not adversely suppress the hypothalamic-pituitary-adrenal axis (HPA axis).

The invention also provides methods of manufacturing the corticosteroid microparticle formulations. The microparticle formulations provided herein can be manufactured using any of a variety of suitable methods.

For the Class B corticosteroid microparticle formulations, in some embodiments, the microparticles are manufactured as described in the Examples provided below. For the Class B corticosteroid microparticle formulations, in some embodiments, the microparticles are manufactured as described in U.S. Pat. Nos. 7,261,529 and 7,758,778, the contents of each of which are hereby incorporated by reference in their entirety. For example, the microparticles are manufactured using a solvent evaporation process wherein the Class B corticosteroid is dispersed in a lactic acid-glycolic acid copolymer organic solution and the mixture is treated to remove the solvent from the mixture, thereby producing microparticles.

In some embodiments, the solvent evaporation process utilizes a spray drying or fluid bed apparatus to remove the solvent and produce microparticles. In some embodiments, the solvent evaporation process utilizes a spinning disk. For example, the spinning disk is the spinning disk as described in U.S. Pat. Nos. 7,261,529 and 7,758,778.

For the Class B corticosteroid microparticle formulations, in some embodiments where the Class B corticosteroid is TCA, the microparticles are manufactured using a solid in oil in water emulsion process wherein TCA is dispersed in a lactic acid-glycolic acid copolymer organic solution and added to an aqueous solvent to produce microparticles.

For the Class A, C and/or D corticosteroid microparticle formulations, in some embodiments, the microparticles are manufactured as described in the Examples provided below. For Class A, C and/or D corticosteroid formulations, in some embodiments, the microparticles are manufactured as described in PCT Publication No. WO 95/13799, the contents of which are hereby incorporated by reference in their entirety. For example, the microparticles are manufactured using a solid in oil in water emulsion process wherein the Class A corticosteroid, Class C corticosteroid and/or Class D corticosteroid is dispersed in a lactic acid-glycolic acid copolymer organic solution and added to an aqueous solvent to produce microparticles.

It is contemplated that whenever appropriate, any embodiment of the present invention can be combined with one or more other embodiments of the present invention, even though the embodiments are described under different aspects of the present invention.

BRIEF DESCRIPTION OF THE FIGURES

FIGS. 4A-4F are a series of graphs depicting plasma levels of endogenous cortisol over time, without (FIGS. 4A, 4C, and 4E) adjustment for a change in the sensitivity of the HPA axis after intra-articular corticosteroids and with (FIGS. 4B, 4D, and 4F) adjustment for a change in the sensitivity of the HPA axis after intra-articular corticosteroids. These data demonstrate that the sensitivity of the HPA axis varies with corticosteroid, dose, and time with clinically important implications for the selection of doses for sustained delivery into an intra-articular space.

In FIG. 44A, FX006 at 0.28, 0.12 and 0.03 mg (TCA doses) is expressed as TCA concentrations of the dosing formulation (4.67, 2 and 0.5 mg/ml). In FIG. 44B, FX006 at 0.28 mg (TCA dose) is expressed as TCA concentrations of the dosing formulation (4.67 mg/ml). Similarly, TCA IR at 0.03 mg is expressed as triamcinolone at 0.5 mg/ml. In FIG. 44C, FX006 at 0.28, 0.12 and 0.03 mg (TCA doses) is expressed as TCA concentrations of the dosing formulation (4.67, 2 and 0.5 mg/ml). Similarly, TCA IR at 0.06 and 0.03 mg is expressed as triamcinolone at 1 and 0.5 mg/ml.

DETAILED DESCRIPTION OF THE INVENTION

Figure 1:
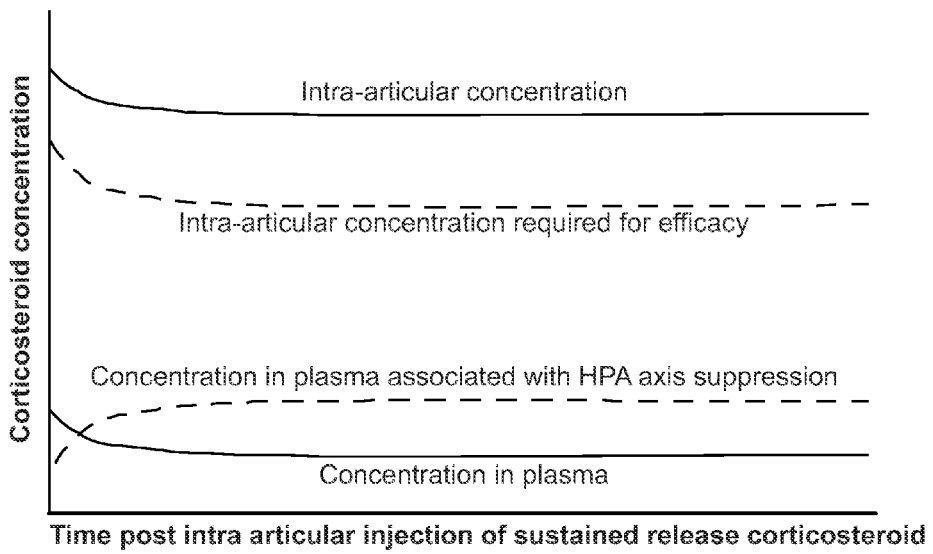
FIG. 1 is a graph depicting the intra-articular concentrations (top solid line) and the systemic concentrations (bottom solid line) of the glucocorticoid administered according to certain embodiments of the present invention following intra-articular injection. The systemic glucocorticoid concentration associated with clinically significant suppression of the HPA axis is shown as the bottom dotted line. The top dotted line represents the minimal intra-articular concentration required to maintain efficacy (defined as relief of pain and inflammation, or slowing, arrest, or reversal of structural damage to tissues caused by inflammatory diseases. Sustained release of the corticosteroid provides sufficient intra-articular concentrations to maintain efficacy in the longer term, and has transient, clinically insignificant effect on the HPA axis.

The invention provides compositions and methods for the treatment of pain and inflammation using corticosteroids. The compositions and methods provided herein use one or more corticosteroids in a microparticle formulation. The corticosteroid microparticle formulations provided herein are effective at treating pain and/or inflammation with minimal prolonged suppression of the HPA axis and/or other long term side effects of corticosteroid administration. The corticosteroid microparticle formulations provided herein are effective in slowing, arresting, reversing or otherwise inhibiting structural damage to tissues associated with progressive disease with minimal prolonged suppression of the HPA axis and/or other long term side effects of corticosteroid administration. The corticosteroid microparticle formulations provided herein deliver the corticosteroid in a dose and in a sustained release manner such that the levels of cortisol suppression are at or below 35% by day 14 post-injection. In some embodiments, the corticosteroid microparticle formulations provided herein deliver the corticosteroid in a dose and in a controlled or sustained release manner such that the levels of cortisol suppression are negligible and/or undetectable by 14 post-injection. Thus, the corticosteroid microparticle formulations in these embodiments are effective in the absence of any significant HPA axis suppression. Administration of the corticosteroid microparticle formulations provided herein can result in an initial "burst" of HPA axis suppression, for example, within the first few days, within the first two days and/or within the first 24 hours post-injection, but by day 14 post-injection, suppression of the HPA axis is less than 35%.

The use of microparticles to administer corticosteroids is known (See, e.g., U.S. Patent Application Publication. No. 20080317805). In addition, corticosteroids are known to be useful for the symptomatic treatment of inflammation and pain. New data also suggest that synovitis may be associated with the structural damage, for example, the deterioration of cartilage and other peri-articular associated with the progression of osteoarthritis and rheumatoid arthritis. (See e.g., Hill C L, et al. "Synovitis detected on magnetic resonance imaging and its relation to pain and cartilage loss in knee osteoarthritis." *Ann Rheum Dis* 66 (2007):1599-603; van den Berg W B, et al. "Synovial mediators of cartilage damage and repair in osteoarthritis." In: Brandt K D, Doherty M, Lohmander L S, eds. Osteoarthritis. Second ed. Oxford: Oxford University Press (2003):147-55; Ayral X, et al. "Synovitis: a potential predictive factor of structural progression of medial tibiofemoral knee osteoarthritis—results of a 1 year longitudinal arthroscopic study in 422 patients." *Osteoarthritis Cartilage* 13 (2005):361-7; and Kirwan J R, et al. "Effects of glucocorticoids on radiological progression in rheumatoid arthritis." *Cochrane Database Syst Rev* 2007:CD006356).

The administration of corticosteroids, particularly for extended periods of time, can have a number of unwanted side effects. The HPA axis, the interdependent feedback mechanism between the hypothalamus, the pituitary gland and the adrenal cortex, may be suppressed by the administration of corticosteroids, leading to a variety of unwanted side effects. The extent of HPA axis suppression, and related inhibition of endogenous cortisol production, has been attributed to the potency of the corticosteroid, the dose, systemic concentration, protein binding, rate of elimination (Meibohm et al. "Mechanism-based PK/PD model for the lymphocytopenia induced by endogenous and exogenous corticosteroids." *Int J Clin Pharmacol Ther.* 37 (8) (1999): 367-76) and, for one corticosteroid, a change in sensitivity of the HPA axis (Derendorf et al. "Clinical PK/PD modelling as a tool in drug development of corticosteroids." *Int J Clin Pharmacol Ther.* 35 (10) 1997: 481-8). Furthermore, intra-articular doses of corticosteroids associated with only limited anti-inflammatory and short-term analgesic benefit (Hepper et al. "The efficacy and duration of intra-articular corticosteroid injection for knee osteoarthritis: a systematic review of level I studies." *J Am Acad Orthop Surg.* 17 (10) 2009: 638-46) have been associated with HPA axis suppression (Habib, "Systemic effects of intra-articular corticosteroids." *Clin Rheumatol.* 28 (7) (2009): 749-56).

The changes in sensitivity to corticosteroid effects over time should alter clinical steroid dosing, but prior to the instant invention, this has not been understood.

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

Definitions

The terms below have the following meanings unless indicated otherwise.

An amount of a corticosteroid that does not "suppress the hypothalamic-pituitary-adrenal axis (HPA axis)" refers to the amount of the sustained release corticosteroid delivered locally to relieve pain due to inflammation, which provides a systemic concentration that will not have a clinically significant effect or "adverse effect" on the HPA axis. Suppression of the HPA axis is generally manifested by a reduction in endogenous glucocorticoid production. It is useful to consider both basal and augmented production of endogenous glucocorticoids. Under ordinary, "unstressed" conditions, glucocorticoid production occurs at a normal, basal level. There is some natural variation of production during the course of the 24-hour day. Under extraordinary, "stressed" conditions associated with, e.g., infection or trauma and the like, augmented endogenous production of glucocorticoids occurs. Endogenous cortisol production may be determined by measuring glucocorticoid concentrations in plasma, saliva, urine or by any other means known in the art. It is known that systemic concentrations of corticosteroids can suppress the HPA axis. For example, on day 3 after an intra-articular injection of 20 mg triamcinolone hexacetonide plasma levels, of approximately 3-4 ng/mL have been observed. These resulted in a transient but highly statistically significant 75% HPA-axis suppression (Derendorf et al., "Pharmacokinetics and pharmacodynamics of glucocorticoid suspensions after intra-articular administration." *Clin Pharmacol Ther.* 39 (3) (1986):313-7) which, however, does not necessarily portend complete HPA failure (Habib, "Systemic effects of intra-articular corticosteroids." *Clin Rheumatol* 28 (2009): 749-756, see p 752 col. 1, para 2, final sentence). While such transient suppression is generally considered to be acceptable without clinically significant effect, more persistent suppression, i.e., weeks, would be deemed clinically detrimental. In embodiments of the present invention, administration of the formulation may result in a clinically acceptable HPA suppression, particularly during the initial release period of the therapy. In some embodiments of the present invention, administration of the formulation will not result in any significant level of HPA suppression, including no detectable HPA suppression, particularly during the initial release period of the therapy. During the subsequent or sustained release period of the therapy, additional corticosteroid may be released into the plasma. However, the plasma levels during this period will generally be less than those during the initial release period, if any corticosteroid release occurs, and will not be associated with HPA axis suppression. Further, the adverse events associated with exogenous corticosteroid administration, e.g., hyperglycemia, hypertension, altered mood, etc. will generally not be observed. Preferably, the number of clinical adverse events during this period will not substantially exceed the number achieved by an immediate release formulation alone or by KENALOG™ or its bioequivalent and will, preferably, be fewer than during the prior, initial release period of the therapy, if any corticosteroid release occurs. Alternatively, one can determine the suppression of the formulation on HPA by measuring endogenous cortisol production. Thus, the formulation can be considered as avoiding clinically significant (or adverse) suppression of the HPA axis where the endogenous cortisol level is substantially the same in the steady state between a patient population receiving a therapeutically beneficial amount of an immediate release formulation and those receiving a therapeutically beneficial amount of a sustained release formulation. Such a formulation would be deemed to have no clinically significant effect on the HPA axis. Alternatively or additionally, a small but measurable reduction in steady-state glucocorticoid production can result from the formulation during the sustained release period of the therapy with adequate preservation of the augmented, stress response needed during infection or trauma can be deemed a clinically insignificant suppression of the HPA axis. Endogenous glucocorticoid production may be assessed by administering various doses of adrenocorticotropin hormone or by other tests known to those skilled in the art. Embodiments of the current invention provide for controlling the release of corticosteroid, as may be desired, to achieve either no measurable effect on endogenous glucocorticoid production or a target, or a measurable effect that is, however, without adverse clinical consequence. In this regard, it has been found that intra-articular doses of corticosteroids that suppress cortisol production by 20-35%, and sometimes more, provide very useful sustained anti-inflammatory and analgesic activity. These benefits are achieved without acute risks of hypoadrenalism and without excessive risks, after sustained intra-articular dosing, of developing an adrenal unresponsiveness in times of stress or of developing frank adrenal failure.

As shown further below, the studies presented herein have demonstrated that the HPA axis sensitivity appears to diminish with time, steroid, and dose. In this regard, it has been determined that standard doses of familiar corticosteroids, when examined from the viewpoint of steady-state HPA axis suppression (i.e., after desensitization has occurred), provide clinically useful benchmarks. For example, while oral prednisolone given at 20 mg QD produces a 73% cortisol suppression, even 5 mg QD (considered a "low dose") is associated with a 40% suppression of endogenous cortisol production. Doses at or below 5 mg of prednisolone per day are generally considered to be well tolerated and are not associated with clinically meaningful HPA axis suppression (La Rochelle et al., "Recovery of the hypothalamic-pituitary-adrenal (HPA) axis in patients with rheumatic diseases receiving low-dose prednisolone." Am. J. Med. 95 (1993): 258-264). Therefore, up to approximately 40% suppression will be clinically well tolerated and very unlikely to be associated with importantly adverse clinical events such as hypoadrenalism or soft-tissue or bony or metabolic changes indicative of long-term glucocorticoid excess.

"Patient" refers to a human diagnosed with a disease or condition that can be treated in accordance to the inventions described herein. In some embodiments it is contemplated that the formulations described herein may also be used in horses.

"Delivery" refers to any means used to place the drug into a patient. Such means may include without limitation, placing matrices into a patient that release the drug into a target area. One of ordinary skill in the art recognizes that the matrices may be delivered by a wide variety of methods, e.g., injection by a syringe, placement into a drill site, catheter or canula assembly, or forceful injection by a gun type apparatus or by placement into a surgical site in a patient during surgery.

The terms "treatment" and "treating" a patient refer to reducing, alleviating, stopping, blocking, or preventing the symptoms of pain and/or inflammation in a patient. As used herein, "treatment" and "treating" includes partial alleviation of symptoms as well as complete alleviation of the symptoms for a time period. The time period can be hours, days, months, or even years.

By an "effective" amount or a "therapeutically effective amount" of a drug or pharmacologically active agent is meant a nontoxic but sufficient amount of the drug or agent to provide the desired effect, e.g., analgesia. An appropriate "effective" amount in any individual case may be determined by one of ordinary skill in the art using routine experimentation.

"Site of a patient's pain" refers to any area within a body causing pain, e.g., a knee joint with osteoarthritis, nerve root causing sciatic pain, nerve fibers growing into annular tears in discs causing back pain, temporomandibular joint (TMJ) pain, for example TMJ pain associated with temporomandibular joint disorder (TMD) or pain radiating from epidural or perineural spaces. The pain perceived by the patient may result from inflammatory responses, mechanical stimuli, chemical stimuli, thermal stimuli, as well as allodynia.

Additionally, the site of a patient's pain can comprise one or multiple sites in the spine, such as between the cervical, thoracic, or lumbar vertebrae, or can comprise one or multiple sites located within the immediate area of inflamed or injured joints such as the shoulder, hip, or other joints.

A "biocompatible" material refers to a material that is not toxic to the human body, it is not carcinogenic and it should induce limited or no inflammation in body tissues. A "biodegradable" material refers to a material that is degraded by bodily processes (e.g., enzymatic) to products readily disposable by the body or absorbed into body tissue. The biodegraded products should also be biocompatible with the body. In the context of intra-articular drug delivery systems for corticosteroids, such polymers may be used to fabricate, without limitation: microparticles, micro-spheres, matrices, microparticle matrices, micro-sphere matrices, capsules, hydrogels, rods, wafers, pills, liposomes, fibers, pellets, or other appropriate pharmaceutical delivery compositions that a physician can administer into the joint. The biodegradable polymers degrade into non-toxic residues that the body easily removes or break down or dissolve slowly and are cleared from the body intact. The polymers may be cured ex-vivo forming a solid matrix that incorporates the drug for controlled release to an inflammatory region. Suitable biodegradable polymers may include, without limitation natural or synthetic biocompatible biodegradable material. Natural polymers include, but are not limited to, proteins such as albumin, collagen, gelatin synthetic poly(aminoacids), and prolamines; glycosaminoglycans, such as hyaluronic acid and heparin; polysaccharides, such as alginates, chitosan, starch, and dextrans; and other naturally occurring or chemically modified biodegradable polymers. Synthetic biocompatible biodegradable materials include, but are not limited to, poly(lactide-co-glycolide) (PLGA), polylactide (PLA), polyglycolide (PG), polyhydroxybutyric acid, poly(trimethylene carbonate), polycaprolactone (PCL), polyvalerolactone, poly(alpha-hydroxy acids), poly(lactones), poly(amino-acids), poly(anhydrides), polyketals poly(arylates), poly(orthoesters), polyurethanes, polythioesters, poly(orthocarbonates), poly(phosphoesters), poly(ester-co-amide), poly(lactide-co-urethane, polyethylene glycol (PEG), polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, and PLGA-PEO-PLGA blends and copolymers thereof and any combinations thereof. The biocompatible biodegradable material can include a combination of biocompatible biodegradable materials. For example, the biocompatible biodegradable material can be a triblock, or other multi-block, formation where a combination of biocompatible biodegradable polymers are joined together. For example, the triblock can be PLGA-PEG-PLGA.

Diseases that May be Treated Using the Formulations of this Invention

Descriptions of various embodiments of the invention are given below. Although these embodiments are exemplified with reference to treat joint pain associated with osteoarthritis, rheumatoid arthritis and other joint disorders, it should not be inferred that the invention is only for these uses. Rather, it is contemplated that embodiments of the present invention will be useful for treating other forms of joint pain by administration into articular and periarticular spaces. In addition, it will be understood that for some embodiments injection near a joint may be equivalent to injections in that joint. It is also contemplated that embodiments of the present invention may be useful for injection or administration into soft tissues or lesions. Any and all uses of specific words and references are simply to detail different embodiments of the present invention.

Local administration of a corticosteroid microparticle formulation can occur, for example, by injection into the intra-articular space, peri-articular space, soft tissues, lesions, epidural space, perineural space, or the foramenal space at or near the site of a patient's pain and/or structural tissue damage. Local injection of the formulations described herein into articular or periarticular spaces may be useful in the treatment of, for example, juvenile rheumatoid arthritis, sciatica and other forms of radicular pain (e.g., arm, neck, lumbar, thorax), psoriatic arthritis, acute gouty arthritis, Morton's neuroma, acute and subacute bursitis, acute and subacute nonspecific tenosynovitis and epicondylitis, acute rheumatic carditis and ankylosing spondylitis. Injection of the microparticles described herein into soft tissues or lesions may be useful in the treatment of, for example, alopecia greata, discoid lupus, erythematosus; keloids, localized hypertrophic, infiltrated inflammatory lesions of granuloma annulare, lichen planus, lichen simplex chronicus (neurodermatitis), psoriasis and psoriatic plaques; necrobiosis lipoidica diabeticorum, and psoriatic arthritis. Injection of the microparticles described herein into epidural spaces may be useful in the treatment of, for example, neurogenic claudication. Intramuscular or other soft tissues or lesions injections may also be useful in providing systemic exposures that are effective in the control of incapacitating allergic conditions (including but not limited to asthma, atopic dermatitis, contact dermatitis, drug hypersensitivity reactions, seasonal or perennial allergic rhinitis, serum sickness, transfusion reactions), bullous dermatitis herpetiformis, exfoliative dermatitis, mycosis fungoides, pemphigus, severe erythema multiforme (Stevens-Johnson syndrome), Primary or secondary adrenocortical insufficiency in conjunction with mineralocorticoids where applicable; congenital adrenal hyperplasia, hypercalcemia associated with cancer, nonsupportive thyroiditis, exacerbations of regional enteritis and ulcerative colitis, acquired (autoimmune) hemolytic anemia, congenital (erythroid) hypoplastic anemia (Diamond blackfan anemia), pure red cell aplasia, select cases of secondary thrombocytopenia, trichinosis with neurologic or myocardial involvement, tuberculous meningitis with subarachnoid block or impending block when used concurrently with appropriate antituberculous chemotherapy, palliative management of leukemias and lymphomas, acute exacerbations of multiple sclerosis, cerebral edema associated with primary or metastatic brain tumor or craniotomy, to induce diuresis or remission of proteinuria in idiopathic nephrotic syndrome, or to induce diuresis or remission of proteinuria in lupus erythematosus, berylliosis, symptomatic sarcoidosis, fulminating or disseminated pulmonary tuberculosis (when used concurrently with appropriate antituberculous chemotherapy), idiopathic eosinophilic pneumonias, symptomatic sarcoidosis, dermatomyositis, polymyositis, and systemic lupus erythematosus, post-operative pain and swelling.

In one embodiment, the corticosteroid microparticle formulations provided herein are useful in treating, alleviating a symptom of, ameliorating and/or delaying the progression of sciatica. In one embodiment, corticosteroid microparticle formulations provided herein are useful in treating, alleviating a symptom of, ameliorating and/or delaying the progression of temporomandibular joint disorder (TMD).

In one embodiment, the corticosteroid microparticle formulations provided herein are useful in treating, alleviating a symptom of, ameliorating and/or delaying the progression of neurogenic claudication secondary to lumbar spinal stenosis (LSS). LSS implies spinal canal narrowing with possible subsequent neural compression (classified by anatomy or etiology). Neurogenic Claudication (NC) is a hallmark symptom of lumbar stenosis, in which the column of the spinal cord (or the canals that protect the nerve roots) narrows at the lower back. This narrowing can also occur in the spaces between the vertebrae where the nerves leave the spine to travel to other parts of the body.

The microparticles of the invention are used to treat, alleviate a symptom of, ameliorate and/or delay the progression patients suffering from NC secondary to LSS. The corticosteroid microparticle formulations can be administered, for example, by epidural steroid injection (ESI).

Administration of a corticosteroid microparticle formulation, e.g., a TCA microparticle formulation, to a patient suffering from an inflammatory disease such as osteoarthritis or rheumatoid arthritis, is considered successful if any of a variety of laboratory or clinical results is achieved. For example, administration of a corticosteroid microparticle formulation is considered successful if one or more of the symptoms associated with the disease is alleviated, reduced, inhibited or does not progress to a further, i.e., worse, state. Administration of a corticosteroid microparticle formulation is considered successful if the disease, e.g., an arthritic or other inflammatory disease, enters remission or does not progress to a further, i.e., worse, state.

Also, any and all alterations and further modifications of the invention, as would occur to one of ordinary skill in the art, are intended to be within the scope of the invention Selection of Corticosteroids and Drug Dosage Corticosteroids associated with embodiments of the present invention can be any naturally occurring or synthetic steroid hormone. Naturally occurring corticosteroids are secreted by the adrenal cortex or generally the human body.

Corticosteroid molecules have the following basic structure:

(I)

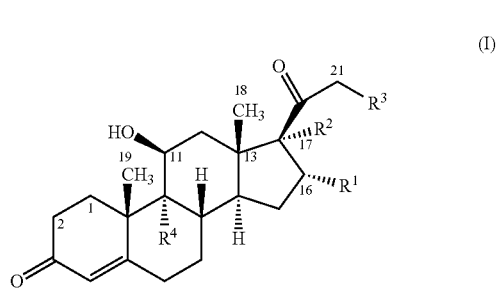

Corticosteroids have been classified into four different groups (A, B, C, and D). (See e.g., Foti et al. "Contact Allergy to Topical Corticosteroids: Update and Review on Cross-Sensitization." *Recent Patents on Inflammation & Allergy Drug Discovery* 3 (2009): 33-39; Coopman et al., "Identification of cross-reaction patterns in allergic contact dermatitis to topical corticosteroids." *Br J Dermatol* 121 (1989): 27-34). Class A corticosteroids are hydrocortisone types with no modification of the D ring or C20-C21 or short chain esters on C20-C21. Main examples of Class A corticosteroids include prednisolone, hydrocortisone and methylprednisolone and their ester acetate, sodium phosphate and succinate, cortisone, prednisone, and tixocortol pivalate. Class B corticosteroids are triamcinolone acetonide (TCA) types with cis/ketalic or diolic modifications on C16-C17. Main examples of Class B corticosteroids include triamcinolone acetonide (TCA), fluocinolone acetonide, amcinonide, desonide, fluocinonide, halcinonide, budesonide, and flunisolide. Class C corticosteroids are betamethasone types with a —CH3 mutilation on C16, but no esterification on C17-C21. Main examples of Class C corticosteroids include betamethasone, dexamethasone, desoxymethasone, fluocortolone, and halomethasone. Class D corticosteroids are clobetasone or hydrocortisone esterified types with a long chain on C17 and/or C21 and with no methyl group on C16. Main examples of Class D corticosteroids include fluticasone, clobetasone butyrate, clobetasol propionate, hydrocortisone-17-aceponate, hydrocortisone-17-butyrate, beclomethasone dipropionate, betamethasone-17-valerate, betamethasone dipropionate, methylprednisolone aceponate, and prednicarbate.

For the present invention non-limiting examples of corticosteroids may include: betamethasone, betamethasone acetate, betamethasone dipropionate, betamethasone 17-valerate, cortivazol, dexamethasone, dexamethasone acetate, dexamethasone sodium phosphate, hydrocortisone, hydrocortisone aceponate, hydrocortisone acetate, hydrocortisone butyrate, hydrocortisone cypionate, hydrocortisone probutate, hydrocortisone sodium phosphate, hydrocortisone sodium succinate, hydrocortisone valerate, methylprednisolone, methylprednisolone aceponate, methylprednisolone acetate, methylprednisolone sodium succinate, prednisolone, prednisolone acetate, prednisolone metasulphobenzoate, prednisolone sodium phosphate, prednisolone steaglate, prednisolone tebutate, triamcinolone, triamcinolone acetonide, triamcinolone acetonide 21-palmitate, triamcinolone benetonide, triamcinolone diacetate, triamcinolone hexacetonide, alclometasone, alclometasone dipropionate, amcinonide, amelometasone, beclomethasone, beclomethasone dipropionate, beclomethasone dipropionate monohydrate, budesonide, butixocort, butixocort propionate, ciclesonide, ciprocinonide, clobetasol, clobetasol propionate, clocortolone, clobetasone, clobetasone butyrate, clocortolone pivalate, cloprednol, cortisone, cortisone acetate, deflazacort, domoprednate, deprodone, deprodone propionate, desonide, desoximethasone, desoxycortone, desoxycortone acetate, dichlorisone, diflorasone, diflorasone diacetate, diflucortolone, difluprednate, fluclorolone, fluclorolone acetonide, fludrocortisone, fludrocortisone acetate, fludroxycortide, flumethasone, flumethasone pivalate, flunisolide, fluocinolone, fluocinolone acetonide, fluocortin, fluocortolone, fluorometholone, fluticasone, fluticasone furoate, fluticasone propionate, fluorometholone acetate, fluoxymesterone, fluperolone, fluprednidene, fluprednidene acetate, fluprednisolone, formocortal, halcinonide, halobetasol propionate, halometasone, halopredone, halopredone acetate, hydrocortamate, isoflupredone, isoflupredone acetate, itrocinonide, loteprednol etabonate, mazipredone, meclorisone, meclorisone dibutyrate, medrysone, meprednisone, mometasone, mometasone furoate, mometasone furoate monohydrate, nivacortol, paramethasone, paramethasone acetate, prednazoline, prednicarbate, prednisolone, prednylidene, procinonide, rofleponide, rimexolone, timobesone, tipredane, tixocortol, tixocortol pivalate and tralonide.

Embodiments of the invention include using sustained release corticosteroids delivered to treat pain at dosages that do not adversely suppress the HPA axis. Such amounts delivered locally to relieve pain due to inflammation, will provide a systemic concentration that does not have a measurable adverse effect on the HPA axis (differences if any are not significant because any such differences are within normal assay variability) or, as desired, may have a measurable but clinically insignificant effect on the HPA axis (basal cortisol is suppressed to some measurable extent but stress responses are adequately preserved). Further embodiments of the invention include doses during a second period of time selected to adjust for a change in sensitivity of the HPA axis to suppression following exposure during a first period of time to the corticosteroid (FIG. 1).

Figure 2:
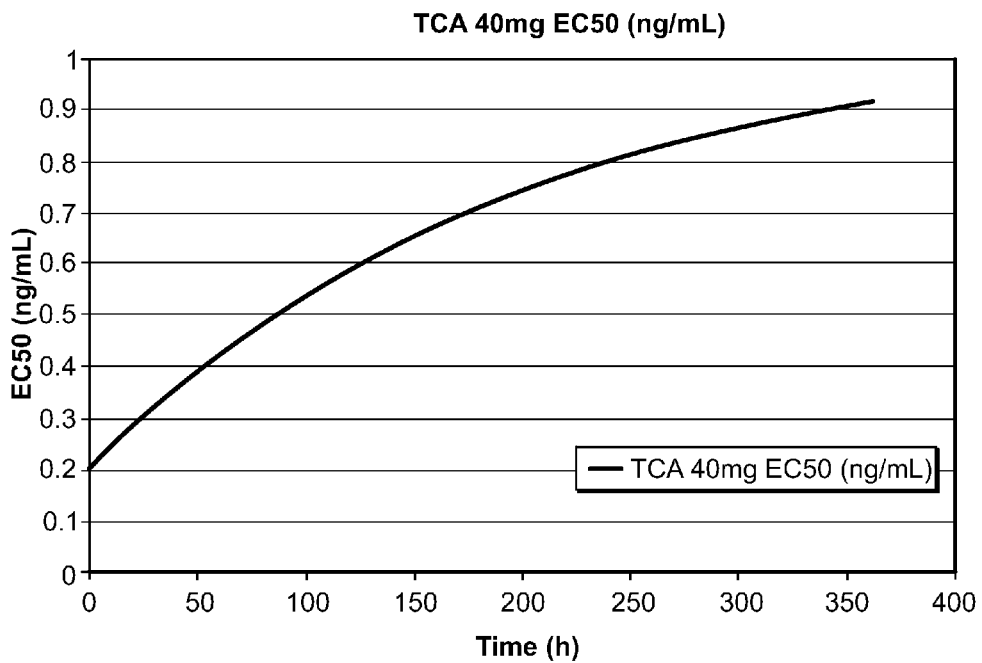
FIG. 2 is a graph depicting the change in sensitivity over time to suppression of endogenous cortisol production ($EC_{50}$ (ng/mL) vs. time) for triamcinolone acetonide 40 mg given by intra-articular administration.
Figure 3:
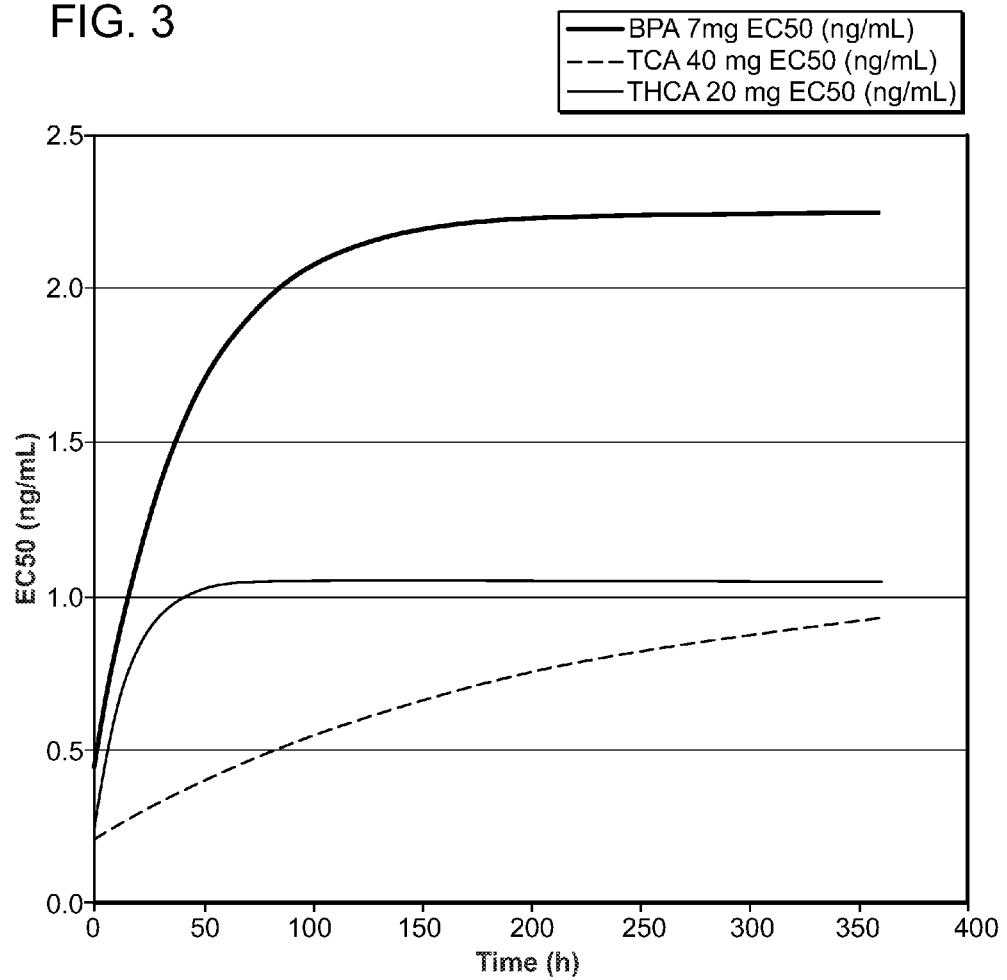
FIG. 3 is a graph depicting the change in sensitivity over time to suppression of endogenous cortisol production ($EC_{50}$ (ng/mL) vs. time) for various corticosteroids administered as a single, intra-articular injection in the listed dose.

Additional embodiments include doses during first and/or the second period of time selected to adjust for corticosteroid-specific (or corticosteroid- and potentially dose-specific) changes in the rate of change of sensitivity of the HPA axis to suppression that begin with initial exposure. For clinically effective corticosteroids, the rate of change of the sensitivity of the HPA axis to exogenous corticosteroids is both non-uniform and non-linear (FIG. 2). The rate and pattern of change in such sensitivity varies widely as a function of the particular corticosteroid that is selected (FIG. 3).

Finally, it is possible to usefully characterize the change in sensitivity vs. time mathematically as the (non-linear, exponential) "decay" of the sensitivity from the initial to final value, wherein the decay parameters (Table 1) has been determined from the data further described herein.

TABLE 1

HPA Axis Change-in-Sensitivity Decay-Parameter δ vs. Corticosteroid and Dose*

| Corticosteroid | Decay Parameter δ (time$^{-1}$) |
|---|---|
| Betamethasone Phosphate/Acetate (7 mg) | 0.024 |
| Triamcinolone Acetonide (40 mg) | 0.005 |
| Triamcinolone Hexacetonide (20 mg) | 0.070 |

*The inhibition of endogenous cortisol synthesis can be related to the exogenous corticosteroid concentration by the following equations:
1. $E = (E_{max} \cdot C^n)/[(EC_{50})^n + C^n]$ wherein E = effect, $E_{max}$ = maximal effect, C = concentration of exogenous corticosteroid, $EC_{50}$ = concentration at $\frac{1}{2}E_{max}$, and n = the Hill ("shape", or "slope") factor; and
2. $EC_{50-final} = EC_{50-initial} + [EC_{50-final} - EC_{50-initial}] \cdot [1 - e^{(-\delta \cdot time)}]$ Using this approach permits the determination of "δ", the parameter describing the exponential decay from the initial to the final $EC_{50}$. Minimization of least-squares differences was utilized to obtain the best-fit δ.

These new findings regarding the rate and pattern of change of sensitivity to inhibition and the lack of predictability of such rates and patterns on the basis of, for example, steroid potency, have significant implications for clinically appropriate dose-selection. Those skilled in the art will appreciate the importance of a changing sensitivity to HPA axis suppression and will also appreciate both the complexity and counterintuitive aspects of several of these new findings (Table 1).

As a result of these clinical findings, the dose range to achieve clinically useful analgesia, with minimal or controlled modulation of the HPA axis, at steady state concentrations of various corticosteroids has been determined (Table 2). In particular, it appears that the daily corticosteroid doses at steady state concentrations, are approximately 3- to 7-times greater than are predicted by prior art (Meibohm, 1999).

TABLE 2

Dose (mg/d), adjusted for individual intra-articular corticosteroid characteristics, for expected suppression of endogenous cortisol production at steady state.

| | Cortisol Inhibition (%) | | | | |
|---|---|---|---|---|---|
| Corticosteroid | 5% | 10% | 20% | 35% | 50% |
| betamethasone (mg/d) | 0.1 | 0.2 | 0.5 | 1.0 | 1.8 |
| budesonide (mg/d) | 0.1 | 0.2 | 0.6 | 1.2 | 2.2 |
| des-ciclesonide (mg/d) | 3.0 | 6.3 | 14.3 | 30.7 | 57.0 |
| dexamethasone (mg/d) | 0.1 | 0.2 | 0.4 | 0.9 | 1.6 |
| flunisonide (mg/d) | 0.3 | 0.5 | 1.2 | 2.6 | 4.8 |
| fluticasone (mg/d) | 0.1 | 0.1 | 0.3 | 0.6 | 1.1 |
| mometasone (mg/d) | 0.2 | 0.4 | 0.9 | 2.0 | 3.7 |
| methylprednisolone (mg/d) | 0.3 | 0.7 | 1.6 | 3.5 | 6.5 |
| prednisolone (mg/d) | 0.4 | 0.8 | 1.9 | 4.0 | 7.5 |
| triamcinolone acetonide (mg/d) | 0.2 | 0.4 | 0.8 | 1.7 | 3.2 |
| triamcinolone hexacetonide (mg/d) | 0.1 | 0.2 | 0.4 | 0.9 | 1.6 |

TABLE 2A

Total Dose Delivered (mg/month), adjusted for individual intra-articular corticosteroid characteristics, for expected suppression of endogenous cortisol production at steady state.

| | Cortisol Inhibition (%) | | | | |
|---|---|---|---|---|---|
| Corticosteroid | 5% | 10% | 20% | 35% | 50% |
| betamethasone | 3.0 | 6.0 | 15.0 | 30.0 | 54.0 |
| budesonide | 3.0 | 6.0 | 18.0 | 36.0 | 66.0 |
| des-ciclesonide | 90.0 | 189.0 | 429.0 | 921.0 | 1710.0 |
| dexamethasone | 3.0 | 6.0 | 12.0 | 27.0 | 48.0 |
| flunisonide | 9.0 | 15.0 | 36.0 | 78.0 | 144.0 |
| fluticasone | 3.0 | 3.0 | 9.0 | 18.0 | 33.0 |
| mometasone | 6.0 | 12.0 | 27.0 | 60.0 | 111.0 |
| methylprednisolone | 9.0 | 21.0 | 48.0 | 105.0 | 195.0 |
| prednisolone | 12.0 | 24.0 | 57.0 | 120.0 | 225.0 |
| triamcinolone acetonide | 6.0 | 12.0 | 24.0 | 51.0 | 96.0 |
| triamcinolone hexacetonide | 3.0 | 6.0 | 12.0 | 27.0 | 48.0 |

That higher doses of corticosteroids can be administered successfully by intra-articular injection, maximizing the likelihood of observing anti-inflammatory and analgesic responses while minimizing or eliminating adverse events from HPA axis suppression or otherwise excessive tissue exposure, is of profound clinical consequence for improving the treatment of patients with arthritis.

In addition, with these continuous daily doses of intra-articular corticosteroids, it is possible to determine the related systemic plasma level concentrations (Table 3) that will produce the target cortisol inhibition and not beyond, this while retaining clinically important anti-inflammatory and analgesic activity within the joint. These plasma concentrations were predicted on the basis of data from short term (i.e., less than 8 days) exposure to corticosteroids. With longer exposure to corticosteroids, the "decay" (i.e., decline) of the sensitivity to corticosteroids may continue resulting in values higher than those listed in Table 3. The levels calculated in Table 3 were purely hypothetical calculations based on human data with immediate release-level doses from the literature. With sustained release dosages, more drug may be able to be delivered without seeing an increased level of cortisol inhibition after the initial burst period. A given level of plasma concentration may actually provide less inhibition that would have been predicted or calculated using the human IR levels from the literature.

TABLE 3

Plasma corticosteroid concentrations associated with target levels of cortisol inhibition at steady state.

| | Corticosteroid Concentration in Plasma (ng/mL) associated with the Target Levels of Cortisol Inhibition (%) | | | | |
|---|---|---|---|---|---|
| Corticosteroid | 5% | 10% | 20% | 35% | 50% |
| betamethasone (ng/mL) | 0.33 | 0.70 | 1.57 | 3.38 | 6.27 |
| budesonide (ng/mL) | 0.60 | 1.27 | 2.85 | 6.14 | 11.40 |
| des-ciclesonide (ng/mL) | 0.55 | 1.16 | 2.61 | 5.63 | 10.45 |
| dexamethasone (ng/mL) | 0.21 | 0.44 | 1.00 | 2.15 | 3.99 |
| flunisonide (ng/mL) | 0.18 | 0.38 | 0.86 | 1.84 | 3.42 |
| fluticasone (ng/mL) | 0.04 | 0.08 | 0.19 | 0.41 | 0.76 |
| mometasone (ng/mL) | 0.15 | 0.32 | 0.71 | 1.54 | 2.85 |
| methylprednisolone (ng/mL) | 0.68 | 1.44 | 3.23 | 6.96 | 12.92 |
| prednisolone (ng/mL) | 1.64 | 3.46 | 7.79 | 16.79 | 31.16 |
| triamcinolone acetonide (ng/mL) | 0.19 | 0.40 | 0.90 | 1.95 | 3.61 |
| triamcinolone hexacetonide (ng/mL) | 0.10 | 0.21 | 0.48 | 1.02 | 1.90 |

The studies presented herein demonstrate for the first time the discovery of the time-course of changes in sensitivity of the HPA axis to exogenous corticosteroids. In addition, both the mean doses and mean plasma levels shown in Tables 2 and 3 above are those after steady state has been achieved, requiring approximately 4 to 24 days depending upon the corticosteroid in question. The companion post-dose but pre-steady-state transients for several corticosteroids have been described in FIGS. 2, 3, and 4A-4F. It is also important to note that the data suggest that the carefully controlled benefits from the intra-articular, sustained release of a corticosteroid of interest will persist as long as release continues.

In one preferred embodiment, a single component sustained release formulation releases a dose (in mg/day) that suppresses the HPA axis by no more than between 5-40% at steady state as shown in Table 2, more preferably no more than between 10-35% at steady state as shown in Table 2. These doses are therapeutically effective without adverse side effects.

In another preferred embodiment, a single component sustained release formulation releases a dose (in mg/day) that does not measurably suppress the HPA axis at steady state. These doses are therapeutically effective without adverse side effects.

In another embodiment where both an immediate release component and sustained release component of the formulation are present, immediate release dose would be as shown in Table 4 and the sustained release dose would be a dose (in mg/day) that suppresses the HPA axis by no more than between 5-40% as shown in Table 2, more preferably no more than between 10-35% as shown in Table 2. In addition, it is expected that sustained release doses described previously will follow immediate release doses as shown in Table 4.

TABLE 4

Immediate release relative doses (mg)

| Corticosteroid | Immediate Release Dose (mg) |
|---|---|
| betamethasone[1] | 5-20 |
| budesonide[2] | 7-28 |
| des-ciclesonide[2] | 177-713 |
| dexamethasone[2] | 5-20 |
| flunisonide[2] | 15-60 |
| fluticasone[2] | 3-12 |
| mometasone[2] | 11-44 |
| methylprednisolone[1] | 40-160 |
| prednisolone[1] | 25-100 |
| triamcinolone acetonide[1] | 10-40 |
| triamcinolone hexacetonide[1] | 10-40 |

[1]clinical doses
[2]calculated doses

Sustained Release Delivery Platforms

The manufacture of microparticles or methods of making biodegradable polymer microparticles are known in the art. Microparticles from any of the biodegradable polymers listed below can be made by, but not limited to, spray drying, solvent evaporation, phase separation, spray drying, fluidized bed coating or combinations thereof.

In certain embodiments of the invention, the microparticles are made from a biodegradable polymer that may include, without limitation, natural or synthetic biocompatible biodegradable materials. Natural polymers include, but are not limited to, proteins such as albumin, collagen, gelatin synthetic poly(aminoacids), and prolamines; glycosaminoglycans, such as hyaluronic acid and heparin; polysaccharides, such as alginates, chitosan, starch, and dextrans; and other naturally occurring or chemically modified biodegradable polymers. Synthetic biocompatible biodegradable materials include, but are not limited to the group comprising of, poly(lactide-co-glycolide) (PLGA), polylactide (PLA), polyglycolide (PG), polyhydroxybutyric acid, poly (trimethylene carbonate), polycaprolactone (PCL), polyvalerolactone, poly(alpha-hydroxy acids), poly(lactones), poly(amino-acids), poly(anhydrides), polyketals poly(arylates), poly(orthoesters), poly(orthocarbonates), poly(phosphoesters), poly(ester-co-amide), poly(lactide-co-urethane, polyethylene glycol (PEG), polyvinyl alcohol (PVA), PVA-g-PLGA, PEGT-PBT copolymer(polyactive), polyurethanes, polythioesters, methacrylates, poly(N-isopropylacrylamide), PEO-PPO-PEO (pluronics), PEO-PPO-PAA copolymers, and PLGA-PEO-PLGA blends and copolymers thereof, multi-block polymer configurations such as PLGA-PEG-PLGA, and any combinations thereof. These polymers may be used in making controlled release or sustained release compositions disclosed herein.

In a preferred embodiment, the microparticles are formed from poly(d,l-lactic-co-glycolic acid) (PLGA), which is commercially available from a number of sources. Biodegradable PLGA copolymers are available in a wide range of molecular weights and ratios of lactic to glycolic acid. If not purchased from a supplier, then the biodegradable PLGA copolymers may be prepared by the procedure set forth in U.S. Pat. No. 4,293,539 (Ludwig, et al.), the disclosure of which is hereby incorporated by reference in its entirety. Ludwig prepares such copolymers by condensation of lactic acid and glycolic acid in the presence of a readily removable polymerization catalyst (e.g., a strong acid ion-exchange resin such as Dowex HCR-W2-H). However, any suitable method known in the art of making the polymer can be used.

In the coacervation process, a suitable biodegradable polymer is dissolved in an organic solvent. Suitable organic solvents for the polymeric materials include, but are not limited to acetone, halogenated hydrocarbons such as chloroform and methylene chloride, aromatic hydrocarbons such as toluene, halogenated aromatic hydrocarbons such as chlorobenzene, and cyclic ethers such as dioxane. The organic solvent containing a suitable biodegradable polymer is then mixed with a non-solvent such as silicone based solvent. By mixing the miscible non-solvent in the organic solvent, the polymer precipitates out of solution in the form of liquid droplets. The liquid droplets are then mixed with another non-solvent, such as heptane or petroleum ether, to form the hardened microparticles. The microparticles are then collected and dried. Process parameters such as solvent and non-solvent selections, polymer/solvent ratio, temperatures, stirring speed and drying cycles are adjusted to achieve the desired particle size, surface smoothness, and narrow particle size distribution.

In the phase separation or phase inversion procedures entrap dispersed agents in the polymer to prepare microparticles. Phase separation is similar to coacervation of a biodegradable polymer. By addition of a nonsolvent such as petroleum ether, to the organic solvent containing a suitable biodegradable polymer, the polymer is precipitates from the organic solvent to form microparticles.

In the salting out process, a suitable biodegradable polymer is dissolved in an aqueous miscible organic solvent. Suitable water miscible organic solvents for the polymeric materials include, but are not limited to acetone, as acetone, acetonitrile, and tetrahydrofuran. The water miscible organic solvent containing a suitable biodegradable polymer is then mixed with an aqueous solution containing salt. Suitable salts include, but are not limited to electrolytes such as magnesium chloride, calcium chloride, or magnesium acetate and non-electrolytes such as sucrose. The polymer precipitates from the organic solvent to form microparticles, which are collected and dried. Process parameters such as solvent and salt selection, polymer/solvent ratio, temperatures, stirring speed and drying cycles are adjusted to achieve the desired particle size, surface smoothness, and narrow particle size distribution.

Alternatively, the microparticles may be prepared by the process of Ramstack et al., 1995, described in published international patent application WO 95/13799, the disclosure of which is incorporated herein in its entirety. The Ramstack et al. process essentially provides for a first phase, including an active agent and a polymer, and a second phase, that are pumped through a static mixer into a quench liquid to form microparticles containing the active agent. The first and second phases can optionally be substantially immiscible and the second phase is preferably free from solvents for the polymer and the active agent and includes an aqueous solution of an emulsifier.

In the spray drying process, a suitable biodegradable polymer is dissolved in an organic solvent and then sprayed through nozzles into a drying environment provided with sufficient elevated temperature and/or flowing air to effectively extract the solvent. Adding surfactants, such as sodium lauryl sulfate can improve the surface smoothness of the microparticles.

Alternatively, a suitable biodegradable polymer can be dissolved or dispersed in supercritical fluid, such as carbon dioxide. The polymer is either dissolved in a suitable organic solvent, such as methylene chloride, prior to mixing in a suitable supercritical fluid or directly mixed in the supercritical fluid and then sprayed through a nozzle. Process parameters such as spray rate, nozzle diameter, polymer/solvent ratio, and temperatures, are adjusted to achieve the desired particle size, surface smoothness, and narrow particle size distribution.

In a fluidized bed coating, the drug is dissolved in an organic solvent along with the polymer. The solution is then processed, e.g., through a Wurster air suspension coating apparatus to form the final microcapsule product.

The microparticles can be prepared in a size distribution range suitable for local infiltration or injection. The diameter and shape of the microparticles can be manipulated to modify the release characteristics. In addition, other particle shapes, such as, for example, cylindrical shapes, can also modify release rates of a sustained release corticosteroid by virtue of the increased ratio of surface area to mass inherent to such alternative geometrical shapes, relative to a spherical shape. The microparticles have a mass mean diameter ranging between about 0.5 to 500 microns. In a preferred embodiment, the microparticles have a mass mean diameter of between 10 to about 100 microns.

Biodegradable polymer microparticles that deliver sustained release corticosteroids may be suspended in suitable aqueous or non-aqueous carriers which may include, but is not limited to water, saline, pharmaceutically acceptable oils, low melting waxes, fats, lipids, liposomes and any other pharmaceutically acceptable substance that is lipophilic, substantially insoluble in water, and is biodegradable and/or eliminatable by natural processes of a patient's body. Oils of plants such as vegetables and seeds are included. Examples include oils made from corn, sesame, cannoli, soybean, castor, peanut, olive, arachis, maize, almond, flax, safflower, sunflower, rape, coconut, palm, babassu, and cottonseed oil; waxes such as carnoba wax, beeswax, and tallow; fats such as triglycerides, lipids such as fatty acids and esters, and liposomes such as red cell ghosts and phospholipid layers.

Corticosteroid Loading of and Release from Biodegradable Polymer Microparticles

When an intra-articularly delivered corticosteroid is incorporated into a biodegradable polymer for sustained release into a joint at a dosage that does not suppress the HPA axis, preferred loadings of said corticosteroid are from about 5% to about 40% (w/w) of the polymer, preferably about 5% to about 30%, more preferably about 5% to about 28% of the polymer.

As the biodegradable polymers undergo gradual bio-erosion within the joint, the corticosteroid is released to the inflammatory site. The pharmacokinetic release profile of the corticosteroid by the biodegradable polymer may be first order, zero order, bi- or multi-phasic, to provide desired treatment of inflammatory related pain. In any pharmacokinetic event, the bio-erosion of the polymer and subsequent release of the corticosteroid may result in a controlled release of a corticosteroid from the polymer matrix. The rate of release at dosages that do not suppress the HPA axis are described above.

Excipients

The release rate of the corticosteroid from a biodegradable polymer matrix can be modulated or stabilized by adding a pharmaceutically acceptable excipient to the formulation. An excipient may include any useful ingredient added to the biodegradable polymer depot that is not a corticosteroid or a biodegradable polymer. Pharmaceutically acceptable excipients may include without limitation lactose, dextrose, sucrose, sorbitol, mannitol, starches, gum acacia, calcium phosphate, alginates, tragacanth, gelatin, calcium silicate, microcrystalline cellulose, PEG, polysorbate 20, polysorbate 80, polyvinylpyrrolidone, cellulose, water, saline, syrup, methyl cellulose, and carboxymethyl cellulose. An excipient for modulating the release rate of a corticosteroid from the biodegradable drug depot may also include without limitation pore formers, pH modifiers, reducing agents, antioxidants, and free radical scavengers.

Delivery of Corticosteroid Microparticles

Parenteral administration of formulations of the invention can be effected by intra-articular injection or other injection using a needle. To inject the microparticles into a joint, needles having a gauge of about 14-28 gauge are suitable. It will be appreciated by those skilled in the art that formulations of the present invention may be delivered to a treatment site by other conventional methods, including catheters, infusion pumps, pens devices, injection guns and the like.

All references, patents, patent applications or other documents cited are hereby incorporated by reference.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Sustained-Release Betamethasone or Triamcinolone Acetonide Microparticles

In one embodiment, the microparticle formulation contains a copolymer of DL-lactide (or L-lactide) and glycolide in a 45:55 molar ratio (up to 75:25 molar ratio) with an inherent viscosity ranging from 0.15 to 0.60 dL/g with either an ester or acid end group plus either the corticosteroid betamethasone or triamcinolone acetonide. If betamethasone is used, then the betamethasone is in the form of either betamethasone acetate, betamethasone diprionate or a combination thereof. The total amount of betamethasone or triamcinolone acetonide incorporated into the microparticle ranges from 10% to 30% (w/w). The microparticles are formulated to mean mass range in size from 10 to 100 microns. The population of microparticles is formulated to be delivered through a 19 gauge or higher needle. Additional excipients may be added such as, but not limited to, carboxymethylcellulose sodium, mannitol, polysorbate-80, sodium phosphate, sodium chloride, polyethylene glycol to achieve isotonicity and promote syringeability. If betamethasone is used, then the betamethasone incorporated into the microparticle population provides an initial release (burst) of about 5-20 mg of drug over a period of 1 to 12 hours, followed by a steady state release of drug at a rate of about 0.1 to 1.0 mg/day over a period of 14 to 90 days. If triamcinolone acetonide is used, then the drug incorporated into the microparticle population provides an initial release (burst) of about 10-40 mg of drug over a period of 1 to 12 hours, followed by a steady state release of drug at a rate of about 0.2 to 1.7 mg/day over a period of 14 to 90 days.

Example 2

Sustained-Release Betamethasone or Triamcinolone Acetonide Microparticles with an Immediate Release Form In another embodiment, the microparticle formulation of Example 1 is further admixed with an immediate release betamethasone or triamcinolone acetonide component, such as a betamethasone or triamcinolone acetonide containing solution. If betamethasone is used, then the betamethasone in the immediate release component is in the form of either betamethasone acetate, betamethasone diproprionate or a combination thereof. If betamethasone is used, then the immediate release component provides an initial release of a total of about 5 to 20 mg of betamethasone over the first 1-10 days, while the sustained release component releases betamethasone at a rate of about 0.1 to 1.0 mg/day over the first 14 to 90 days following administration. If triamcinolone acetonide is used, then the immediate release component provides an initial release of a total of 10 to 40 mg of drug over the first 1-10 days, while the sustained release component releases drug at a rate of about 0.2 to 1.7 mg/day over the first 14 to 90 days following administration.

Example 3

Determination of Time-Variance in HPA Axis Sensitivity

Figure 4C:
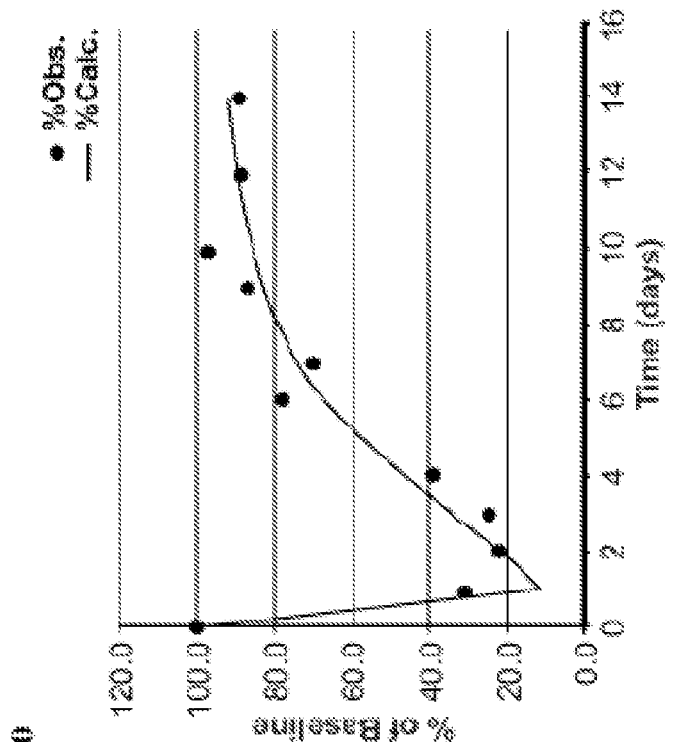
Figure 4D:
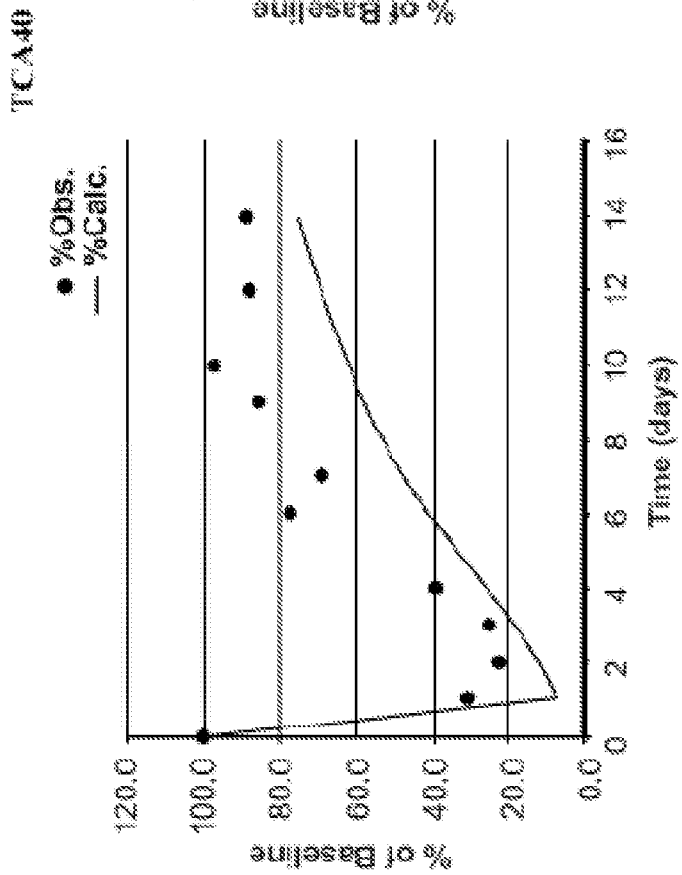
Figure 4E:
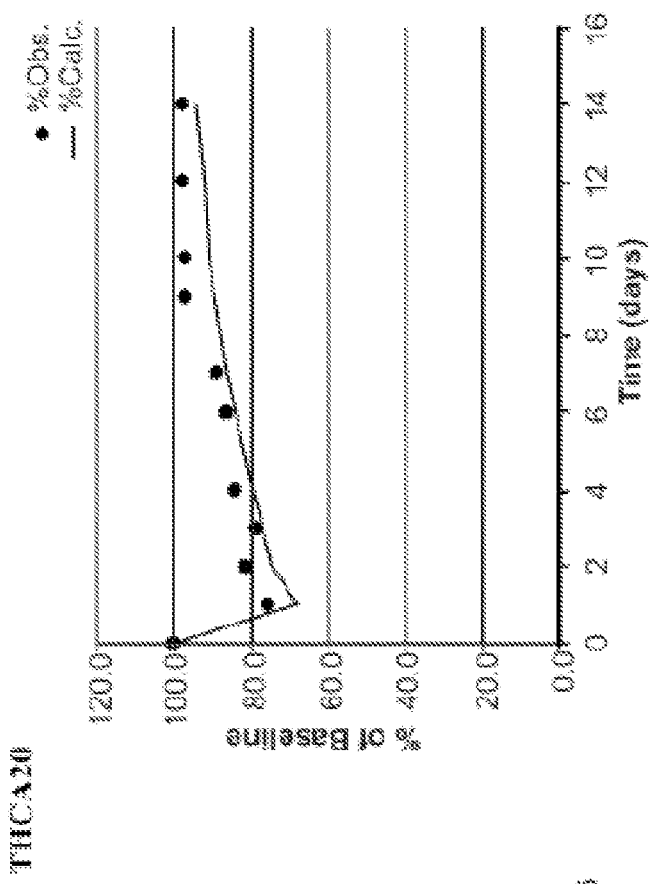
Figure 4F:
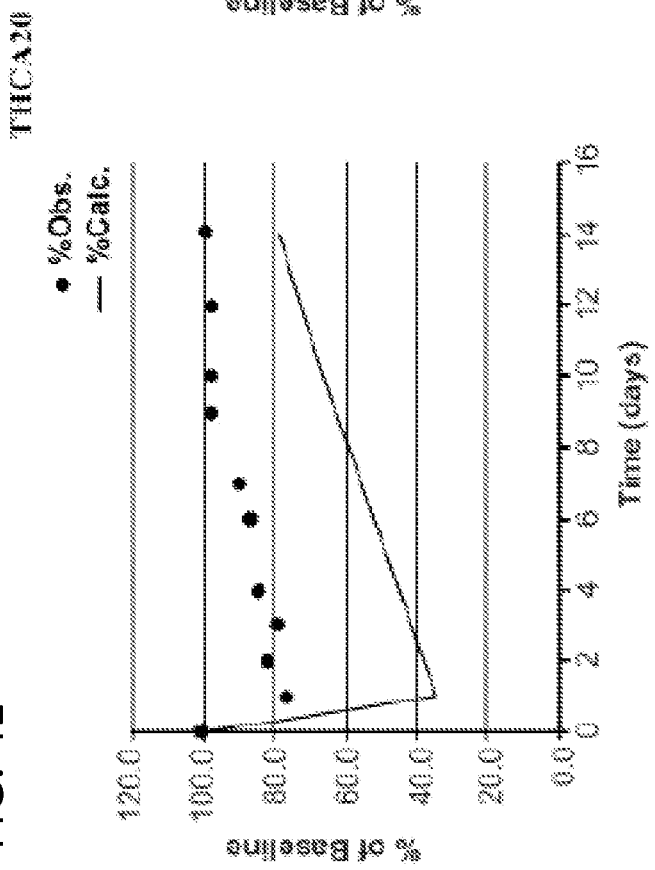

Adult volunteers (N=4 to 9 per group) give appropriate informed consent. Each individual in each group receives a single intra-articular administration of an exogenous corticosteroid (triamcinolone acetonide 40 mg; triamcinolone hexacetonide 20; betamethasone 7 mg (disodium phosphate 4 mg/acetate 3 mg). Blood samples for measurement of corticosteroid concentrations and/or cortisol concentrations are drawn at 8 AM at baseline and on days 1, 7, 9, 10, 12, 14, 18, and 21. The extent of suppression of endogenous cortisol was measured in each subject in each group. The extent of cortisol suppression predicted by previously published models (Meibohm, 1999) was determined and compared to observations (FIGS. 4A, 4C, and 4E). The change (decrease) in HPA axis sensitivity vs. time is then determined on a day-by-day and final basis (FIGS. 4B, 4D, and 4F), permitting determination of the correct steady-state intra-articular doses of corticosteroid to achieve, or limit, HPA axis suppression to the desired level.

Example 4

Preparation of Triamcinolone Acetonide Microparticles by Spinning Disk

A pharmaceutical depot was prepared comprised of the corticosteroid, triamcinolone acetonide (TCA, 9α-Fluoro-11β,16α,17α,21-tetrahydroxy-1,4-pregnadiene-3,20-dione 16,17-acetonide; 9α-Fluoro-16α-hydroxyprednisolone 16α, 17α-acetonide) incorporated into PLGA microparticles.

In one suitable thirty day formulation, 250 mg of triamcinolone acetonide and 750 mg of PLGA (lactide:glycolide molar ratio of 75:25, inherent viscosity of 0.4 dL/g and molecular weight of 54 kDa) were dispersed in 14.25 grams of dichloromethane. The dispersion was atomized into micro-droplets by adding the dispersion to the feed well of a rotating disk, rotating at a speed of approximately 3300 rpm inside a temperature controlled chamber maintained at 38-45° C. The solvent was evaporated to produce solid microparticles. The microparticles were collected using a cyclone separator and, subsequently, sieved through a 150 µm sieve.

Particle size of the TCA incorporated microparticles was determined using laser diffraction (Malvern Mastersizer 2000) by dispersing a 250 mg aliquot in water, with the refractive index (RI) for water and PLGA, set at 1.33 and 1.46 respectively. Sonication was maintained as the sample was stirred at 2500 rpm and measurements taken every 15 seconds, with the average of three measurements reported. 10 mg of TCA containing microparticles were added to 10 mL of dimethylsulfoxide (DMSO), mixed until dissolved and an aliquot analyzed by HPLC to determine the microparticle drug load. Another 4 mg of TCA containing microparticles were suspended in 20 mL of phosphate buffered saline (PBS) containing 0.5% sodium dodecyl sulfate (SDS) maintained at 37° C. 0.5 mL of the media was removed at regular intervals, replaced at each interval with an equivalent amount of fresh media to maintain a constant volume, and analyzed by HPLC to determine microparticle in vitro release. Analysis by HPLC was conducted using a C18 (Waters Nova-Pack C-18, 3.9×150 mm) and 35% acetonitrile mobile phase at 1 ml/min flow rate with UV detection at 240 nm. The results are shown in Table 5.

TABLE 5

Analytical Results for 25% Triamcinolone Acetonide PLGA 75:25 Microparticles

| PLGA (lactide:glycolide molar ratio ratio/inherent viscosity/ molecular weight/target % TCA | Drug load (% TCA by weight) | Incorporation efficiency (%) | Particle size (Dv, µm) | In vitro release (%) |
| --- | --- | --- | --- | --- |
| 75:25 carboxylic acid end-capped 0.4 dL/g 54 kDa 25% | 24 | 96 | D0.1: 32 µm D0.5: 49 µm D0.9: 73 µm | 0.2 day: 5.1 1 day: 13.5 3 day: 29.6 7 day: 52.6 14 day 70.9 21 day: 76.4 28 day: 79.1 |

Figure 5:
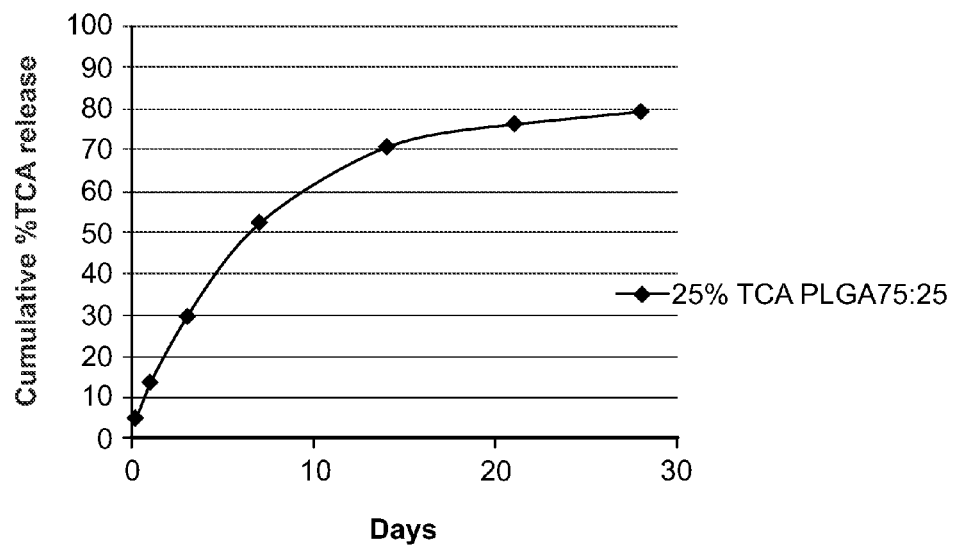
FIG. 5 is a graph depicting the cumulative percent release of a nominal 25% (w/w) triamcinolone acetonide in PLGA 75:25 microparticles.

The in vitro cumulative release profile is graphed in FIG. 5.

Figure 6:
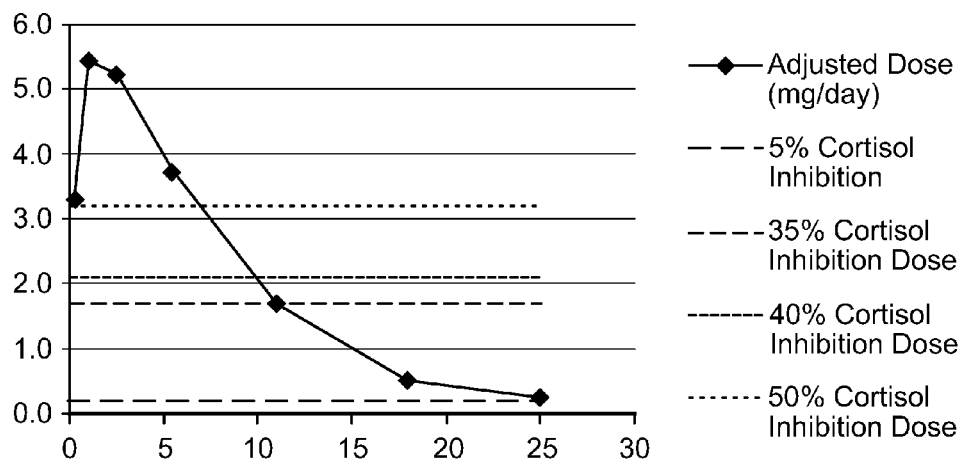
FIG. 6 is a graph depicting the calculated human dose to achieve transient cortisol suppression and within 14 days achieve less than 35% cortisol suppression using nominal 25% TCA PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 7:
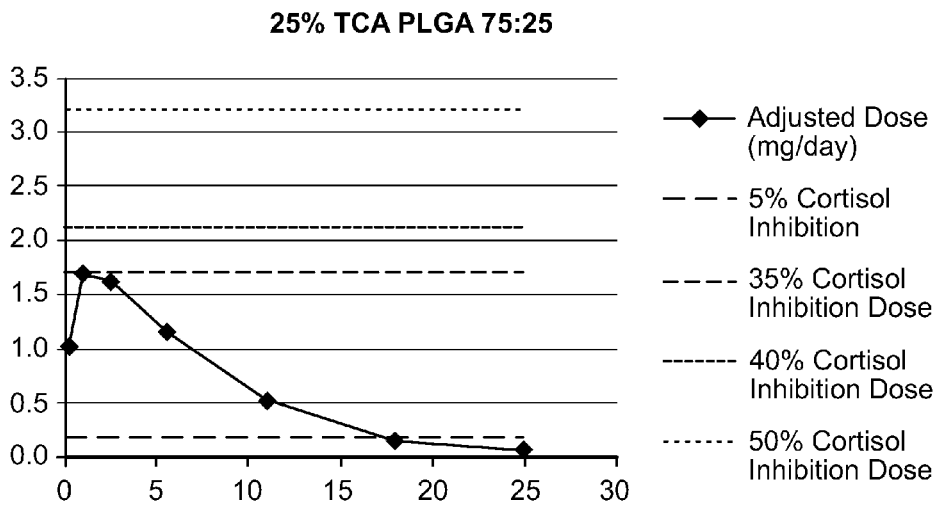
FIG. 7 is a graph depicting calculated human dose that does not affect the HPA axis, less than 35% cortisol suppression using nominal 25% TCA PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.

In one iteration of these data, the amount of TCA released per day was calculated based on a human dose, as exemplified in Table 2, that would achieve a transient suppression of endogenous cortisol (greater than 50%) and, within 14 days, achieve cortisol suppression of endogenous cortisol of less than 35% as shown in FIG. 6. In a second iteration of these data, the amount of triamcinolone acetonide released per day was calculated based on a human dose, as exemplified in Table 2 that would not suppress the HPA axis, i.e. endogenous cortisol suppression never exceeding 35% as shown in FIG. 7. These calculated doses equal 376 mg of microparticles containing 94 mg of TCA and 80 mg of microparticles containing 20 mg of TCA, respectively.

Figure 8:
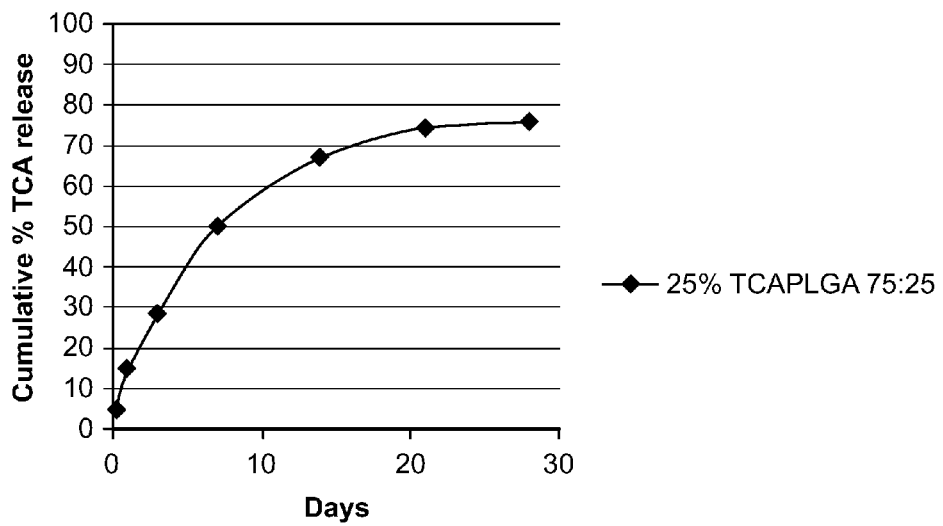
FIG. 8 is a graph depicting cumulative percent release of a second preparation of nominal 25% triamcinolone acetonide in PLGA 75:25 microparticles using an alternate preparation.
Figure 9:
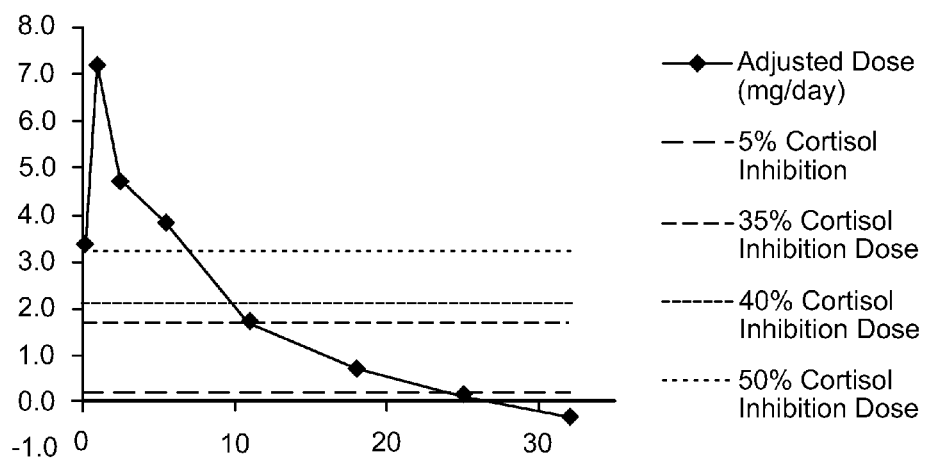
FIG. 9 is a graph depicting calculated human dose to achieve transient cortisol suppression and within 14 days achieve less than 35% cortisol suppression using a second preparation of nominal 25% TCA PLGA 75:25 microparticles made by an alternate preparation. The dotted lines represent, from top to bottom of the graph, 50% cortisol inhibition dose, 40% cortisol inhibition dose, 35% cortisol inhibition dose and 5% cortisol inhibition dose.
Figure 10:
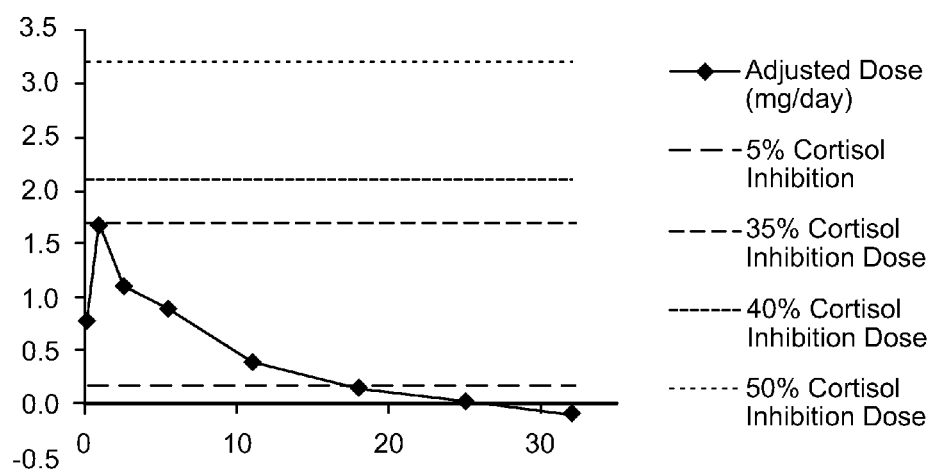
FIG. 10 is a graph depicting: calculated human dose that does not affect the HPA axis, less than 35% cortisol suppression using a second preparation of nominal 25% TCA PLGA 75:25 microparticles made by an alternate preparation. The dotted lines represent, from top to bottom of the graph, 50% cortisol inhibition dose, 40% cortisol inhibition dose, 35% cortisol inhibition dose and 5% cortisol inhibition dose.

In a second preparation of the same formulation, analyzed and in vitro release plotted in the same manner, the results are equivalent as shown in Table 6, and FIGS. 8, 9 and 10. The calculated human dose, as exemplified in Table 2 that would achieve a transient suppression of endogenous cortisol (greater than 50%) and, within 14 days, achieve cortisol suppression of endogenous cortisol of less than 35% equals 280 mg of microparticles containing 70 mg of TCA. The calculated human dose, as exemplified in Table 2 that would not suppress the HPA axis, i.e. endogenous cortisol suppression never exceeding 35% equals 68 mg of microparticles containing 17 mg of TCA.

TABLE 6

Analytical Results for Alternate Preparation of a Nominal 25% Triamcinolone Acetonide PLGA 75:25 Microparticles

| PLGA (lactide:glycolide molar ratio ratio/inherent viscosity/ molecular weight/target % TCA | Drug load (% TCA by weight) | Incorporation efficiency (%) | Particle size (Dv, μm) | In vitro release (%) |
|---|---|---|---|---|
| 75:25 carboxylic acid end-capped 0.4 dL/g 54 kDa 25% | 27.5 | 110 | D0.1: 30.9 μm D0.5: 48.2 μm D0.9: 71.0 μm | 0.2 day: 4.8 1 day: 15 3 day: 28.5 7 day: 50.2 14 day 67.1 21 day: 74.2 28 day: 75.7 |

Influence of PEG on PLGA 75:25 Formulations: In other suitable formulations, polyethylene glycol was added to the PLGA 75:25 polymers while keeping the target amount of triamcinolone acetonide constant. PEG/PLGA blends are known to allow for more complete and faster release of pharmaceutical agents incorporated into microparticles than PLGA alone (Cleek et al. "Microparticles of poly(DL-lactic-coglycolic acid)/poly(ethylene glycol) blends for controlled drug delivery." *J Control Release* 48 (1997): 259-268; Morlock, et al. "Erythropoietin loaded microspheres prepared from biodegradable LPLG-PEO-LPLG triblock copolymers: protein stabilization and in-vitro release properties." *J Control Release*, 56 (1-3) (1998): 105-15; Yeh, "The stability of insulin in biodegradable microparticles based on blends of lactide polymers and polyethylene glycol." *J Microencapsul*, 17 (6) (2000): 743-56).

In one iteration, 250 mg of triamcinolone acetonide, 50 mg of polyethylene glycol (PEG 1450) and 700 mg of PLGA (lactide:glycolide molar ratio of 75:25, inherent viscosity of 0.4 dL/g and molecular weight of 54 kDa) were dispersed in 14 grams of dichloromethane. In another iteration, 250 mg of triamcinolone acetonide, 100 mg of polyethylene glycol (PEG 3350) and 650 mg of PLGA (lactide:glycolide molar ratio of 75:25, inherent viscosity of 0.4 dL/g and molecular weight of 54 kDa) were dispersed in 13 grams of dichloromethane. The dispersions were atomized into micro-droplets by adding the dispersion to the feed well of a rotating disk, rotating at a speed of approximately 3300 rpm inside a temperature controlled chamber maintained at 38-45° C. The solvent was evaporated to produce solid microparticles. The microparticles were collected using a cyclone separator and, subsequently, sieved through a 150 μm sieve.

The microparticles were analyzed as described above and the data is shown in Table 7.

TABLE 7

Analytical Results of Nominal 25% Triamcinolone Acetonide PLGA 75:25 Microparticles containing Polyethylene Glycol (PEG) Additive

| PLGA (lactide:glycolide molar ratio ratio/inherent viscosity/ molecular weight/target % TCA/% PEG | Drug load (% TCA by weight) | Incorporation efficiency (%) | Particle size (Dv, μm) | In vitro release (%) |
|---|---|---|---|---|
| 75:25 carboxylic acid end-capped 0.4 dL/g 54 kDa 25% 5% PEG 1450 | 29.4 | 118 | D0.1: 36.2 μm D0.5: 59.0 μm D0.9: 95.5 μm | 0.2 day: 3.6 1 day: 13.8 3 day: 30.1 7 day: 49.5 14 day 65.5 21 day: 74.0 28 day: 78.5 |
| 75:25 carboxylic acid end-capped 0.4 dL/g 54 kDa 25% 10% PEG 3350 | 24.5 | 98 | D0.1: 32.0 μm D0.5: 52.4 μm D0.9: 79.0 μm | 0.2 day: 4.1 1 day: 11.7 3 day: 24.5 7 day: 40.8 14 day: 55.8 21 day: 63.7 28 day: 69.5 |

Figure 11:
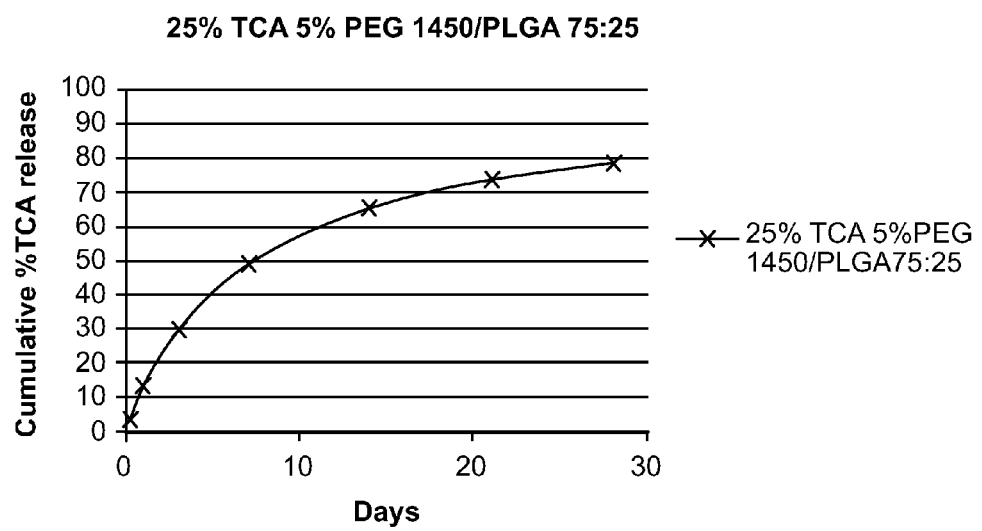
FIG. 11 is a graph depicting cumulative percent release of nominal 25% triamcinolone acetonide in 5% PEG 1450/PLGA 75:25 microparticles.
Figure 12:
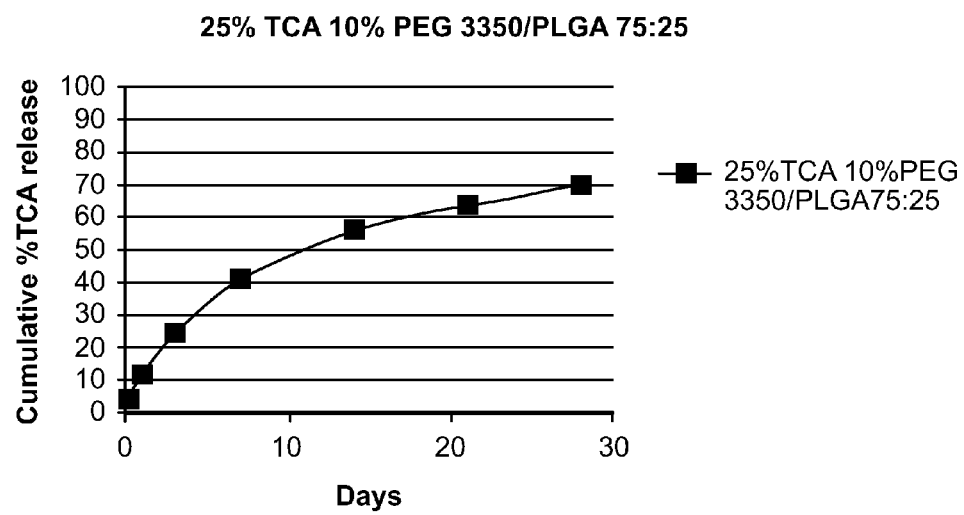
FIG. 12 is a graph depicting cumulative percent release of nominal 25% triamcinolone acetonide in 10% PEG 3350/PLGA 75:25 microparticles.
Figure 13:
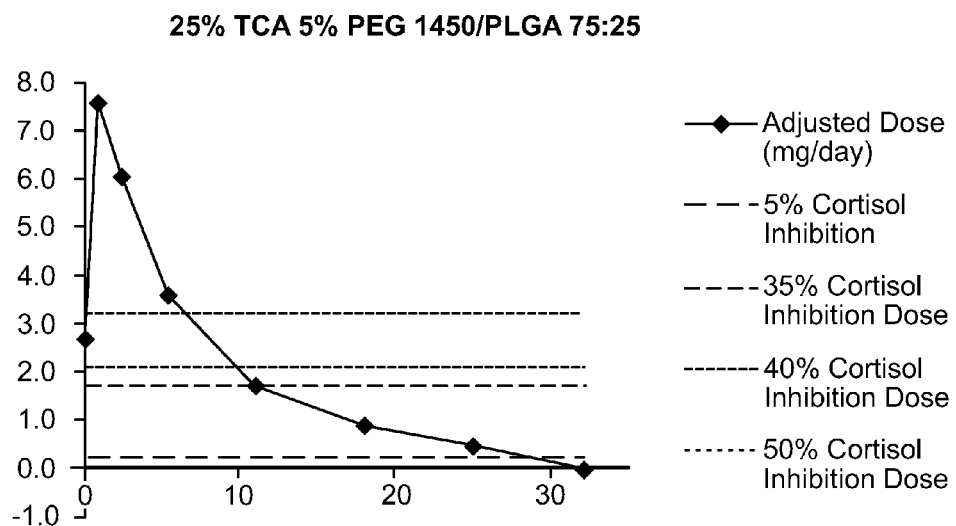
FIG. 13 is a graph depicting calculated human dose to achieve transient cortisol suppression and within 14 days achieve less than 35% cortisol suppression using nominal 25% TCA 5% PEG 1450/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 14:
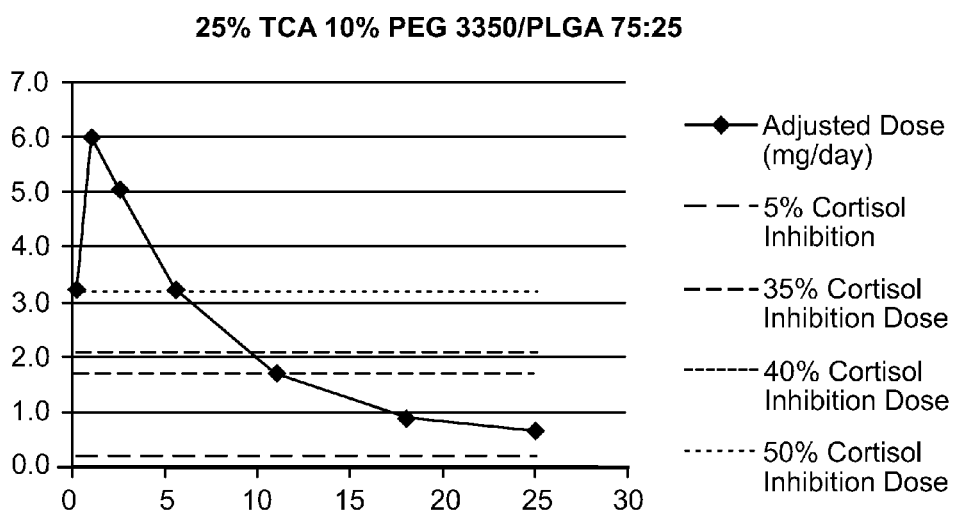
FIG. 14 is a graph depicting calculated human dose to achieve transient cortisol suppression and within 14 days achieve less than 35% cortisol suppression using nominal 25% TCA 10% PEG 3350/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 15:
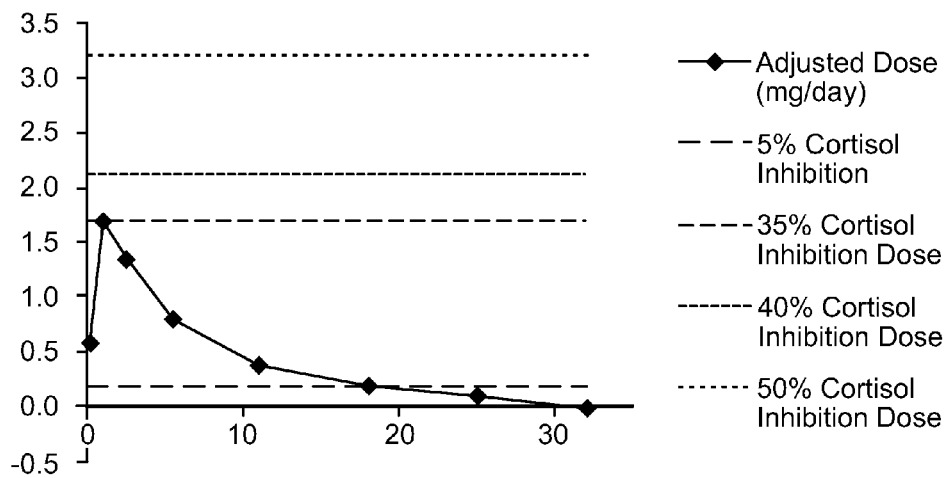
FIG. 15 is a graph depicting calculated human dose that does not affect the HPA axis, less than 35% cortisol suppression using nominal 25% TCA 5% PEG 1450/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 16:
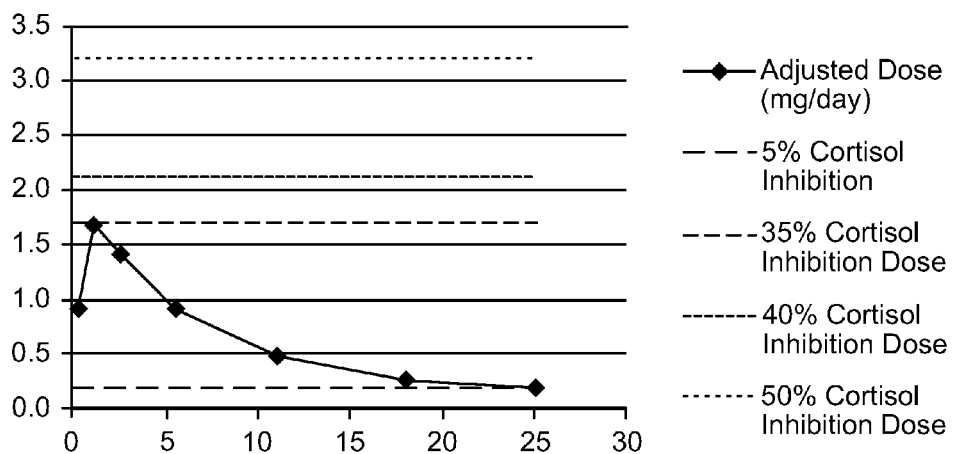
FIG. 16 is a graph depicting calculated human dose that does not affect the HPA axis, less than 35% cortisol suppression using nominal 25% TCA 10% PEG 3350/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.

The in vitro cumulative release profile is graphed in FIG. 11 and FIG. 12. PEG did not seem to enhance the release of the TCA in either formulation, as would be expected. In fact, at higher percentages of PEG, albeit a different molecular weight (higher percentages of PEG 1350 were unmanageable due to the agglomeration of microparticles), the release rate was slower.

In one iteration of these in vitro release data, the amount of TCA released per day was calculated based on a human dose, as exemplified in Table 2, that would achieve a temporary suppression of endogenous cortisol (greater than 50%) and, within 14 days, achieve cortisol suppression of endogenous cortisol of less than 35% as shown in FIG. 13 and FIG. 14. These calculated doses equal 296 mg of microparticles containing 74 mg of TCA and 316 mg of microparticles containing 79 mg of TCA, respectively. In a second iteration of these data, the amount of triamcinolone acetonide released per day was calculated based on a human dose, as exemplified in Table 2 that would not suppress the HPA axis, i.e. endogenous cortisol suppression never exceeding 35% as shown in FIGS. 15 and 16. These calculated doses equal 68 mg of microparticles containing 17 mg of TCA and 88 mg of microparticles containing 22 mg of TCA, respectively.

Other TCA containing formulations were tried with PEG and PLGA 75:25 without success. A PLGA microparticle formulation containing 25% TCA and 25% PEG 1450 agglomerated during manufacture and storage. Another PLGA formulation containing 40% TCA and 15% PEG 1450 gave similar results to the microparticles containing 40% TCA and no PEG.

Influence of Triamcinolone Acetonide Content in PLGA 75:25 Microparticles:

Triamcinolone acetonide containing microparticle depots were prepared and analyzed, as described above, with the exception of using 100 mg, 150 mg, 200 mg and 400 mg triamcinolone acetonide and adding to a 5% PLGA dichloromethane solution. The physical characteristics of these formulations are shown in Table 8.

TABLE 8

Analytical Results of PLGA 75:25 Microparticles containing varying amounts of Triamcinolone Acetonide

| PLGA (lactide:glycolide molar ratio ratio/inherent viscosity/ molecular weight/target % TCA | Drug load (% TCA by weight) | Incorporation efficiency (%) | Particle size (Dv, µm) | In vitro release (%) |
|---|---|---|---|---|
| 75:25 carboxylic acid end-capped 0.4 dL/g 54 kDa 40% | 43.4 | 109 | D0.1: 40.7 µm<br>D0.5: 70.7 µm<br>D0.9: 167 µm | 0.2 day: 6.6<br>1 day: 24.2<br>3 day: 53.8<br>7 day: 82.5<br>14 day 89.4<br>21 day: 89.6<br>28 day: 87.5 |
| 75:25 carboxylic acid end-capped 0.4 dL/g 54 kDa 20% | 20.2 | 101 | D0.1: 28.7 µm<br>D0.5: 45.2 µm<br>D0.9: 70.5 µm | 0.2 day: 5.3<br>1 day: 13.5<br>3 day: 23.7<br>7 day: 35.3<br>14 day 44.4<br>21 day: 48.1<br>28 day: 50.6 |
| 75:25 carboxylic acid end-capped 0.4 dL/g 54 kDa 15% | 15.9 | 106 | D0.1: 30.7 µm<br>D0.5: 47.8 µm<br>D0.9: 74.8 µm | 0.2 day: 3.9<br>1 day: 9.0<br>3 day: 14.2<br>7 day: 19.3<br>14 day 22.7<br>21 day: 24.6<br>28 day: 27.6 |
| 75:25 carboxylic acid end-capped 0.4 dL/g 54 kDa 10% | 11.7 | 117 | D0.1: 31.0 µm<br>D0.5: 57.9 µm<br>D0.9: 118 µm | 0.2 day: 2.3<br>1 day: 4.4<br>3 day: 5.9<br>7 day: 7.5<br>14 day 9.9<br>21 day: 11.7<br>28 day: 15.8 |

Figure 17:
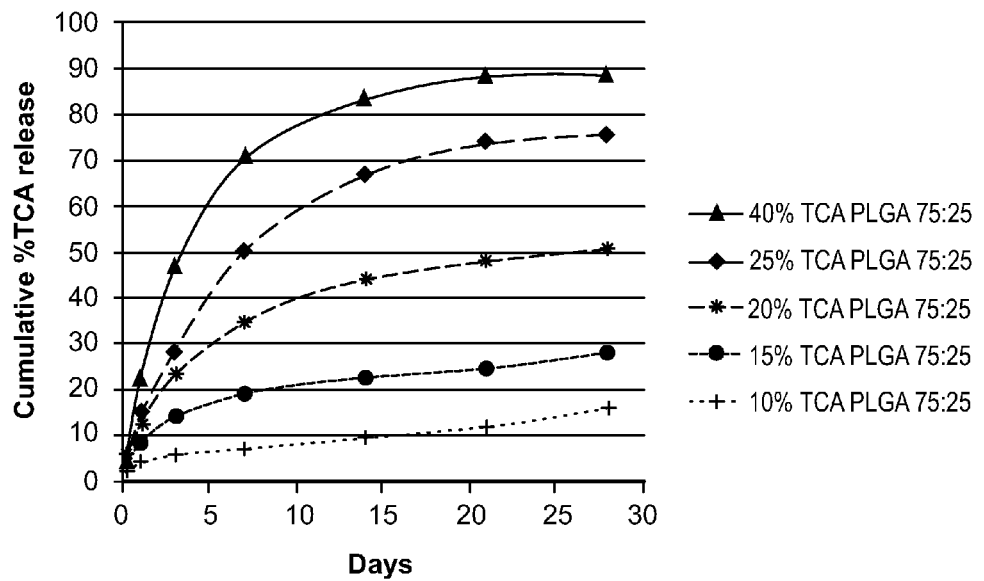
FIG. 17 is a graph depicting cumulative percent triamcinolone acetonide release of nominal 40%, 25% 20%, 15% and 10% TCA containing PLGA 75:25 microparticles.

The in vitro cumulative release profiles for these four other TCA containing PLGA 75:25 microparticle depots are graphed in FIG. 17, along with the preferred formulation (25% TCA). The tabulated data and graph show the impact of the percent TCA incorporated in the PLGA microparticles on the in vitro release profile. The 10%, 15% and 20% TCA containing PLGA microparticles exhibit a slower release profile, with a significant less cumulative release over 28 days, less than 20%, 30% and 55% respectively, than the 25% TCA PLGA depot exemplified in Example 4. The 40% TCA containing depot exhibits a faster release profile, with greater than 80% of the triamcinolone released by day 7 with a similar total cumulative release, than the 25% TCA PLGA depot exemplified in Example 4.

Influence of Molecular Weight on TCA PLGA 75:25 Microparticle Formulations: In another microparticle formulation, triamcinolone acetonide was incorporated in PLGA of the same lactide to glycolide molar ratio as cited in Example 4 but of a lower molecular weight. Low molecular weight PLGA is known to allow for more complete and faster release of pharmaceutical agents incorporated into microparticles than their higher molecular weight counterparts. (Anderson et al. "Biodegradation and biocompatibility of PLA and PLGA microspheres." *Advanced Drug Delivery Reviews* 28 (1997): 5-24; Bouissou et al., "Poly(lactic-co-glycolicacid) Microspheres." *Polymer in Drug Delivery* (2006): Chapter 7).

250 mg of triamcinolone acetonide and 750 mg of PLGA (lactide:glycolide molar ratio of 75:25, inherent viscosity of 0.27 dL/g and molecular weight of 29 kDa) were dispersed in 14.25 grams of dichloromethane. The dispersion was atomized into micro-droplets by adding the dispersion to the feed well of a rotating disk, rotating at a speed of approximately 3300 rpm inside a temperature controlled chamber maintained at 38-45° C. The solvent was evaporated to produce solid microparticles. The microparticles were collected using a cyclone separator and, subsequently, sieved through a 150 µm sieve.

Particle size of the TCA incorporated microparticles was determined using laser diffraction (Malvern Mastersizer 2000) by dispersing a 250 mg aliquot in water, with the refractive index (RI) for water and PLGA, set at 1.33 and 1.46 respectively. Sonication was maintained as the sample was stirred at 2500 rpm and measurements taken every 15 seconds, with the average of three measurements reported. 10 mg of TCA containing microparticles were added to 10 mL of dimethylsulfoxide (DMSO), mixed until dissolved and an aliquot analyzed by HPLC to determine the microparticle drug load. Another 4 mg of TCA containing microparticles were suspended in 20 mL of phosphate buffered saline (PBS) containing 0.5% sodium dodecyl sulfate (SDS) maintained at 37° C. 0.5 mL of the media was removed at regular intervals, replaced at each interval with an equivalent amount of fresh media to maintain a constant volume, and analyzed by HPLC to determine microparticle in vitro release. Analysis by HPLC was conducted using a C18 (Waters Nova-Pack C-18, 3.9×150 mm) and 35% acetonitrile mobile phase at 1 ml/min flow rate with UV detection at 240 nm. The results are shown in Table 9.

TABLE 9

Analytical Results of a Nominal 25% Triamcinolone Acetonide PLGA 75:25 (29 kDa) Microparticles

| PLGA (lactide:glycolide molar ratio ratio/inherent viscosity/ molecular weight/target % TCA/% PEG | Drug load (% TCA by weight) | Incorporation efficiency (%) | Particle size (Dv, µm) | In vitro release (%) |
|---|---|---|---|---|
| 75:25 carboxylic acid end-capped 0.27 dL/g 29 kDa 25% | 29.4 | 118 | D0.1: 34.1 µm<br>D0.5: 56.5 µm<br>D0.9: 95.2 µm | 0.2 day: 4.0<br>1 day: 11.3<br>3 day: 22.5<br>7 day: 35.9<br>14 day: 48.3<br>21 day: 53.4<br>28 day: 56.5 |

Figure 18:
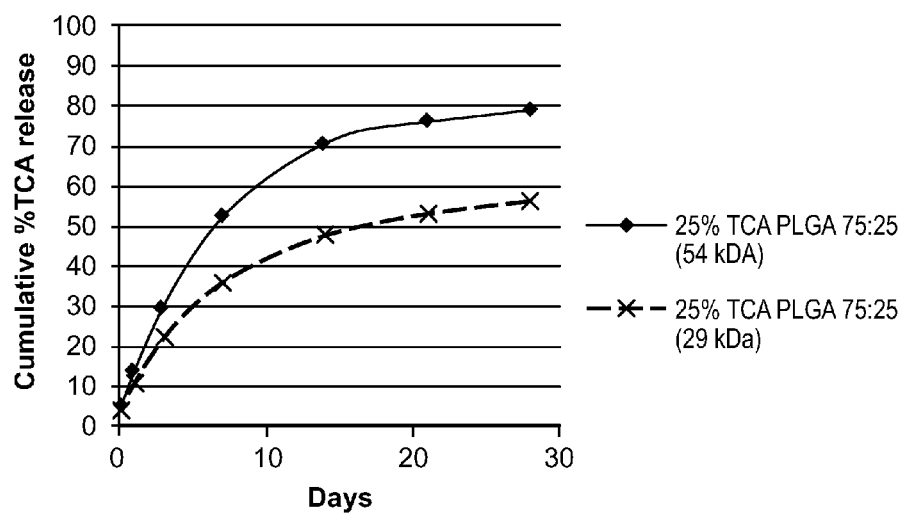
FIG. 18 is a graph depicting cumulative percent release of nominal 25% TCA PLGA 75:25 (29 kDa) and PLGA 75:25 (54 kDa) containing microparticles.

In vitro cumulative release data is graphed in FIG. 18, along with the preferred formulation using a higher molecular PLGA 75:25. The use of lower molecular weight PLGA (29 kDa) did not improve the release of the triamcinolone acetonide from the microparticles as expected, in fact the rate of release decreased and the release was incomplete as compared to higher molecular weight PLGA (PLGA, 54 kDa).

In another formulation of low molecular weight PLGA 75:25 (29 kDa), polyethylene glycol, 10% PEG 3350, was added while maintaining the same amount of triamcinolone acetonide. As shown with other PEG containing formulations, there was no impact of this additive on the cumulative percent in vitro release profile as compared to the formulation not containing PEG (data not shown).

Influence of PLGA Lactide to Glycolide Ratio: In other triamcinolone acetonide microparticle formulations, PLGA of equimolar lactide to glycolide ratio were employed instead of PLGA (75:25). PLGA (50:50) is known to allow for faster degradation and release of pharmaceutical agents incorporated into microparticles than PLGA's with greater lactide versus glycolide content (Anderson et al. "Biodegradation and biocompatibility of PLA and PLGA microspheres." *Advanced Drug Delivery Reviews* 28 (1997): 5-24;

Bouissou et al., "Poly(lactic-co-glycolicacid) Microspheres." *Polymer in Drug Delivery* (2006): Chapter 7). Multiple formulations using PLGA 50:50 with differing amounts of triamcinolone acetonide, with and without PEG, different PLGA molecular weights and different PLGA endcaps were exemplified.

Formulations were prepared with 200 mg, 250 mg, 300 mg and 350 mg of triamcinolone acetonide and corresponding amount of PLGA (lactide:glycolide molar ratio of 50:50, inherent viscosity of 0.48 dL/g and molecular weight of 66 kDa) to yield 1000 mg total solids were dispersed into a quantity of dichloromethane to a achieve a 5% PLGA solution. In another iteration, 300 mg of triamcinolone acetonide, 100 mg of polyethylene glycol (PEG 3350) and 650 mg of PLGA (lactide:glycolide molar ratio of 50:50, inherent viscosity of 0.48 dL/g and molecular weight of 66 kDa) were dispersed in 14.25 grams of dichloromethane. In another iteration, 300 mg of triamcinolone acetonide and 700 mg of PLGA (lactide:glycolide molar ratio of 50:50, inherent viscosity of 0.18 dL/g and molecular weight of 18 kDa) to yield 1000 mg total solids were dispersed in 14.25 grams of dichloromethane. The dispersions were atomized into micro-droplets by adding the dispersion to the feed well of a rotating disk, rotating at a speed of approximately 3300 rpm inside a temperature controlled chamber maintained at 38-45° C. The solvent was evaporated to produce solid microparticles. The microparticles were collected using a cyclone separator and, subsequently, sieved through a 150 µm sieve.

Particle size of the TCA incorporated microparticles was determined using laser diffraction (Malvern Mastersizer 2000) by dispersing a 250 mg aliquot in water, with the refractive index (RI) for water and PLGA, set at 1.33 and 1.46 respectively. Sonication was maintained as the sample was stirred at 2500 rpm and measurements taken every 15 seconds, with the average of three measurements reported. 10 mg of TCA containing microparticles were added to 10 mL of dimethylsulfoxide (DMSO), mixed until dissolved and an aliquot analyzed by HPLC to determine the microparticle drug load. Another 4 mg of TCA containing microparticles were suspended in 20 mL of phosphate buffered saline (PBS) containing 0.5% sodium dodecyl sulfate (SDS) maintained at 37° C. 0.5 mL of the media was removed at regular intervals, replaced at each interval with an equivalent amount of fresh media to maintain a constant volume, and analyzed by HPLC to determine microparticle in vitro release. Analysis by HPLC was conducted using a C18 (Waters Nova-Pack C-18, 3.9×150 mm) and 35% acetonitrile mobile phase at 1 ml/min flow rate with UV detection at 240 nm. The results are shown in Table 10.

TABLE 10

Analytical Results of Triamcinolone Acetonide PLGA 50:50 Microparticle Formulations

| PLGA (lactide:glycolide molar ratio/inherent viscosity/ molecular weight/target % TCA/% PEG | Drug load (% TCA by weight) | Incorporation efficiency (%) | Particle size (Dv, µm) | In vitro release (%) |
|---|---|---|---|---|
| 50:50 carboxylic acid end-capped 0.48 dL/g 66 kDa 20% TCA | 19.2 | 96 | D0.1: 30.0 µm D0.5: 48.5 µm D0.9: 77.0 µm | 0.2 day: 2.1 1 day: 3.3 3 day: 17.0 7 day: 18.7 14 day: 21.0 21 day: 23.5 28 day: 25.6 |
| 50:50 carboxylic acid end-capped 0.48 dL/g 66 kDa 25% TCA | 23.9 | 95.6 | D0.1: 30.2 µm D0.5: 48.2 µm D0.9: 75.8 µm | 0.2 day: 4.0 1 day: 7.8 3 day: 21.1 7 day: 32.1 14 day: 39.2 21 day: 40.0 28 day: 40.8 |
| 50:50 carboxylic acid end-capped 0.48 dL/g 66 kDa 30% TCA | 29.3 | 97.6 | D0.1: 31.5 µm D0.5: 48.0 µm D0.9: 68.9 µm | 0.2 day: 5.1 1 day: 16.0 3 day: 33.6 7 day: 49.9 14 day: 54.0 21 day: 53.2 28 day: 52.2 |
| 50:50 carboxylic acid end-capped 0.18 dL/g 18 kDa 30% TCA | 27.2 | 91 | D0.1: 37.6 µm D0.5: 59.8 µm D0.9: 93.9 µm | 0.2 day: 4.4 1 day: 9.8 3 day: 13.8 7 day: 17.7 14 day: 21.9 21 day: 26.3 28 day: 36.6 |
| 50:50 carboxylic acid end-capped 0.48 dL/g 66 kDa 30% TCA 10% PEG 3350 | 30.4 | 101 | D0.1: 38.1 µm D0.5: 56.6 µm D0.9: 82.1 µm | 0.2 day: 4.2 1 day: 14.6 3 day: 32.2 7 day: 51.0 14 day: 60.1 21 day: 61.1 28 day: 60.1 |
| 50:50 carboxylic acid end-capped 0.48 dL/g 66 kDa 35% TCA | 34.4 | 98.3 | D0.1: 35.1 µm D0.5: 52.3 µm D0.9: 75.6 µm | 0.2 day: 7.1 1 day: 23.3 3 day: 47.6 7 day: 66.9 14 day: 69.3 21 day: 68.3 28 day: 66.7 |
| 50:50 ester endcapped 0.4 dL/g 66 kDa 25% TCA | 23.2 | 93 | D0.1: 34.2 µm D0.5: 51.7 µm D0.9: 77.4 µm | 0.2 day: 3.1 1 day: 7.8 3 day: 12.5 7 day: 15.4 14 day: 16.2 21 day: 16.0 28 day: 16.4 |

Figure 19:
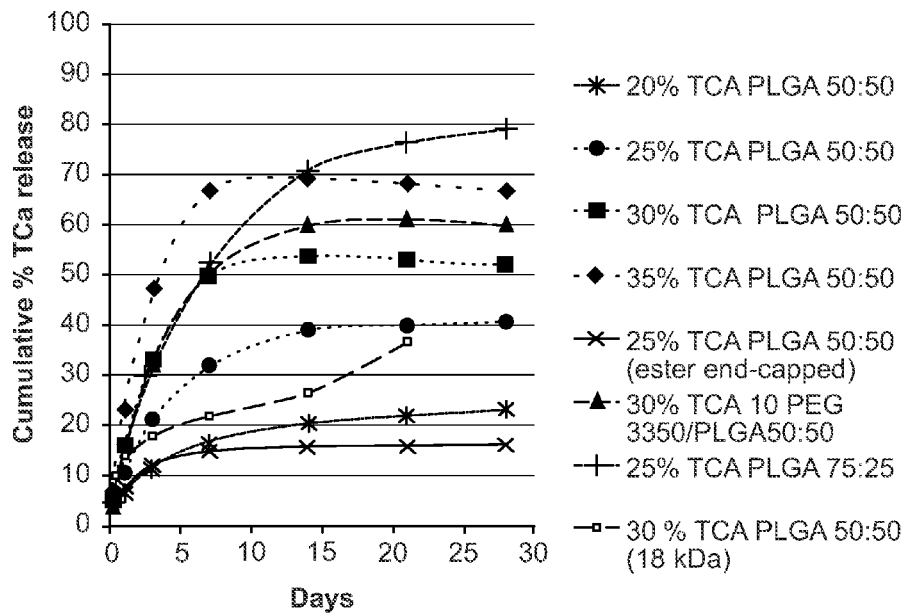
FIG. 19 is a graph depicting cumulative percent release of triamcinolone acetonide in PLGA 50:50 microparticle formulations.

In-vitro release profiles of the various PLGA (50:50) formulations are shown in the FIG. 19. The use of PLGA (50:50) did not improve the release kinetics of the triamcinolone acetonide as compared to the PLGA (75:25). Unexpectedly, 25% triamcinolone acetonide microparticles in PLGA (50:50) release the corticosteroid at a slower rate and give an incomplete release as compared to the equivalent amount of triamcinolone acetonide incorporated in PLGA 75:25. All the PLGA 50:50 formulation show a substantial lag phase, where little or any TCA is being released after 7 days, which continues to about day 50. As observed with TCA PLGA 75:25 formulations, increasing the amount of TCA increases the rate of release and allows for more TCA to be released before entering the lag phase. Similarly, the addition of PEG has minimal influence on the release rate of TCA, while lower molecular weight PLGA 50:50 decrease the release rate as observed with PLGA 75:25 formulations.

Based on the studies described herein, the Class B corticosteroid microparticle formulations, for example, the TCA microparticle formulations, exhibiting the desired release kinetics have the following characteristics: (i) the corticosteroid is between 22%-28% of the microparticle; and (ii) the polymer is PLGA having a molecular weight in the range of about 40 to 70 kDa, having an inherent viscosity in the range of 0.3 to 0.5 dL/g, and or having a lactide:glycolide molar ratio of 80:20 to 60:40.

Example 5

Preparation of Triamcinolone Acetonide PLGA Microparticles by Solid in Oil in Water (S/O/W) Emulsion A pharmaceutical depot was prepared comprised of the corticosteroid, triamcinolone acetonide (TCA, 9α-Fluoro-11β,16α,17α,21-tetrahydroxy-1,4-pregnadiene-3,20-dione 16,17-acetonide; 9α-Fluoro-16α-hydroxyprednisolone 16α, 17α-acetonide) incorporated into microparticles.

Formulations were prepared by dissolving approximately 1 gram of PLGA in 6.67 mL of dichloromethane (DCM). To the polymer solution, 400 mg of triamcinolone acetonide was added and sonicated. Subsequently, the corticosteroid containing dispersion was poured into 200 mL of 0.3% polyvinyl alcohol (PVA) solution while homogenizing with a Silverson homogenizer using a rotor fixed with a Silverson Square Hole High Shear Screen™, set to rotate at approximately 2,000 rpm to form the microparticles. After two minutes, the beaker was removed, and a glass magnetic stirrer) added to the beaker, which was then placed onto a multi-way magnetic stirrer and stirred for four hours at 300 rpm to evaporate the DCM. The microparticles were then washed with 2 liters of distilled water, sieved through a 100 micron screen. The microparticles were then lyophilized for greater than 96 hours and vacuum packed.

Particle size of the TCA incorporated microparticles was determined using laser diffraction (Beckman Coulter LS 230) by dispersing a 50 mg aliquot in water, with the refractive index (RI) for water and PLGA, set at 1.33 and 1.46 respectively. The sample was stirred at the particle size measurement measurements taken and the results reported. Drug load was determined by suspending a nominal 10 mg of microparticles in 8 ml HPLC grade methanol and sonicating for 2 hours. Samples were then centrifuged at 14,000 g for 15 mins before an aliquot of the supernatant was assayed via HPLC as described below. Corticosteroid-loaded microparticle samples, nominally 1 g were placed in 22 ml glass vials in 8-20 ml of 0.5% v/v Tween 20 in 100 mM phosphate buffered saline and stored in a 37° C. incubator with magnetic stirring at 130 rpm. Each test sample was prepared and analyzed in duplicate to monitor possible variability. At each time point in the release study, microparticles were allowed to settle, and an aliquot of between 4-16 ml of supernatant were taken, and replaced with an equal volume of fresh 0.5% v/v Tween 20 in 100 mM phosphate buffered saline. Drug load and in vitro release samples were analyzed by HPLC using a Hypersil C18 column (100 mm, i.d. 5 mm, particle size 5 μm; ThermoFisher) and Beckman HPLC. All samples were run using a sample injection volume of 5 μm, and column temperature of 40° C. An isocratic mobile phase of 60% methanol and 40% water was used at a flow rate of 1 ml/min, with detection at a wavelength of 254 nm.

In one group of suitable thirty day formulations, the PLGA is an ester end capped PLGA (lactide:glycolide molar ratio of 75:25, inherent viscosity of 0.71 dL/g and molecular weight of 114 kDa) with 10% or 20% triblock (TB) polymer (PLGA-PEG-PLGA). Triblock polymer was synthesized using a method described by Zentner et al 2001 (Zentner et al. "Biodegradable block copolymers for delivery of proteins and water-insoluble drugs." *J Control Release* 72 (2001): 203-15) and refined by Hou et al 2008 (Hou et al., "In situ gelling hydrogels incorporating microparticles as drug delivery carriers for regenerative medicine." *J Pharm Sci* 97 (9) (2008): 3972-80). It is synthesized using a ring opening polymerization of cyclic dimmers of D,L-lactide and glycolide with PEG 1,500 kDa in the presence of stannous octoate. In vitro release (lactide:glycolide molar ratio of 50:50, inherent viscosity of 0.40 dL/g and molecular weight of 66 kDa). The analytical results for these formulations are shown in Table 11.

TABLE 11

Analytical Results of Nominal 28.6% Triamcinolone Acetonide in PLGA 75:25 plus Triblock Microparticle Formulations

| PLGA (lactide:glycolide molar ratio ratio/inherent viscosity/ molecular weight/target % TCA/% PEG | Drug load (% TCA by weight) | Incorporation efficiency (%) | Particle size (Dv, μm) | In vitro release (%) |
|---|---|---|---|---|
| 75:25 ester endcapped 0.71 dL/g 114 kDa 28.6% TCA 10% Triblock | 23.8 | 83.2 | D0.1: 38.9 μm D0.5: 74.7 μm D0.9: 103.0 μm | 1 day: 8.2 2 day: 14.2 3 day: 15.7 4 day: 18.2 6 day: 28.8 9 day: 38.9 12 day: 49.8 16 day: 61.6 20 day: 66.4 24 day: 68.7 30 day: 72:3 35 day: 72.8 |
| 75:25 ester endcapped 0.71 dL/g 114 kDa 28.6% TCA 20% Triblock (TB) | 24.8 | 86.7 | D0.1: 39.5 μm D0.5: 74.6 μm D0.9: 104.2 μm | 1 day: 5.5 2 day: 8.9 3 day: 12.8 4 day: 14.5 6 day: 28.4 9 day: 35.6 12 day: 47.8 16 day: 53.0 20 day: 64.3 24 day: 67.3 30 day: 73.0 35 day: 73.0 |

Figure 20:
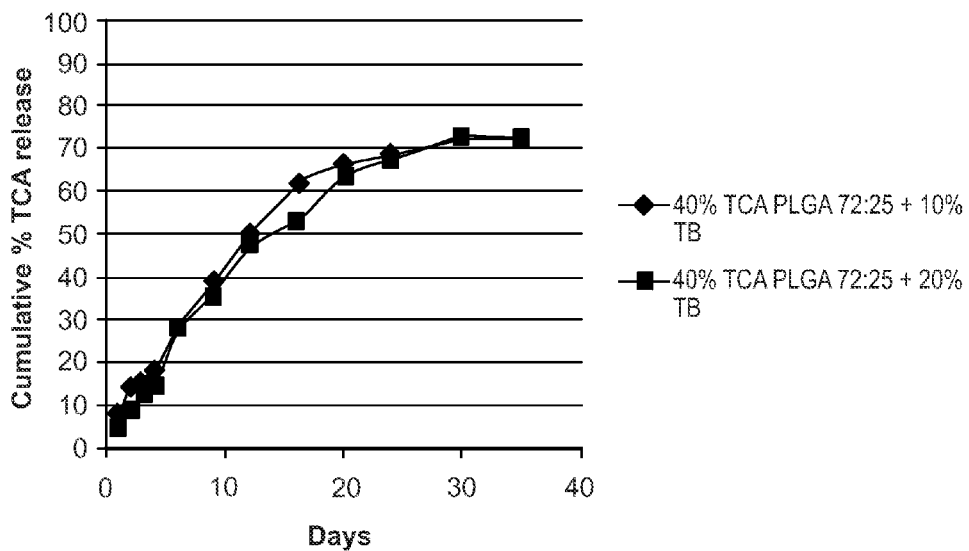
FIG. 20 is a graph depicting cumulative percent release of nominal 28.6% triamcinolone acetonide in PLGA 75:25 plus Triblock microparticle formulations.

The in vitro cumulative release profiles for both triblock containing formulations are shown in FIG. 20. The amount of triblock in the tested formulations did not influence the cumulative percent release.

Figure 21:
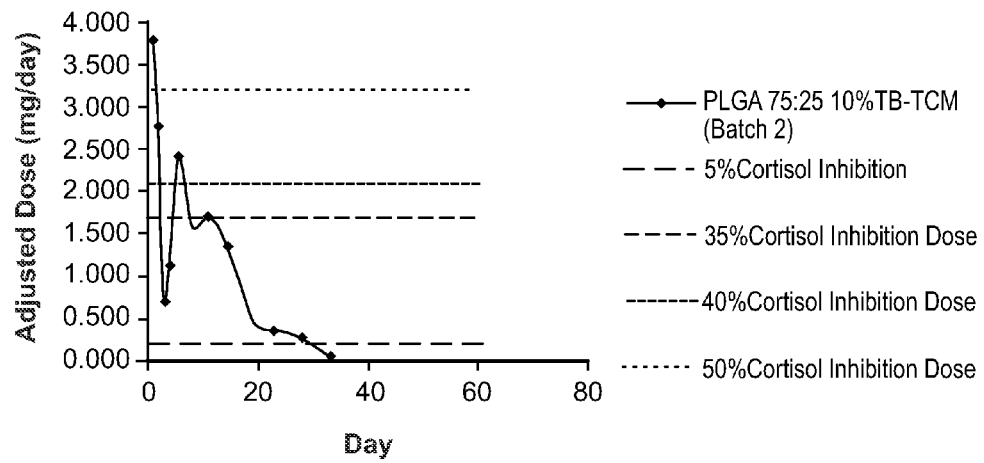
FIG. 21 is a graph depicting calculated human dose to achieve transient cortisol suppression and within 14 days achieve less than 35% cortisol suppression using nominal 28.6% TCA 10% Triblock/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 22:
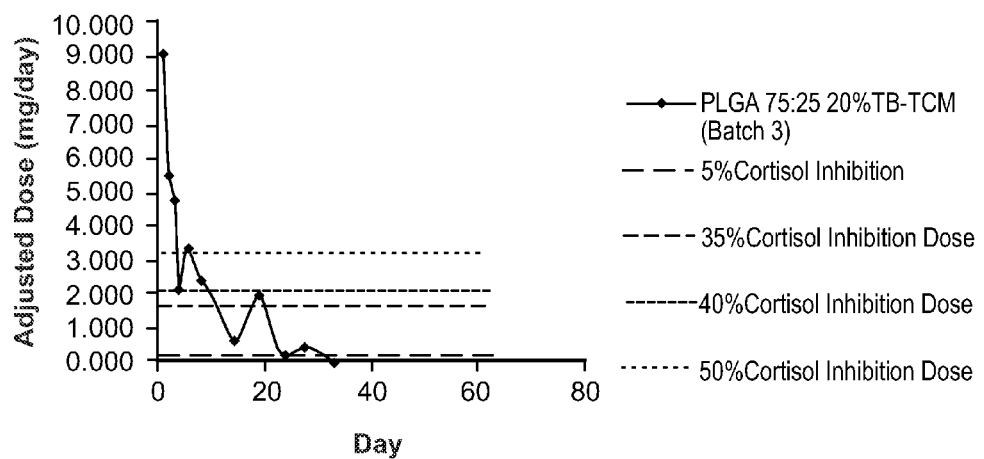
FIG. 22 is a graph depicting calculated human dose to achieve transient cortisol suppression and within 14 days achieve less than 35% cortisol suppression using nominal 28.6% TCA 20% Triblock/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 23:
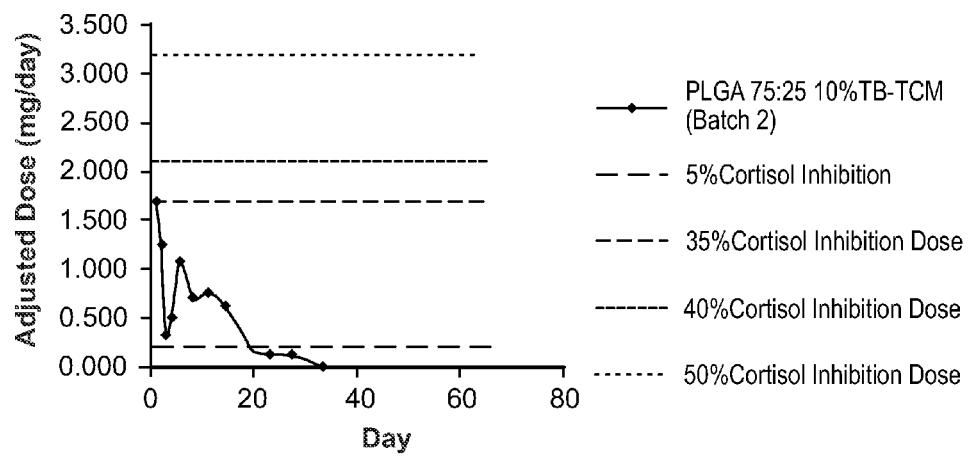
FIG. 23 is a graph depicting calculated human dose that does not affect the HPA axis, less than 35% cortisol suppression using nominal 28.6% TCA 10% Triblock/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 24:
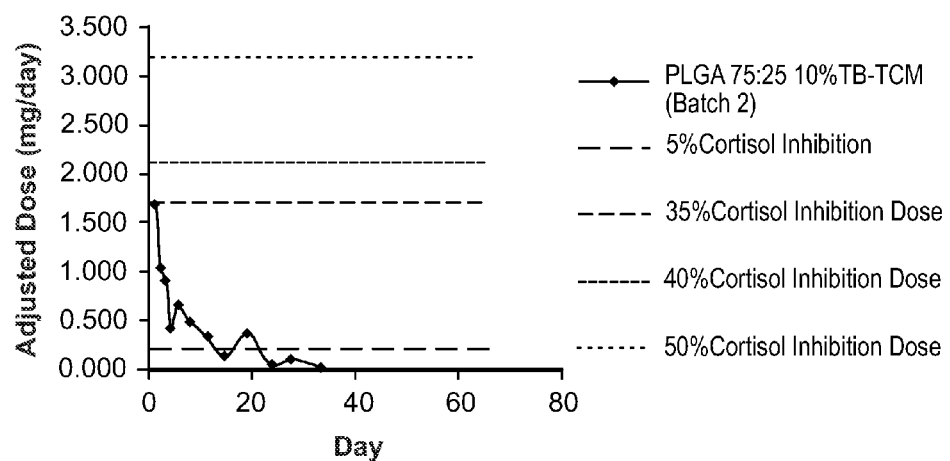
FIG. 24 is a graph depicting calculated human dose that does not affect the HPA axis, less than 35% cortisol suppression using nominal 28.6% TCA 20% Triblock/PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.

In one iteration of these data, the amount of TCA released per day was calculated based on a human dose, as exemplified in Table 2, that may achieve a temporary suppression of endogenous cortisol (greater than 50%) and, within 14 days, achieve cortisol suppression of endogenous cortisol of less than 35%. These calculated doses equal 149 mg of microparticles containing 35 mg of TCA and 252 microparticles containing 62 mg of TCA, for the 10% and 20% triblock formulations respectively (FIG. 21 and FIG. 22). In a second iteration of these data, the amount of TCA released per day was calculated based on a human dose, as exemplified in Table 2, that would not have an suppress the HPA axis, i.e. endogenous cortisol suppression more than 35%. These calculated doses equal 66 mg of microparticles containing 16 mg of TCA and 47 microparticles containing 12 mg of TCA, for the 10% and 20% triblock formulations respectively (FIG. 23 and FIG. 24).

In another suitable formulation lasting greater than 30 days and up to 90 days, the PLGA polymer consists of two different molecular weight PLGA 75:25 polymers in a two to one ratio, PLGA 75:25 (lactide:glycolide molar ratio of 75:25, inherent viscosity of 0.27 dL/g and molecular weight of 29 kDa) and ester end capped PLGA 5.5E (lactide:glycolide molar ratio of 75:25, inherent viscosity of 0.58 dL/g and molecular weight of 86 kDa), respectively. The formulation was processed as described above with the exception that 200 mg of triamcinolone acetonide was used in the formulation instead of 400 mg and similarly analyzed as describe for other formulations. The results are shown in the Table 12.

TABLE 12

Analytical Results of a Nominal 16.7% Triamcinolone Acetonide in Mixed Molecular Weight PLGA 75:25 Microparticle Formulation

| PLGA (lactide:glycolide molar ratio/inherent viscosity/molecular weight/target % TCA/% PEG | Drug load (% TCA by weight) | Incorporation efficiency (%) | Particle size (Dv, μm) | In vitro release (%) |
|---|---|---|---|---|
| 75:25 ester endcapped 0.58 dL/g 86 kDa And 75:25 carboxylic acid endcapped 0.27 dL/g 29 kDa 16.7% TCA | 14.6 | 87.7 | D0.1: 36.5 μm D0.5: 54.0 μm D0.9: 69.4 μm | 1 day: 12.4 2 day: 21.6 3 day: 27.3 4 day 33.6 6 day: 41.2 9 day: 50.7 12 day: 54.3 17 day: 62.0 20 day: 73.1 25 day: 75.5 30 day: 82.9 35 day: 84.6 42 day: 87.4 49 day: 89.2 |

Figure 25:
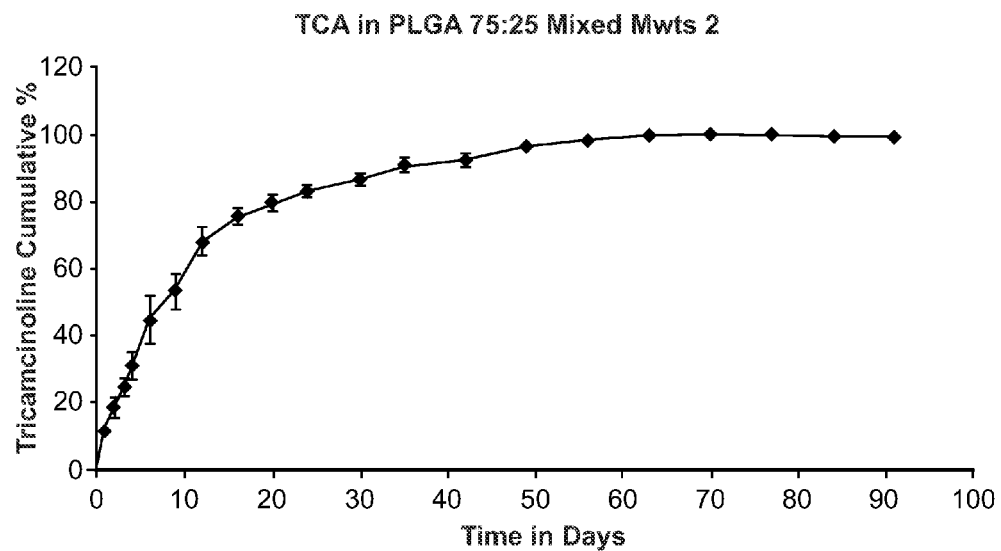
FIG. 25 is a graph depicting cumulative percent release of nominal 16.7% triamcinolone acetonide in mixed molecular weight PLGA 75:25 microparticle formulations.
Figure 26:
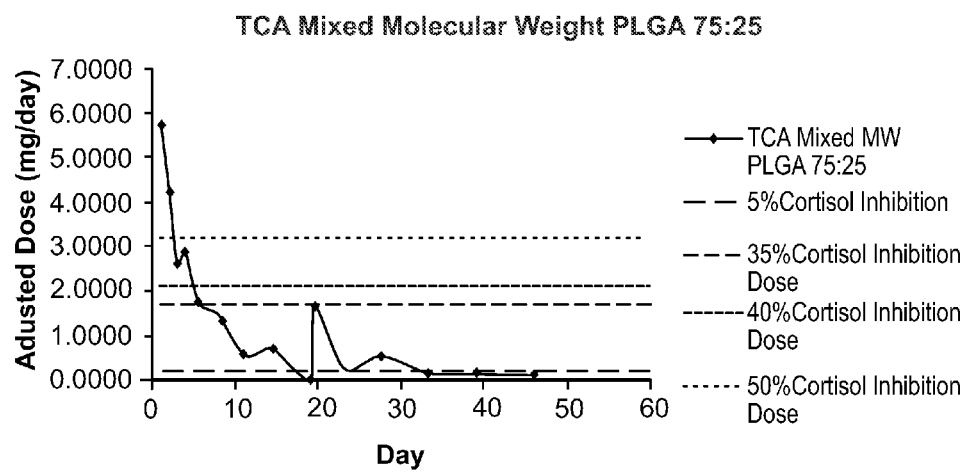
FIG. 26 is a graph depicting calculated human dose to achieve transient cortisol suppression and within 14 days achieve less than 35% cortisol suppression using nominal 16.7% TCA mixed molecular weight PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.
Figure 27:
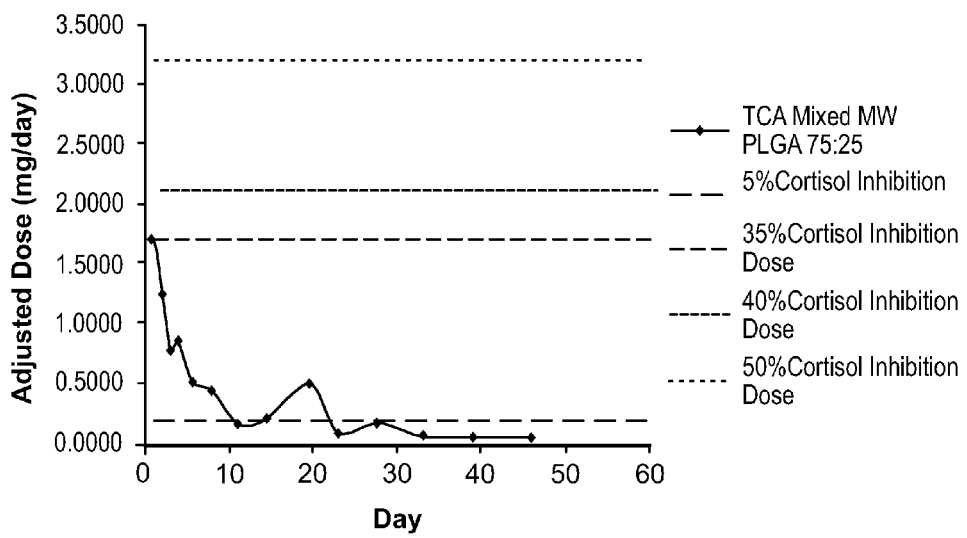
FIG. 27 is a graph depicting calculated human dose that does not affect the HPA axis, less than 35% cortisol suppression using nominal 16.7% TCA mixed molecular weight PLGA 75:25 microparticles. The dotted lines represent, from top to bottom of the graph, 50% cortisol inhibition dose, 40% cortisol inhibition dose, 35% cortisol inhibition dose and 5% cortisol inhibition dose.

In vitro cumulative percent TCA release data is graphed in FIG. 25.

In one iteration of these in vitro release data, the amount of TCA released per day was calculated based on a human dose, as exemplified in Table 2, which may achieve a temporary suppression of endogenous cortisol (greater than 50%) and, within 14 days, achieve cortisol suppression of endogenous cortisol of less than 35%. This calculated dose equals 317 mg of microparticles containing 46 mg of TCA. In a second iteration of these data, the amount of TCA released per day was calculated based on a human dose, as exemplified in Table 2, that would not have an suppress the HPA axis, i.e. endogenous cortisol suppression more than 35%. This calculated dose equals 93 mg of microparticles containing 14 mg of TCA.

Figure 28:
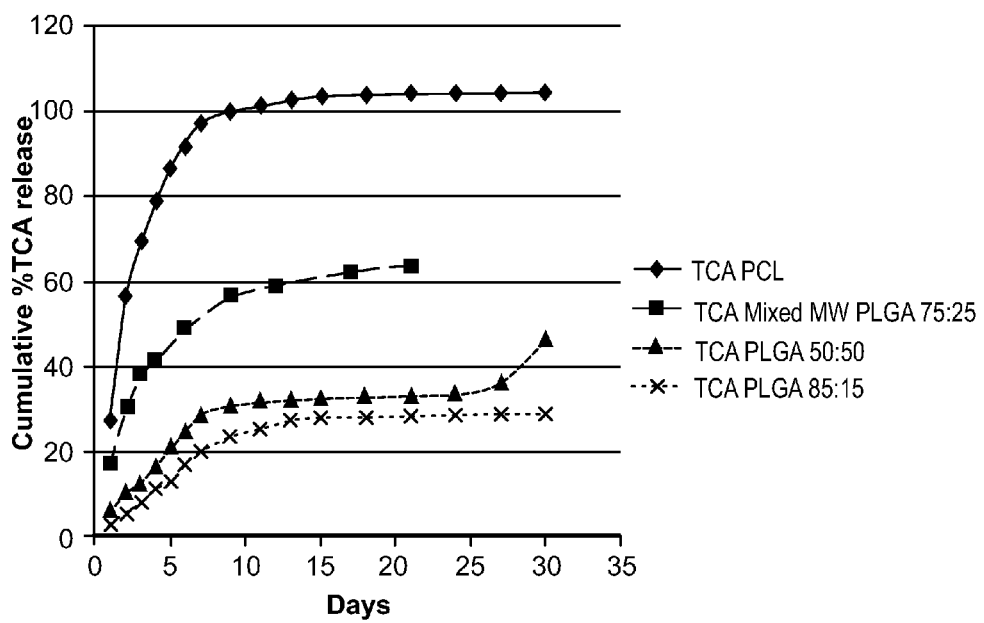
FIG. 28 is a graph depicting cumulative percent release of nominal 28.6% triamcinolone acetonide in various polymer microparticle formulations.

Several other triamcinolone acetonide PLGA depots were formulated in the same manner as described above with different polymers including polycaprolactone (14 kDa), PLGA 50:50 (carboxylic acid end-capped, 0.44 dL/g, MW 56 kDa), PLGA 85:15 (carboxylic acid end-capped, 0.43 dL/g, 56 kDa) and a mixed molecular weight formulation using PLGA 75:25 (carboxylic acid end capped, 0.27 dL/g, MW 29 kDa) and PLGA 75:25 (ester end-capped, 0.57 dL/g, MW 86 kDa) in a two to one ratio. The in vitro cumulative percent release of triamcinolone acetonide is shown in FIG. 28. None of these formulations were suitable for a nominal thirty day or longer duration pharmaceutical depot. Polycaprolactone release all the triamcinolone acetonide prior to 14 days. The PLGA 50:50 microparticles released about 35% of its content by day 12 and then entered a lag phase where no drug was released up to 30 days. The PLGA 85:15 microparticles exhibited similar in vitro release kinetics as the PLGA 50:50, releasing about 30% of its content by day 12 and then entered a lag phase where no drug was released up to 30 days (See FIG. 28). A similar phenomenon is seen as shown in Example 4, where the mixed molecular weight PLGA 75:25 unexpectedly exhibits faster initial release of the triamcinolone acetonide than PLGA 50:50.

Based on the studies described herein, the Class B corticosteroid microparticle formulations, for example, the TCA microparticle formulations, exhibiting the desired release kinetics have the following characteristics: (i) the corticosteroid is between 12%-28% of the microparticle; and (ii) the polymer is (1) PLGA having a molecular weight in the range of about 40 to 70 kDa, having an inherent viscosity in the range of 0.3 to 0.5 dL/g, containing 10%-20% Triblock and/or having a lactide:glycolide molar ratio of 80:20 to 60:40 or (2) a mixture of low and high molecular weight PLGAs in a two to one ratio. The low molecular weight PLGA has a molecular weight of range of 15-35 kDa and an inherent viscosity range from 0.2 to 0.35 dL/g, and the high molecular weight PLGA has a range of 70-95 kDa and an inherent viscosity range of 0.5 to 0.70 dL/g.

Example 6

Preparation of Prednisolone PLGA Microparticles by Solid in Oil in Water (S/O/W) Emulsion A pharmaceutical depot was prepared comprised of the corticosteroid, prednisolone (PRED, 11β,17,21-trihydroxy-pregna-1,4-diene-3,20-dione) incorporated into microparticles in PLGA 50:50.

Formulations were prepared by dissolving approximately 1 gram of PLGA 50:50 (lactide:glycolide molar ratio of 50:50, inherent viscosity 0.44 dL/g, MW 56 kDa) in 6.67 mL of dichloromethane (DCM). To the polymer solution, 400 mg of prednisolone was added and sonicated. Subsequently, the corticosteroid containing dispersion was poured into 200 mL of 0.3% polyvinyl alcohol (PVA) solution while homogenizing with a Silverson homogenizer using a rotor fixed with a Silverson Square Hole High Shear Screen™, set to spin at 2,000 rpm to form the microparticles. After two minutes, the beaker was removed, and a glass magnetic stirrer) added to the beaker, which was then placed onto a multi-way magnetic stirrer and stirred for four hours at 300 rpm to evaporate the DCM. The microparticles were then washed with 2 liters of distilled water, sieved through a 100 micron screen. The microparticles were then lyophilized for greater than 96 hours and vacuum packed.

Particle size of the PRED incorporated microparticles was determined using laser diffraction (Beckman Coulter LS 230) by dispersing a 50 mg aliquot in water, with the refractive index (RI) for water and PLGA, set at 1.33 and 1.46 respectively. The sample was stirred at the particle size measurement measurements taken and the results reported. Drug load was determined by suspending a nominal 10 mg of microparticles in 8 ml HPLC grade methanol and sonicating for 2 hours. Samples were then centrifuged at 14,000 g for 15 mins before an aliquot of the supernatant was assayed via HPLC as described below. Corticosteroid-loaded microparticle samples, nominally 1 g were placed in 22 ml glass vials in 8-20 ml of 0.5% v/v Tween 20 in 100 mM phosphate buffered saline and stored in a 37° C. incubator with magnetic stirring at 130 rpm. Each test sample was prepared and analyzed in duplicate to monitor possible variability. At each time point in the release study, microparticles were allowed to settle, and an aliquot of between 4-16 ml of supernatant were taken, and replaced with an equal volume of fresh 0.5% v/v Tween 20 in 100 mM phosphate buffered saline. Drug load and in vitro release samples were analyzed by HPLC using a Hypersil C18 column (100 mm, i.d. 5 mm, particle size 5 µm; ThermoFisher) and Beckman HPLC. All samples were run using a sample injection volume of 5 µm, and column temperature of 40° C. An isocratic mobile phase of 60% methanol and 40% water was used at a flow rate of 1 ml/min, with detection at a wavelength of 254 nm. The analytical results are shown in the Table 13.

TABLE 13

Analytical Results of a Nominal 28.6% Prednisolone in PLGA 50:50 Microparticle Formulation

| PLGA (lactide:glycolide molar ratio ratio/inherent viscosity/ molecular weight/target % TCA/% PEG | Drug load (% PRED by weight) | Incor- poration efficiency (%) | Particle size (Dv, µm) | In vitro release (%) |
|---|---|---|---|---|
| 50:50 carboxylic acid endcapped 0.44 dL/g 56 kDa 28.6% PRED | 19.0 | 66.4 | D0.1: 34.4 µm D0.5: 66.9 µm D0.9: 87.5 µm | 1 day: 7.2 2 day: 11.5 3 day: 15.6 4 day: 20.2 5 day: 24.0 6 day: 28.4 7 day: 32.7 9 day: 36.5 11 day: 41.4 13 day: 45.0 15 day: 49.3 18 day: 52.0 21 day: 55.2 24 day: 58.3 27 day: 62.3 30 day: 65.9 |

Figure 29:
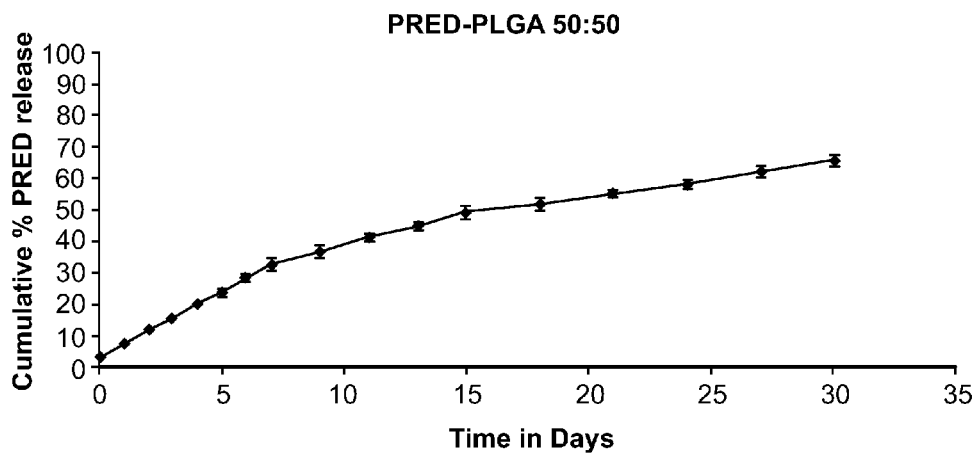
FIG. 29 is a graph depicting cumulative percent release of nominal 28.6% Prednisolone in PLGA 50:50 microparticle formulation.

In vitro release profile of the prednisolone PLGA microparticles is shown in FIG. 29. This formulation is suitable for a 30 day formulation or greater.

Figure 30:
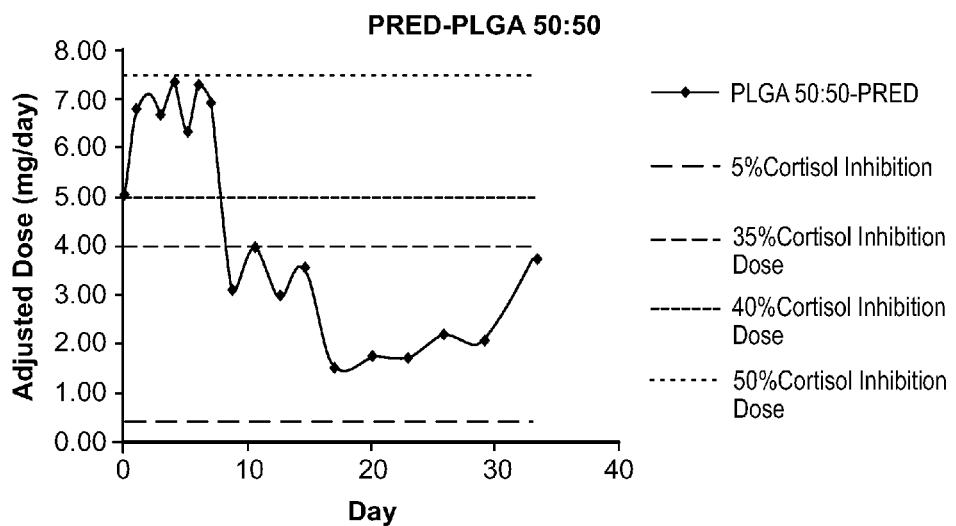
FIG. 30 is a graph depicting calculated human dose to achieve transient cortisol suppression and within 14 days achieve less than 35% cortisol suppression using nominal 28.6% PRED PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.
Figure 31:
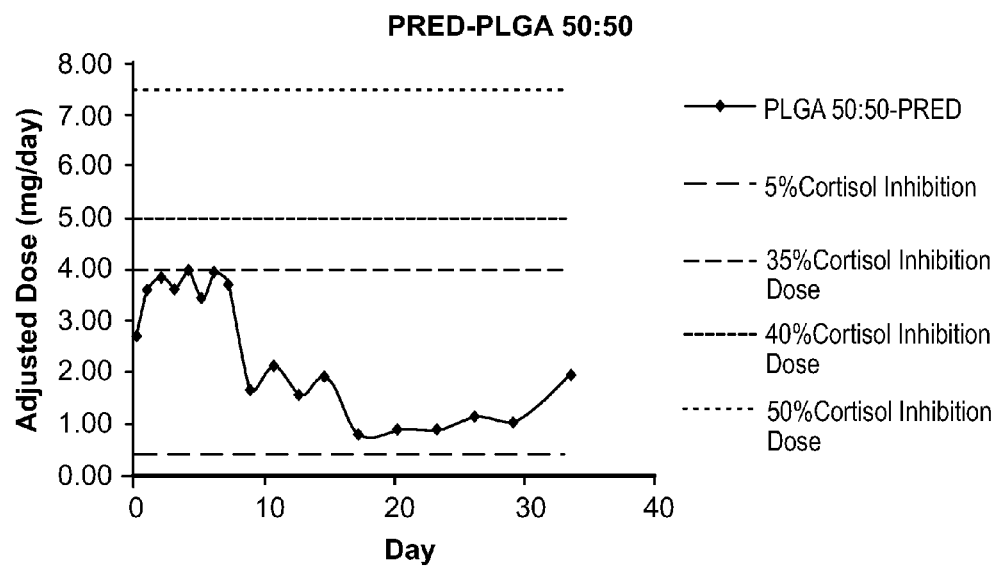
FIG. 31 is a graph depicting calculated human dose that does not affect the HPA axis, less than 35% cortisol suppression using nominal 28.6% PRED PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.

In one iteration of the cumulative percent in vitro release data, the amount of prednisolone released per day was calculated based on a human dose, as exemplified in Table 2, which may achieve a temporary suppression of endogenous cortisol (greater than 50%) and, within 14 days, achieve cortisol suppression of endogenous cortisol of less than 35% (FIG. 30). The calculated dose equals 699 mg of microparticles containing 133 mg of PRED. In a second iteration of these data, the amount of PRED released per day was calculated based on a human dose, as exemplified in Table 2 that would not suppress the HPA axis, i.e. endogenous cortisol suppression of less than 35% (FIG. 31). This calculated dose equals 377 mg of microparticles containing 72 mg of PRED.

Based on the studies described herein, the Class A corticosteroid microparticle formulations, for example, the prednisolone microparticle formulations, exhibiting the desired release kinetics have the following characteristics: (i) the corticosteroid is between 10%-40% of the microparticle, for example, between 15%-30% of the microparticle; and (ii) the polymer is PLGA having a molecular weight in the range of about 45 to 75 kDa, having an inherent viscosity in the range of 0.35 to 0.5 dL/g, and or having a lactide:glycolide molar ratio of 60:40 to 45:55.

Example 7

Preparation of Betamethasone PLGA Microparticles by Solid in Oil in Water (S/O/W) Emulsion A pharmaceutical depot was prepared comprised of the corticosteroid, betamethasone (BETA, 9-Fluoro-11β,17,21-trihydroxy-16β-methylpregna-1,4-diene-3,20-dione) incorporated into microparticles in PLGA 50:50.

A formulation was prepared by dissolving approximately 1 gram of PLGA 50:50 (lactide:glycolide molar ratio of 50:50, inherent viscosity 0.44 dL/g, MW 56 kDa) in 6.67 mL of dichloromethane (DCM). To the polymer solution, 400 mg of betamethasone was added and sonicated. Subsequently, the corticosteroid containing dispersion was poured into 200 mL of 0.3% polyvinyl alcohol (PVA) solution while homogenizing with a Silverson homogenizer using a rotor fixed with a Silverson Square Hole High Shear Screen™, set to spin at 2,000 rpm to form the microparticles. After two minutes, the beaker was removed, and a glass magnetic stirrer) added to the beaker, which was then placed onto a multi-way magnetic stirrer and stirred for four hours at 300 rpm to evaporate the DCM. The microparticles were then washed with 2 liters of distilled water, sieved through a 100 micron screen. The microparticles were then lyophilized for greater than 96 hours and vacuum packed.

Particle size of the BETA incorporated microparticles was determined using laser diffraction (Beckman Coulter LS 230) by dispersing a 50 mg aliquot in water, with the refractive index (RI) for water and PLGA, set at 1.33 and 1.46 respectively. The sample was stirred at the particle size measurement measurements taken and the results reported. Drug load was determined by suspending a nominal 10 mg of microparticles in 8 ml HPLC grade methanol and sonicating for 2 hours. Samples were then centrifuged at 14,000 g for 15 mins before an aliquot of the supernatant was assayed via HPLC as described below. Corticosteroid-loaded microparticle samples, nominally 1 g were placed in 22 ml glass vials in 8-20 ml of 0.5% v/v Tween 20 in 100 mM phosphate buffered saline and stored in a 37° C. incubator with magnetic stirring at 130 rpm. Each test sample was prepared and analyzed in duplicate to monitor possible variability. At each time point in the release study, microparticles were allowed to settle, and an aliquot of between 4-16 ml of supernatant were taken, and replaced with an equal volume of fresh 0.5% v/v Tween 20 in 100 mM phosphate buffered saline. Drug load and in vitro release samples were analyzed by HPLC using a Hypersil C18 column (100 mm, i.d. 5 mm, particle size 5 µm; ThermoFisher) and Beckman HPLC. All samples were run using a sample injection volume of 5 µm, and column temperature of 40° C. An isocratic mobile phase of 60% methanol and 40% water was used at a flow rate of 1 ml/min, with detection at a wavelength of 254 nm. The analytical characteristics of the betamethasone PLGA microparticles are shown in the Table 14.

TABLE 14

Analytical Results of a Nominal 28.6% Betamethasone PLGA 50:50 Microparticle Formulation

| PLGA (lactide:glycolide molar ratio ratio/inherent viscosity/ molecular weight/target % TCA/% PEG | Drug load (% BETA by weight) | Incor- poration efficiency (%) | Particle size (Dv, µm) | In vitro release (%) |
|---|---|---|---|---|
| 50:50 carboxylic acid endcapped | 22.8 | 79.7 | D0.1: 42.1 µm D0.5: 71.7 µm | 1 day: 2.0 2 day: 3.1 |

TABLE 14-continued

Analytical Results of a Nominal 28.6% Betamethasone PLGA 50:50 Microparticle Formulation

| PLGA (lactide:glycolide molar ratio ratio/inherent viscosity/ molecular weight/target % TCA/% PEG | Drug load (% BETA by weight) | Incorporation efficiency (%) | Particle size (Dv, µm) | In vitro release (%) |
|---|---|---|---|---|
| 0.44 dL/g 56 kDa 28.6% BETA | | | D0.9: 102.7 µm | 3 day: 4.8 4 day: 7.7 5 day: 12.5 6 day: 21.4 7 day: 30.8 9 day: 38.6 11 day: 43.9 13 day: 49.6 15 day: 55.5 18 day: 57.5 21 day: 59.2 24 day: 60.8 27 day: 62.9 30 day: 72.4 |

Figure 32:
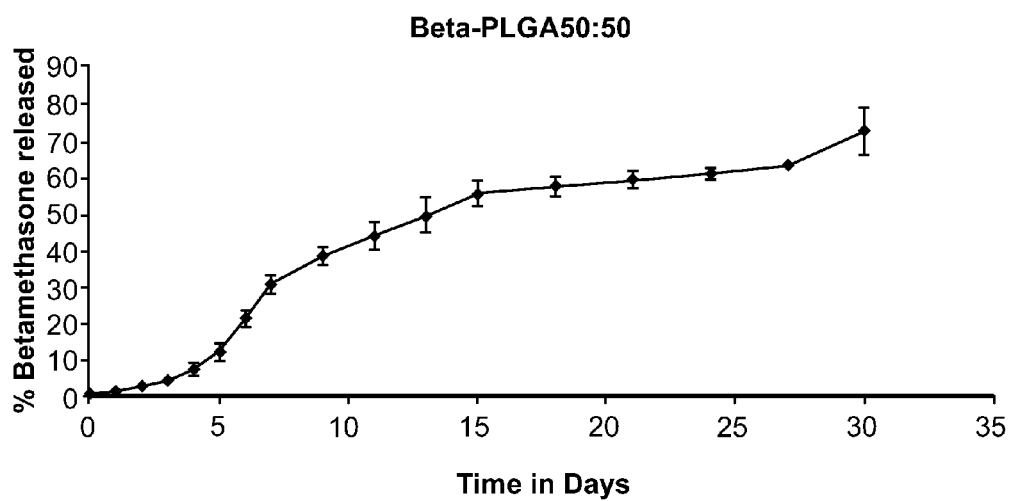
FIG. 32 is a graph depicting cumulative percent release of nominal 28.6% Betamethasone PLGA 50:50 microparticle formulation.

In vitro release profile of the betamethasone PLGA microparticles is shown in FIG. 32. This formulation is suitable for a 30 day formulation or greater.

Figure 33:
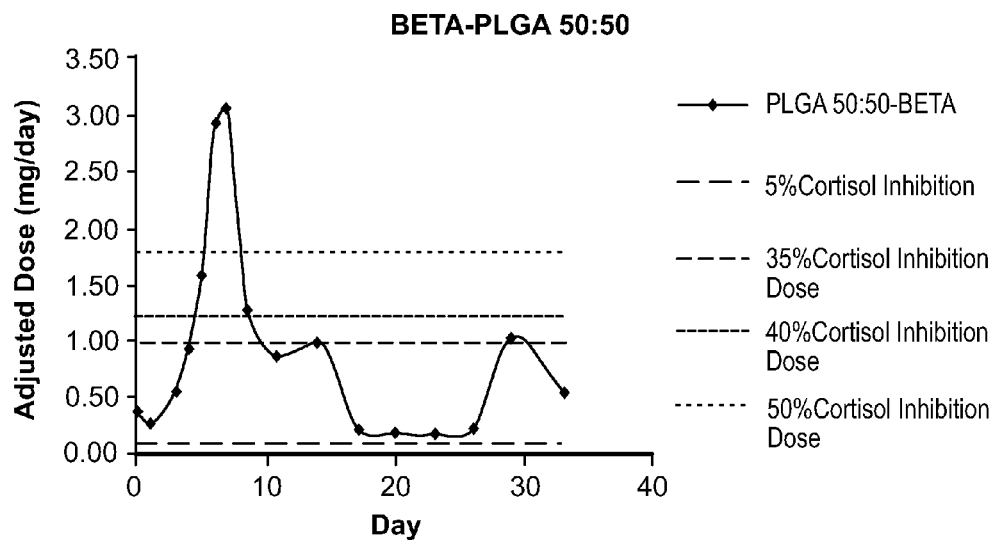
FIG. 33 is a graph depicting calculated human dose to achieve transient cortisol suppression and within 14 days achieve less than 35% cortisol suppression using nominal 28.6% BETA PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.
Figure 34:
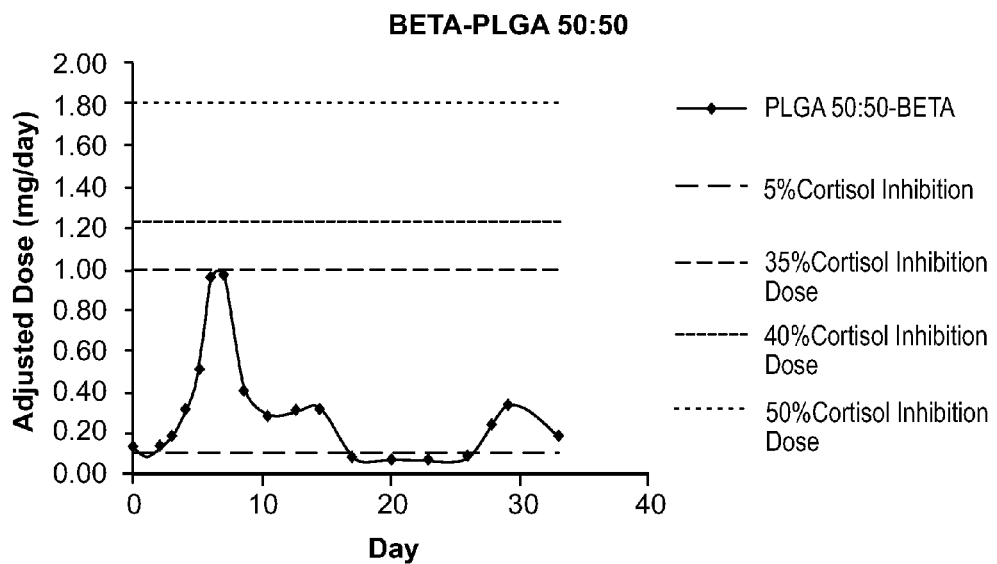
FIG. 34 is a graph depicting calculated human dose that does not affect the HPA axis, less than 35% cortisol suppression using nominal 28.6% BETA PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.

In one iteration of the in vitro release data, the amount of betamethasone released per day was calculated based on a human dose, as exemplified in Table 2, which may achieve a temporary suppression of endogenous cortisol (greater than 50%) and, within 14 days, achieve cortisol suppression of endogenous cortisol of less than 35%. This calculated dose equals 111 mg of microparticles containing 25 mg of betamethasone. In a second iteration of these data, the amount of betamethasone released per day was calculated based on a human dose, as exemplified in Table 2 that would not suppress the HPA axis, i.e. endogenous cortisol suppression never exceeding 35%. This calculated dose equals 38 mg of microparticles containing 9 mg of betamethasone. These doses are both graphically represented in FIGS. 33 and 34.

Based on the studies described herein, the Class C corticosteroid microparticle formulations, for example, the betamethasone microparticle formulations, exhibiting the desired release kinetics have the following characteristics: (i) the corticosteroid is between 10%-40% of the microparticle, for example, between 15%-30% of the microparticle; and (ii) the polymer is PLGA having a molecular weight in the range of about 40 to 70 kDa, having an inherent viscosity in the range of 0.35 to 0.5 dL/g, and or having a lactide:glycolide molar ratio of 60:40 to 45:55.

Example 8

Preparation of Fluticasone Propionate PLGA Microparticles by Solid in Oil in Water (S/O/W) Emulsion A pharmaceutical depot was prepared comprised of the corticosteroid, fluticasone propionate (FLUT, S-(fluoromethyl) 6α,9-difluoro-11β,17-dihydroxy-16α-methyl-3-oxoandrosta-1,4-diene-17β-carbothioate, 17-propionate) incorporated into microparticles in PLGA 50:50.

A formulation was prepared by dissolving approximately 1 gram of PLGA 50:50 (lactide:glycolide molar ratio of 50:50, inherent viscosity 0.45 dL/g, molecular weight 66 kDa) in 6.67 mL of dichloromethane (DCM). To the polymer solution, 200 mg of fluticasone propionate was added and sonicated. Subsequently, the corticosteroid containing dispersion was poured into 200 mL of 0.3% polyvinyl alcohol (PVA) solution while homogenizing with a Silverson homogenizer using a rotor fixed with a Silverson Square Hole High Shear Screen™, set to spin at 2,000 rpm to form the microparticles. After two minutes, the beaker was removed, and a glass magnetic stirrer) added to the beaker, which was then placed onto a multi-way magnetic stirrer and stirred for four hours at 300 rpm to evaporate the DCM. The microparticles were then washed with 2 liters of distilled water, sieved through a 100 micron screen. The microparticles were then lyophilized for greater than 96 hours and vacuum packed.

Particle size of the FLUT incorporated microparticles was determined using laser diffraction (Beckman Coulter LS 230) by dispersing a 50 mg aliquot in water, with the refractive index (RI) for water and PLGA, set at 1.33 and 1.46 respectively. The sample was stirred at the particle size measurement measurements taken and the results reported. Drug load was determined by suspending a nominal 10 mg of microparticles in 8 ml HPLC grade methanol and sonicating for 2 hours. Samples were then centrifuged at 14,000 g for 15 mins before an aliquot of the supernatant was assayed via HPLC as described below. Corticosteroid-loaded microparticle samples, nominally 1 g were placed in 22 ml glass vials in 8-20 ml of 0.5% v/v Tween 20 in 100 mM phosphate buffered saline and stored in a 37° C. incubator with magnetic stirring at 130 rpm. Each test sample was prepared and analyzed in duplicate to monitor possible variability. At each time point in the release study, microparticles were allowed to settle, and an aliquot of between 4-16 ml of supernatant were taken, and replaced with an equal volume of fresh 0.5% v/v Tween 20 in 100 mM phosphate buffered saline. Drug load and in vitro release samples were analyzed by HPLC using a Hypersil C18 column (100 mm, i.d. 5 mm, particle size 5 µm; ThermoFisher) and Beckman HPLC. All samples were run using a sample injection volume of 5 µm, and column temperature of 40° C. An isocratic mobile phase of 60% methanol and 40% water was used at a flow rate of 1 ml/min, with detection at a wavelength of 254 nm. The analytical results of the fluticasone propionate PLGA microparticles are shown in Table 15.

TABLE 15

Analytical Results of a Nominal 16.7% Fluticasone PLGA 50:50 Microparticle Formulation

| PLGA (lactide:glycolide molar ratio ratio/inherent viscosity/ molecular weight/target % FLUT/ | Drug load (% FLUT by weight) | Incorporation efficiency (%) | Particle size (Dv, µm) | In vitro release (%) |
|---|---|---|---|---|
| 50:50 carboxylic acid endcapped 0.45 dL/g 66 kDa 16.7% FLUT | 8.5 | 51.1 | D0.1: 34.1 µm D0.5: 65.5 µm D0.9: 95.0 µm | 1 day: 29.5 2 day: 43.5 3 day: 46.7 4 day: 50.9 5 day: 55.5 6 day: 58.6 |

TABLE 15-continued

Analytical Results of a Nominal 16.7% Fluticasone PLGA 50:50 Microparticle Formulation

| PLGA (lactide:glycolide molar ratio/inherent viscosity/ molecular weight/target % FLUT/ | Drug load (% FLUT by weight) | Incorporation efficiency (%) | Particle size (Dv, μm) | In vitro release (%) |
|---|---|---|---|---|
| | | | | 7 day: 60.1 |
| | | | | 9 day: 63 |
| | | | | 11 day: 66.8 |
| | | | | 13 day: 67.8 |
| | | | | 15 day: 68.7 |
| | | | | 18 day: 73.7 |
| | | | | 21 day: 81.8 |
| | | | | 24 day: 93.7 |
| | | | | 26 day: 97.1 |
| | | | | 31 day: 100.8 |

Figure 35:
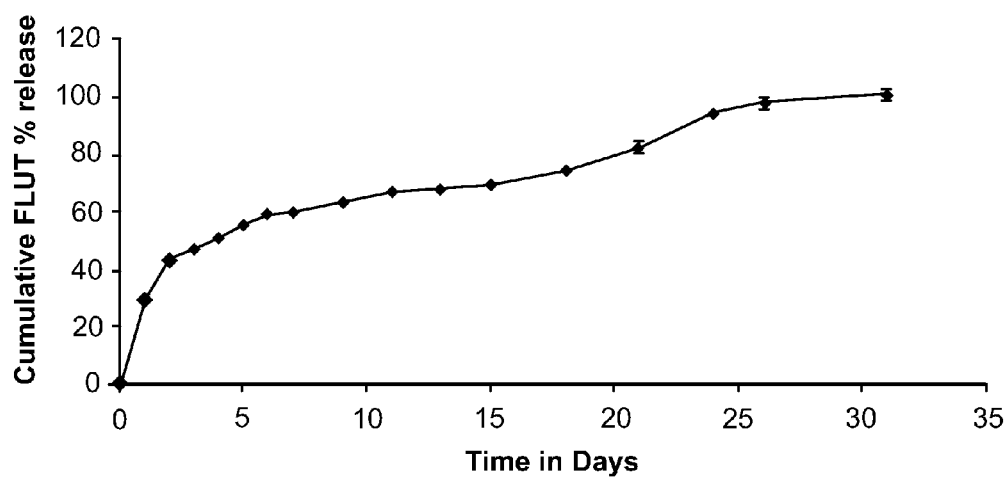
FIG. 35 is a graph depicting cumulative percent release of nominal 16.7% Fluticasone Propionate PLGA 50:50 microparticle formulation.

In vitro release profile of the fluticasone propionate PLGA microparticles is shown in FIG. 35. This formulation is suitable for a 30 day formulation or greater.

Figure 36:
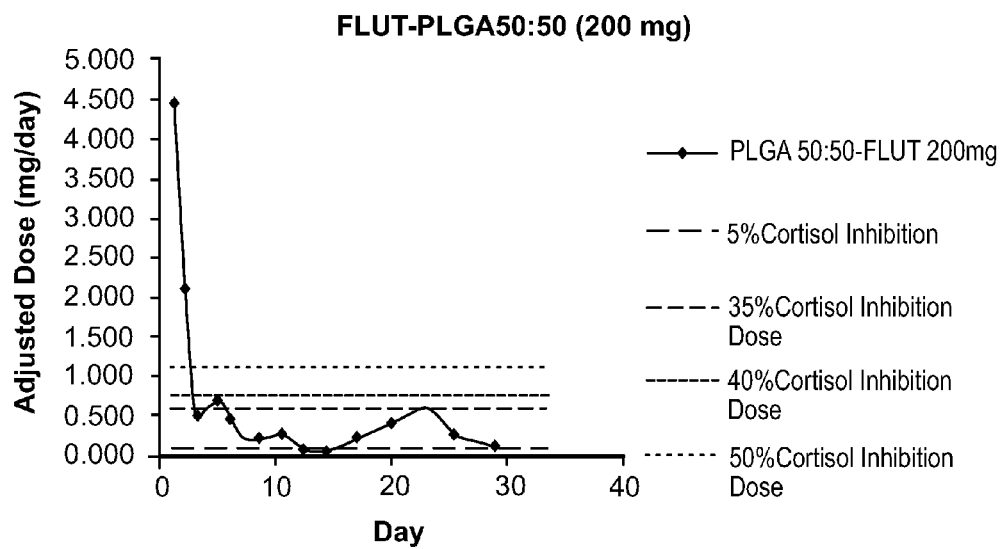
FIG. 36 is a graph depicting calculated human dose to achieve transient cortisol suppression and within 14 days achieve less than 35% cortisol suppression using nominal 16.7% FLUT PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.
Figure 37:
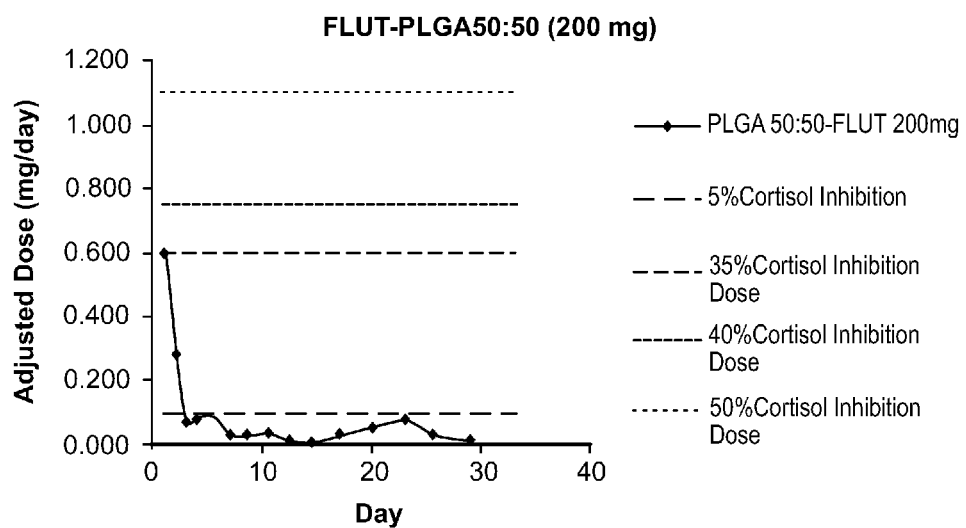
FIG. 37 is a graph depicting calculated human dose that does not affect the HPA axis, less than 35% cortisol suppression using nominal 16.7% FLUT PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.

In one iteration of the in vitro release data, the amount of fluticasone propionate released per day was calculated based on a human dose, as exemplified in Table 2, which may achieve a temporary suppression of endogenous cortisol (greater than 50%) and, within 14 days, achieve cortisol suppression of endogenous cortisol of less than 35%. This calculated dose equals 178 mg of microparticles containing 15 mg of fluticasone propionate. In a second iteration of these data, the amount of fluticasone propionate released per day was calculated based on a human dose, as exemplified in Table 2 that would not suppress the HPA axis, i.e. endogenous cortisol suppression never exceeding 35%. This calculated dose equals 24 mg of microparticles containing 2 mg of fluticasone propionate. These doses are both graphically represented in FIGS. 36 and 37.

Figure 38:
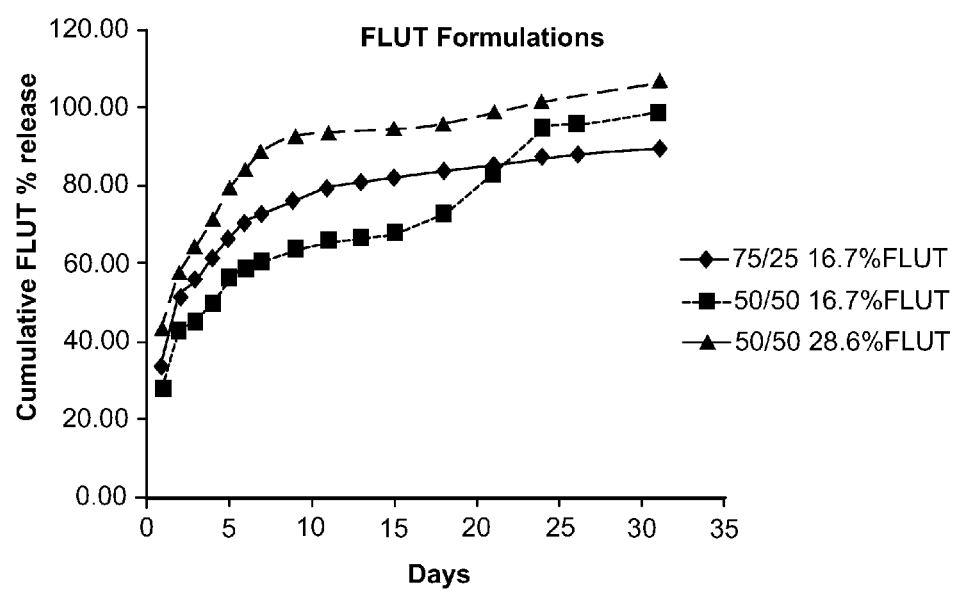
FIG. 38 is a graph depicting cumulative percent release of various Fluticasone Propionate PLGA microparticle formulations.
Figure 39:
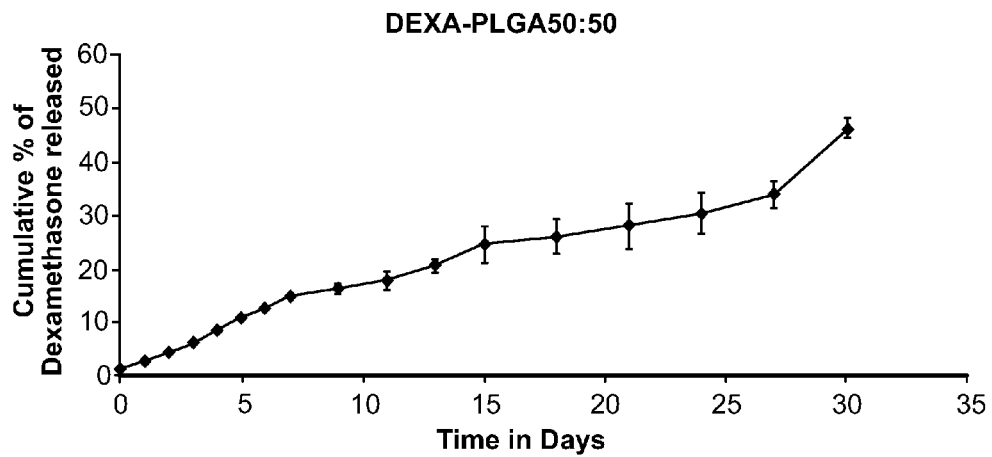
FIG. 39 is a graph depicting cumulative percent release of nominal 28.6% DEX PLGA 50:50 microparticle formulation.

Other fluticasone propionate PLGA depots were formulated in the same manner as described above with different PLGA polymers or amounts fluticasone propionate. In one formulation, a PLGA polymer with a higher lactide to glycolide ratio (PLGA 75:25 (ester end-capped PLGA 75:25, lactide:glycolide molar ratio of 75:25, 0.58 dL/g, MW 86 kDa) was used instead of the PLGA 50:50 as previously described. Unlike the triamcinolone acetonide preparations described in Example 5, but typically expected as described in the literature, the higher lactide to glycolide ratio resulted in a slower release, where 30% release in 14 days, followed by a substantial lag phase where little drug is released for a minimum of thirty days. In another example, 400 mg of fluticasone propionate instead of 200 mg was used in preparation of PLGA 50:50 microparticles (target drug load 28.6%). Unlike triamcinolone acetonide microparticle preparations, the higher drug load did not result in a significantly different release of fluticasone propionate; FIG. 38 shows the in vitro release of all three fluticasone propionate formulations.

Based on the studies described herein, the Class D corticosteroid microparticle formulations, for example, the fluticasone or fluticasone propionate microparticle formulations, exhibiting the desired release kinetics have the following characteristics: (i) the corticosteroid is between 8%-20% of the microparticle, and (ii) the polymer is PLGA having a molecular weight in the range of about 40 to 70 kDa, having an inherent viscosity in the range of 0.35 to 0.5 dL/g, and or having a lactide:glycolide molar ratio of 60:40 to 45:55.

Example 9

Preparation of Dexamethasone Microparticles by Solvent Dispersion in PLGA

A pharmaceutical depot was prepared comprised of the corticosteroid, dexamethasone (DEX, 9-Fluoro-11β,17,21-trihydroxy-16α-methylpregna-1,4-diene-3,20-dione) incorporated into microparticles in PLGA 50:50.

A formulation was prepared by dissolving approximately 1 gram of PLGA 50:50 (lactide:glycolide molar ratio of 50:50, inherent viscosity 0.45 dL/g, molecular weight 66 kDa) in 6.67 mL of dichloromethane (DCM). To the polymer solution, 200 mg of dexamethasone was added and sonicated. Subsequently, the corticosteroid containing dispersion was poured into 200 mL of 0.3% polyvinyl alcohol (PVA) solution while homogenizing with a Silverson homogenizer using a rotor fixed with a Silverson Square Hole High Shear Screen™, set to spin at 2,000 rpm to form the microparticles. After two minutes, the beaker was removed, and a glass magnetic stirrer) added to the beaker, which was then placed onto a multi-way magnetic stirrer and stirred for four hours at 300 rpm to evaporate the DCM. The microparticles were then washed with 2 liters of distilled water, sieved through a 100 micron screen. The microparticles were then lyophilized for greater than 96 hours and vacuum packed.

Particle size of the DEX incorporated microparticles was determined using laser diffraction (Beckman Coulter LS 230) by dispersing a 50 mg aliquot in water, with the refractive index (RI) for water and PLGA, set at 1.33 and 1.46 respectively. The sample was stirred at the particle size measurement measurements taken and the results reported. Drug load was determined by suspending a nominal 10 mg of microparticles in 8 ml HPLC grade methanol and sonicating for 2 hours. Samples were then centrifuged at 14,000 g for 15 mins before an aliquot of the supernatant was assayed via HPLC as described below. Corticosteroid-loaded microparticle samples, nominally 1 g were placed in 22 ml glass vials in 8-20 ml of 0.5% v/v Tween 20 in 100 mM phosphate buffered saline and stored in a 37° C. incubator with magnetic stirring at 130 rpm. Each test sample was prepared and analyzed in duplicate to monitor possible variability. At each time point in the release study, microparticles were allowed to settle, and an aliquot of between 4-16 ml of supernatant were taken, and replaced with an equal volume of fresh 0.5% v/v Tween 20 in 100 mM phosphate buffered saline. Drug load and in vitro release samples were analyzed by HPLC using a Hypersil C18 column (100 mm, i.d. 5 mm, particle size 5 μm; ThermoFisher) and Beckman HPLC. All samples were run using a sample injection volume of 5 μm, and column temperature of 40° C. An isocratic mobile phase of 60% methanol and 40% water was used at a flow rate of 1 ml/min, with detection at a wavelength of 254 nm. The analytical results for the dexamethasone PLGA microparticles are shown in Table 16.

TABLE 16

Analytical Results of a Nominal 28.6% Dexamethasone PLGA 50:50 Microparticle Formulation

| PLGA (lactide:glycolide molar ratio ratio/inherent viscosity/ molecular weight/target % FLUT/ | Drug load (% DEX by weight) | Incorporation efficiency (%) | Particle size (Dv, μm) | In vitro release (%) |
|---|---|---|---|---|
| 50:50 carboxylic acid endcapped 0.45 dL/g 66 kDa 28.6% DEX | 22.1 | 77.2 | D0.1: 41.2 μm D0.5: 71.9 μm D0.9: 99.1 μm | 1 day: 2.9 2 day: 4.6 3 day: 6.3 4 day: 8.7 5 day: 10.9 6 day: 12.7 7 day: 15.0 9 day: 16.4 11 day: 18.0 13 day: 20.7 15 day: 24.6 18 day: 26.2 21 day: 28.1 24 day: 30.3 27 day: 34.0 30 day: 46.3 |

In vitro cumulative percent release of the dexamethasone is shown in 39, and results in suitable formulation for a minimum of thirty days and, assuming linear release, likely up to 60 days.

Figure 40:
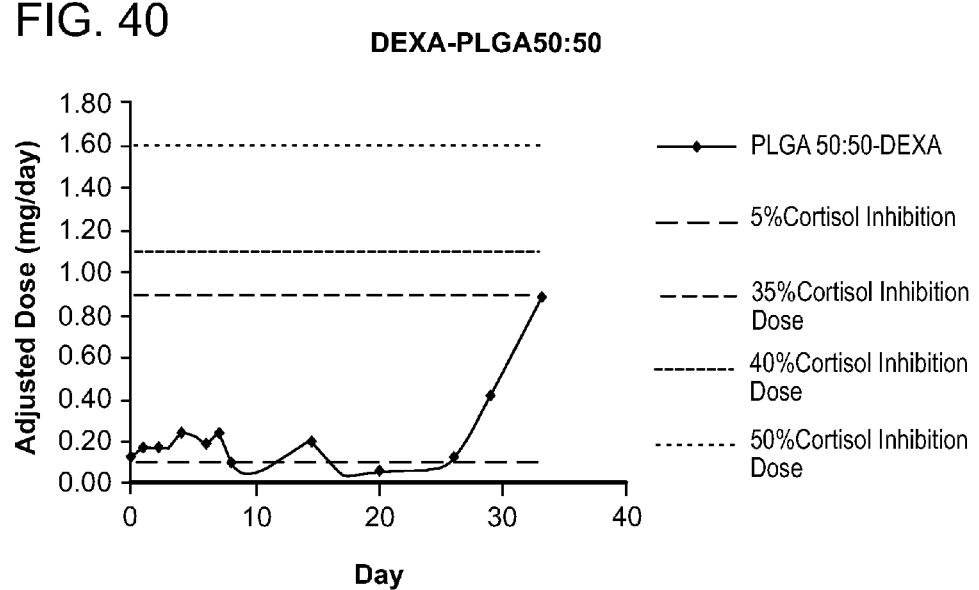
FIG. 40 is a graph depicting calculated human dose to achieve transient cortisol suppression and within 14 days achieve less than 35% cortisol suppression and does not affect the HPA axis, less than 35% cortisol suppression using nominal 28.6% DEX PLGA 50:50 microparticles. The dotted lines represent, from top to bottom of the graph, 50% cortisol inhibition dose, 40% cortisol inhibition dose, 35% cortisol inhibition dose and 5% cortisol inhibition dose.
Figure 41A:
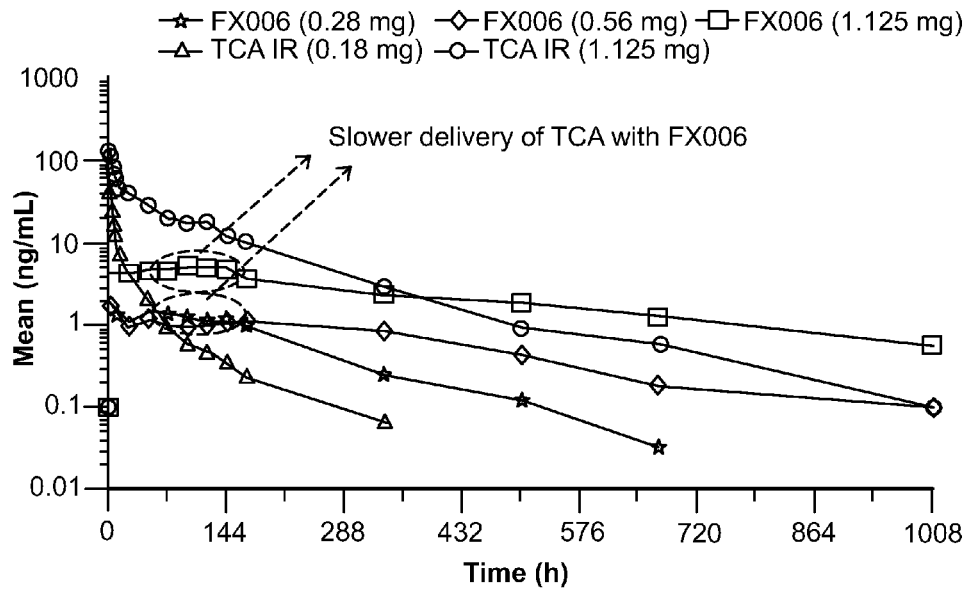
FIGS. 41A-41D are a series of graphs depicting the mean concentration-time profiles of various doses of TCA IR and FX006 in rat plasma following single intra-articular doses. A microparticle formulation of TCA in 75:25 PLGA formulation microparticles, referred to as FX006, dosed at 1.125 mg resulted in a very slow absorption of TCA in the systemic circulation and a markedly lower $C_{max}$ as compared to TCA IR. Concentrations for the first 72 hr are presented in FIGS. 41C and 41D on a larger time scale.
Figure 41B:
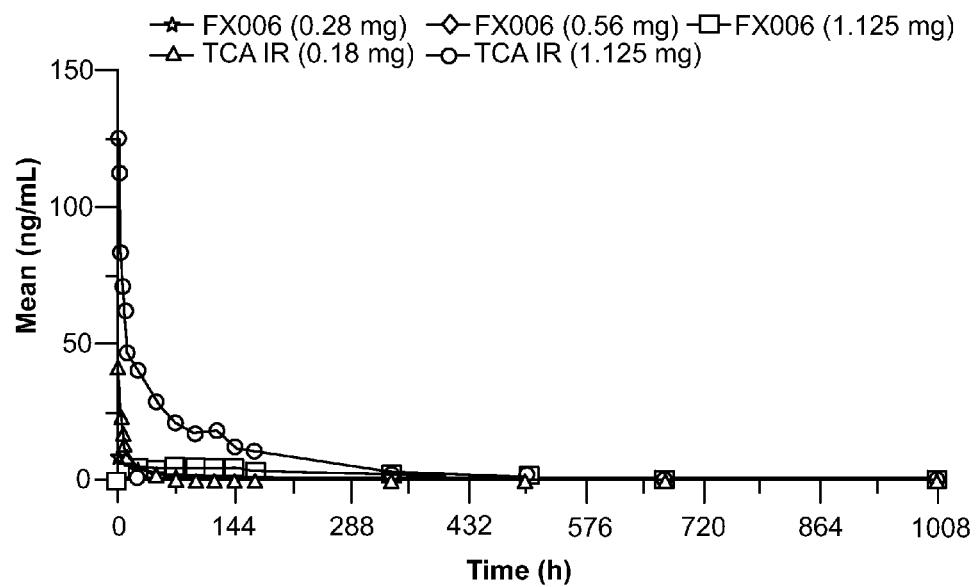
Figure 41C:
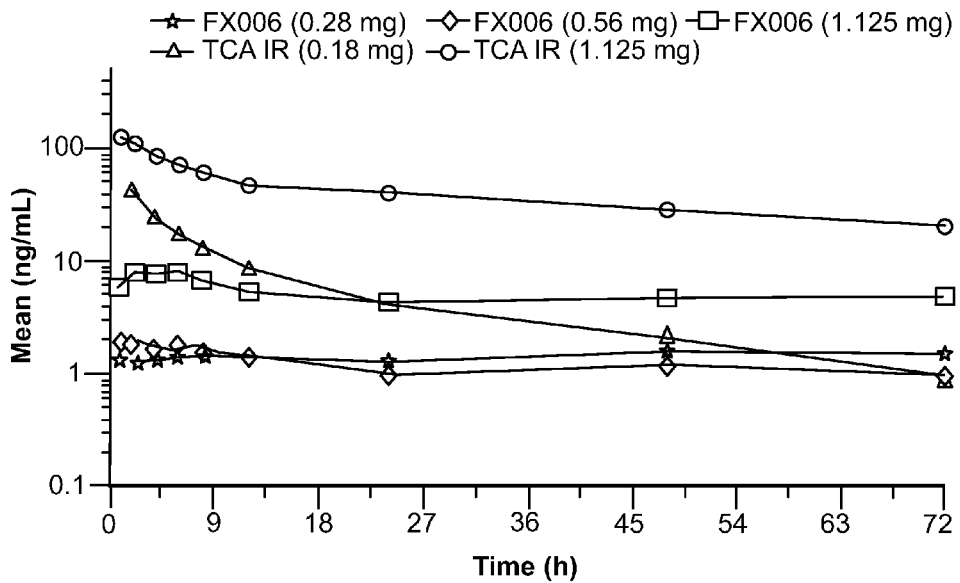
Figure 41D:
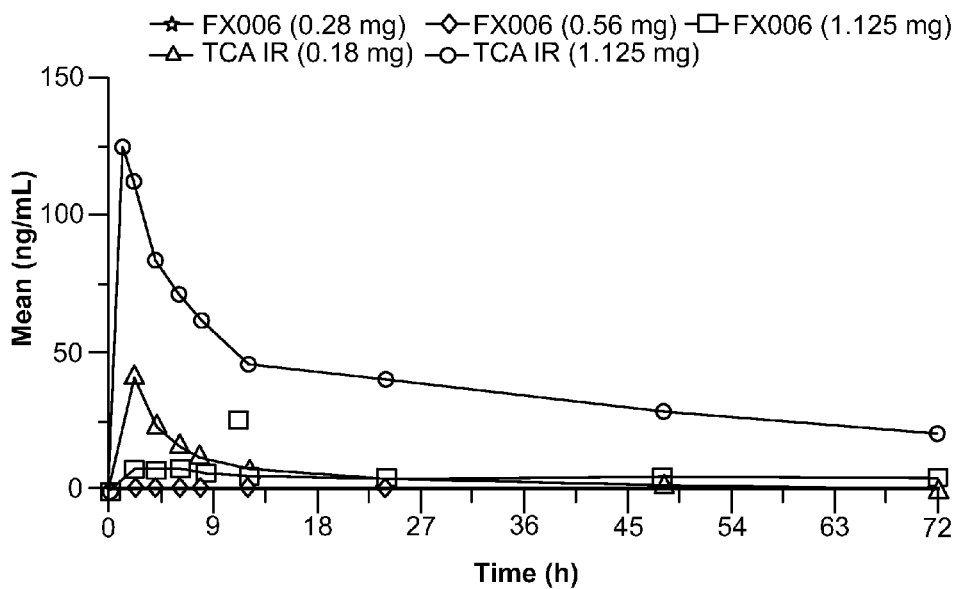

In one iteration of the in vitro release data, the amount of dexamethasone released per day was calculated based on a human dose, as exemplified in Table 2, which may achieve a temporary suppression of endogenous cortisol (greater than 50%) and, within 14 days, achieve cortisol suppression of endogenous cortisol of less than 35%. In a second iteration of these data, the amount of dexamethasone released per day was calculated based on a human dose, as exemplified in Table 2 that would not suppress the HPA axis, i.e. endogenous cortisol suppression never exceeding 35%. In the case of dexamethasone, where the data is truncated, both calculated human doses are the same; 36 mg of microparticles containing 8 mg of dexamethasone. The doses are graphically represented in FIG. 40.

Example 10

Figure 42:
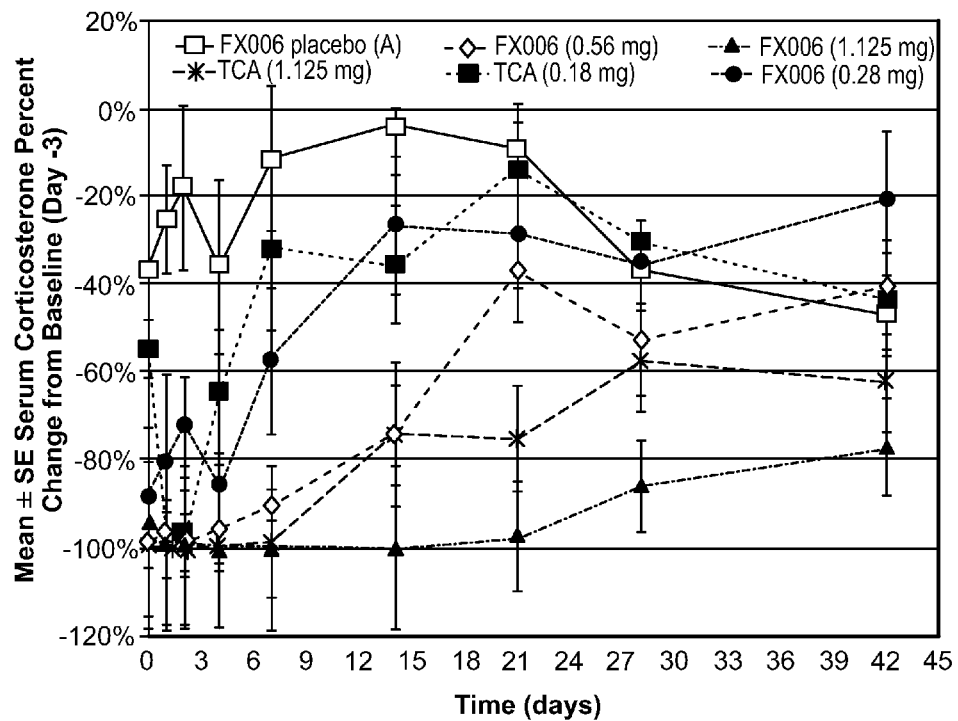
FIG. 42 is a graph depicting corticosteroid inhibition and recovery with TCA IR (immediate release) and FX006 (microparticle formulation) in rats.
Figure 43:
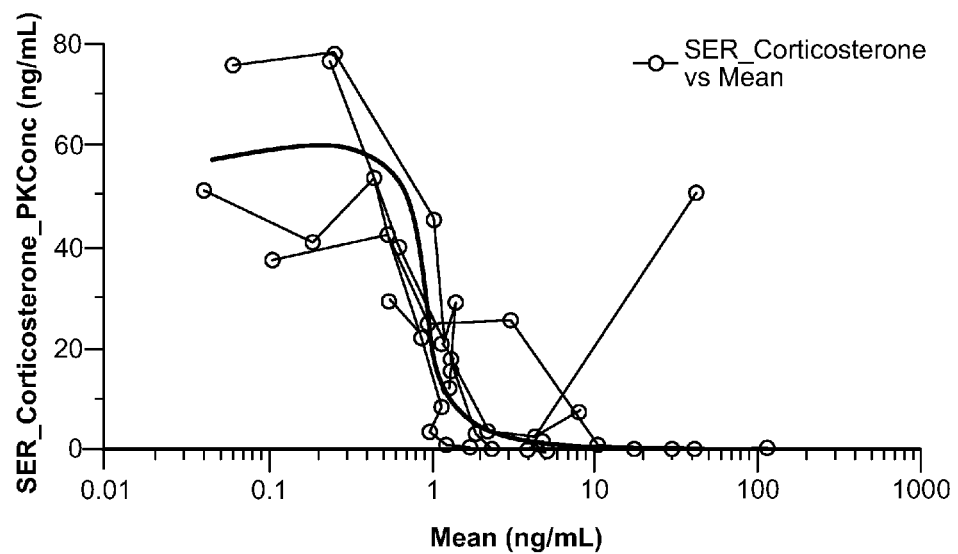
FIG. 43 is a graph depicting the pharmacokinetic/pharmacodynamic (PK/PD) relationship of systemic TCA levels and corticosterone inhibition.

Pharmacology, Pharmacokinetics and Exploratory Safety Study of Corticosteroid Formulations In an exploratory safety study in rats, single intra-articular (IA) doses of TCA immediate release (TCA IR) (0.18 and 1.125 mg) and doses of TCA in 75:25 PLGA formulation microparticles (FX006) (0.28, 0.56 and 1.125 mg (i.e., the maximum feasible dose) of TCA) were evaluated. Blood samples were collected at various time points for determination of plasma concentrations. Plasma concentration-time data from this study and pharmacokinetic (PK) analysis thereof are shown in FIGS. 41-43 and Tables 17-20.

As seen in FIGS. 41A-41D, FX006 dosed at 1.125 mg resulted in a very slow absorption of TCA in the systemic circulation and a markedly lower $C_{max}$ as compared to TCA IR.

As shown in Table 17, the mean $AUC_{0-t}$ values of TCA following 1.125 mg administration of FX006 were 2.1-fold lower than those observed for TCA IR (i.e., 2856 vs. 6065 ng·h/mL, respectively). The mean $C_{max}$ values of TCA following 1.125 mg administration of FX006 were 15-fold lower than those observed for TCA IR (i.e., 125 vs. 8.15 ng/mL, respectively). The absorption of TCA following administration of FX006 was slower than that observed for TCA IR, with mean $T_{max}$ values observed at 3.33 and 1.00 h, respectively. The elimination half-life of TCA following administration of 1.125 mg FX006 and TCA IR were 451 and 107 h, respectively.

TABLE 17

Summary of TCA Plasma Pharmacokinetic Parameters

| | Treatment | | | | | | | | | |
|---|---|---|---|---|---|---|---|---|---|---|
| | FX006 (0.28 mg) | | FX006 (0.56 mg) | | FX006 (1.125 mg) | | TCA IR (0.18 mg) | | TCA IR (1.125 mg) | |
| Variable | Mean | (CV %) | Mean | (CV %) | Mean | (CV %) | Mean | (CV %) | Mean | (CV %) |
| $AUC_{0-24}$ (ng · h/mL) | 31.0 | (76.0) | 33.0 | (19.1) | 136 | (6.0) | 297 | (21.5) | 1403 | (13.2) |
| $AUC_{0-\infty}$ (ng · h/mL) | 356 | (62.0) | 572 | (21.5) | 2856 | (17.2) | 479 | (32.6) | 6065 | (3.7) |
| $AUC_{0-t}$ (ng · h/mL) | 335 | (66.5) | 532 | (23.8) | 2142 | (14.4) | 456 | (31.3) | 6013 | (3.4) |
| CL/F (mL/h) | 1308 | (96.6) | 1014 | (24.4) | 403 | (19.1) | 400 | (27.6) | 186 | (3.6) |
| $C_{max}$ (ng/mL) | 1.82 | (66.2) | 1.91 | (10.2) | 8.15 | (12.5) | 41.6 | (25.1) | 125 | (5.3) |
| $T_{1/2}$ (h) | 99.5 | (39.9) | 180 | (27.0) | 451 | (20.8) | 35.6 | (63.5) | 107 | (56.7) |
| $T_{max}$ (h) | 17.7 | (148.9) | 16.7 | (162.8) | 3.38 | (69.3) | 2.00 | (0.0) | 1.00 | (0.0) |
| $V_{ss}/F$ (mL) | 274215 | (117.0) | 326966 | (30.2) | 240481 | (17.7) | 12069 | (53.4) | 23829 | (34.4) |

The above results suggest a slower distribution and bioavailability of TCA in the systemic circulation following administration of FX006 as compared to TCA IR. Without wishing to be bound by theory, the slower distribution FX006 into the systemic circulation may be related to the longer residence time of FX006 at the site of injection. This is supported by the lesser availability of the FX006 microparticle formulation in the early "burst" phase, where only 4-9% of product is released, compared to at least 23% of the IR product.

Bioavailability of TCA in the systemic circulation following administration of FX006 was 3-fold lower than that observed for TCA IR, as shown in Table 18.

TABLE 18

Bioavailability of TCA in Plasma

Absolute Bioavailability Comparison

| | FX006 (0.28 mg) | TCA IR (0.18 mg) |
|---|---|---|
| $F_{abs}$ (%) | 17.9 | 58.6 |

For the 0.56 and 1.125 mg dose levels of FX006, apparent F % were 23.1% and 58.1%, respectively. The IV data in rats shown in Table 19 was used as a reference to calculate F.

TABLE 19

Pharmacokinetic Parameters of TCA in Rat Plasma After i.v. (50 mg/kg bolus + 23 mg/kg/h Infusion) Administration of Triamcinolone Acetonide Phosphate

| Parameter | Rat 1 | Rat 2 | Rat 3 | Mean ± SD |
|---|---|---|---|---|
| $V_c$ (L/kg) | 0.684 | 0.856 | 1.29 | 0.944 ± 0.314 |
| CL (L/h/kg) | 1.15 | 0.790 | 0.872 | 0.937 ± 0.188 |
| $k_{12}$ (h$^1$) | 1.64 | 1.79 | 1.59 | 11.67 ± 0.102 |
| $k_{21}$ (h$^1$) | 1.04 | 0.640 | 1.13 | 0.937 ± 0.261 |
| $T_{1/2\beta}$ (h) | 1.55 | 3.71 | 2.87 | 2.71 ± 1.09 |
| $f_u$ | 0.084 | 0.110 | 0.085 | 0.093 ± 0.015 | from Rojas et al., "Microdialysis of triamcinolone acetonide in rat muscle." *J Pharm Sci* 92 (2) (2003):394-397.

The initial "burst" (i.e., exposure up to 24 h) accounted for less than 10% of the total systemic exposure of FX006. The initial burst accounted for ~23-62% of the total exposure for the TCA IR product, as shown in Table 20.

TABLE 20

Relative Availability of TCA in Plasma (Initial Burst vs. Delayed Release)

| | Treatment | | | | |
|---|---|---|---|---|---|
| Variable | FX006 (0.28 mg) Mean | FX006 (0.56 mg) Mean | FX006 (1.125 mg) Mean | TCA IR (0.18 mg) Mean | TCA IR (1.125 mg) Mean |
| $AUC_{0-24}$ (ng · h/mL) | 31.0 | 33.0 | 136 | 297 | 1403 |
| $AUC_{0-\infty}$ (ng · h/mL) | 356 | 572 | 2856 | 479 | 6065 |
| $AUC_{24-\infty}$ (ng · h/mL) | 325 | 539 | 2720 | 182 | 4662 |
| % Initial Burst | 8.69 | 5.76 | 4.76 | 62.1 | 23.1 |

In this same study, groups of animals were sacrificed 28 days after dosing, and the remaining were terminated on Day 42. Body weights were monitored throughout the study and key organs (spleen, adrenal glands, thymus) were weighed upon necropsy. The injected knee and the contralateral control joints were prepared for histological assessment. Toluidine blue stained sections of joints were evaluated for treatment-related alterations. Histologic changes were described, wherever possible, according to their distribution, severity, and morphologic character.

Histological analysis demonstrated the following observations. First, injected joints from placebo (blank PLGA microspheres)-treated animals had minimal multifocal macrophage infiltration in associated with 20-130 μm diameter microspheres, whereas none of the active FX006-injected joints showed the presence of any microspheres at Day 28. Placebo-treated rat joints had no cartilage or joint changes save for the presence of spontaneous cartilage cysts in a few joints (1 at Day 28, 2 at Day 42) in the right (injected) knees. The left knees in the placebo-treated rat joints were normal. In comparison, both knees in the high dose TCA IR and the high and mid-dose FX006—groups showed some mild bone marrow hypocellularity and growth plate atrophy (dose dependent for FX006). Both knees in the low dose TCA IR and FX006 animals were normal. Spontaneous cartilage cysts noted in placebo animals were also noted in all groups dosed with FX006 with no increase in incidence or severity. High dose TCA IR increased cartilage cysts at Day 42 but not at Day 28. In general, FX006-treated animals had normal articular cartilage despite the presence of catabolic effects on other joint structures, which was likely more readily observed on account of the young age of the animals.

Overall, all observed effects of FX006, especially at the high dose, such as body weight loss and reduced organ weights were also seen with TCA IR. The time course of inhibition of the HPA axis (measured as corticosterone levels) is shown in FIG. 42. It should be noted that at the lowest dose of FX006 (0.28 mg; circles) corticosterone levels were initially inhibited but recovered back to near baseline by Day 14 post-dose. Similarly, with TCA IR at the lowest dose (0.18 mg), corticosterone levels recovered by Day 7 (squares). With the mid (0.56 mg) and high (1.125 mg) doses of FX006 and the high dose of TCA IR (1.125 mg), corticosterone levels were inhibited longer as shown in FIG. 42.

A PK-PD analysis demonstrated that inhibition of corticosterone was correlated with systemic TCA levels and followed a classical inhibitory model as shown in FIG. 43. The $IC_{50}$ was about 1 ng/mL and the $E_{max}$ was achieved at 50-80 ng/mL.

Example 11

Evaluation of Efficacy of Single Doses of TCA Immediate Release and TCA Microparticle Formulation in Animal Model of Osteoarthritis The studies described herein were designed to test and evaluate the efficacy of the corticosteroid microparticle formulations provided herein as compared to immediate release corticosteroid formulations. While the studies herein use TCA, it is understood that other corticosteroids, including other Class B corticosteroids, Class A corticosteroids, Class C corticosteroids, and Class D corticosteroids, can be evaluated using these materials, methods and animal models.

Efficacy of single intra-articular (IA) doses of FX006 (TCA in 75:25 PLGA formulation microparticles) and TCA IR (immediate release) was evaluated in a rat model of osteoarthritis of the knee via sensitization and challenge by peptidoglycan polysaccharide (PGPS). The model involves priming the animals with an intra-articular injection of PGPS in the right knee. The following day, any animals with no knee discomfort were eliminated from the test article groups and placed into the baseline group. Two weeks later, knee inflammation was reactivated by a tail vein injection of PGPS, 2.5 hr following IA dosing with FX006 or TCA IR at the doses selected (n=10/group). Differences in weight-bearing and gait (as a measure of joint pain experienced by the animals), histopathology, plasma PK etc. were evaluated.

Doses of FX006 (0.28, 0.12, 0.03 mg) and TCA IR (0.06, 0.03 mg) for this study were selected based on data from the study described above in Example 10 and an initial run of the PGPS model in which only TCA IR was evaluated at two IA dose levels. The goals of the present study were to demonstrate the following:

FX006 is efficacious at doses that do not inhibit the HPA axis

The duration of efficacy is a function of dose

FX006 provides more prolonged pain relief as compared to TCA IR—Since only about 10% of the TCA payload is expected to be released from FX006 in the first 24 hr, one TCA IR dose group (0.03 mg) was chosen to match 10% of the TCA in FX006 at a dose of 0.28 mg Effects of matched doses of FX006 and TCA IR (0.03 mg)

The duration of efficacy was assessed by 3 different reactivations, 2 weeks apart. After that point, the arthritis observed in the animals becomes more wide-spread making the efficacy in the index knee more difficult to assess.

Figure 44A:
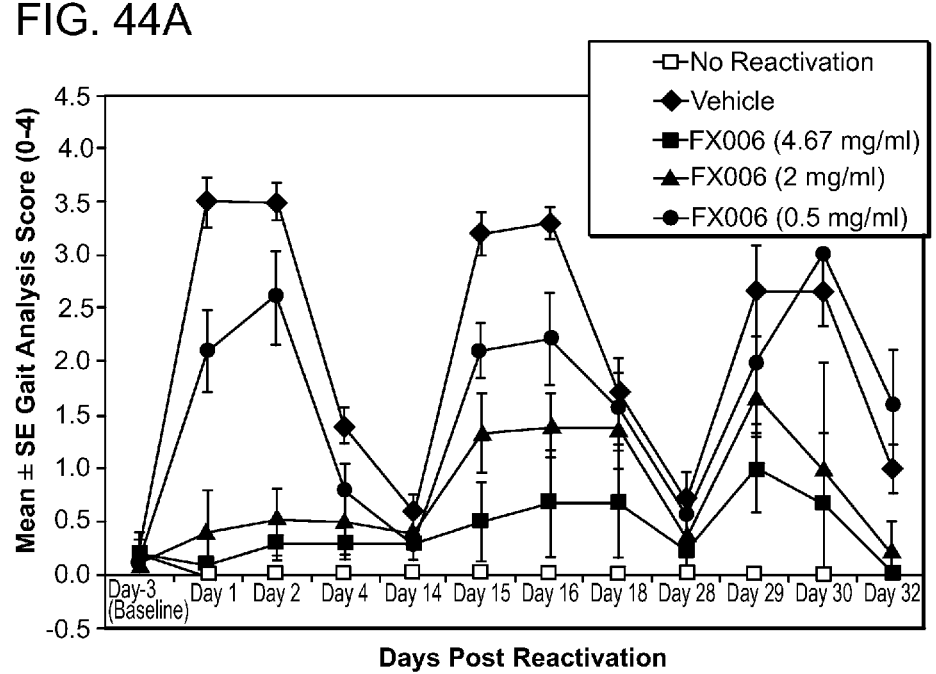
FIGS. 44A-44C are a series of graphs depicting the gait analysis scores, an indicator of pain, in rats injected with doses of either immediate release triamcinolone acetonide (TCA IR) or TCA microparticles (FX006) in a model of osteoarthritis.
Figure 44B:
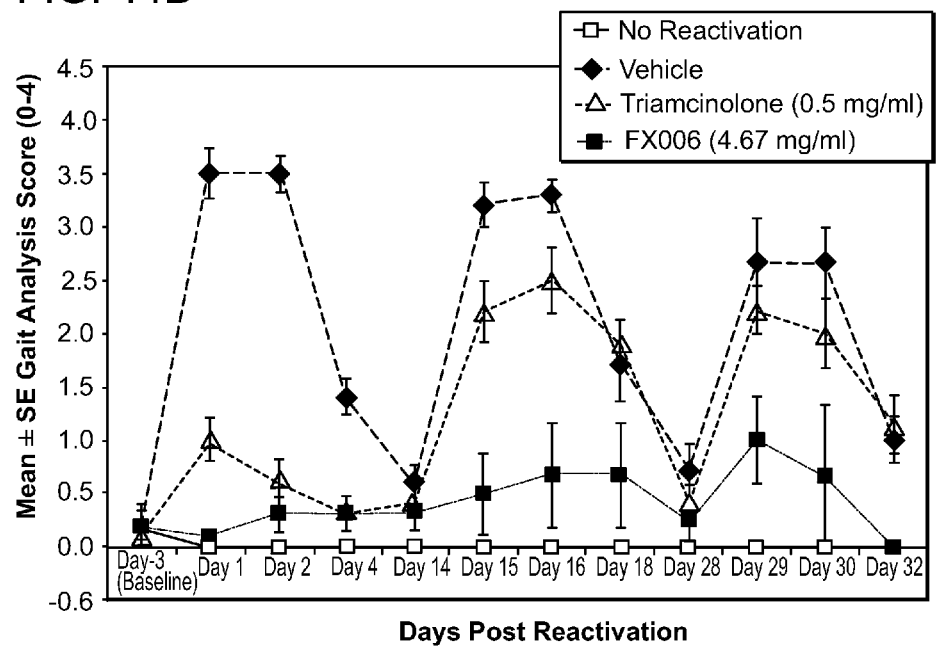
Figure 44C:
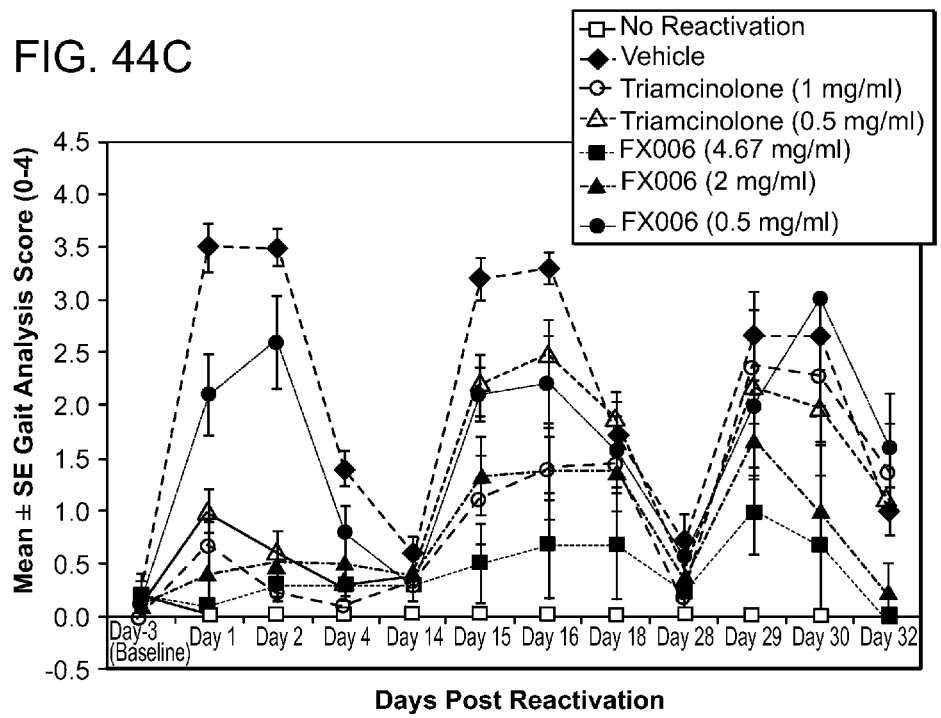

At the first reactivation, vehicle treated animals demonstrate painful gait as demonstrated by high pain scores (3.5 out of a maximum of 4 possible) as shown in FIGS. 44A, 44B, and 44C. FX006 at 0.28 mg (squares) showed good efficacy. In the previous study described in Example 10, this dose was demonstrated to inhibit the HPA axis immediately after dosing but a return to baseline function was demonstrated by Day 14. Interestingly, this dose of FX006 continued to be efficacious upon the $2^{nd}$ and $3^{rd}$ reactivations on Days 14 and 28 when the HPA axis function was presumably normal. It should also be noted that since HPA axis function returned to baseline by Day 7 at a 0.18 mg dose of TCA IR in the previous study described in Example 10, the effects of the doses of TCA IR used in the present study (0.06 and 0.03 mg) were also in the presence of normal HPA axis function following an initial transient inhibition. Corticosterone measurements from the present study (as an indicator of HPA axis function) are presented as change from baseline for each treatment group in FIG. 46. As demonstrated from these data, corticosterone levels for all groups recovered by Day 14; hence the goal of prolonged efficacy with FX006 in the presence of normal HPA axis function was achieved.

Figure 45:
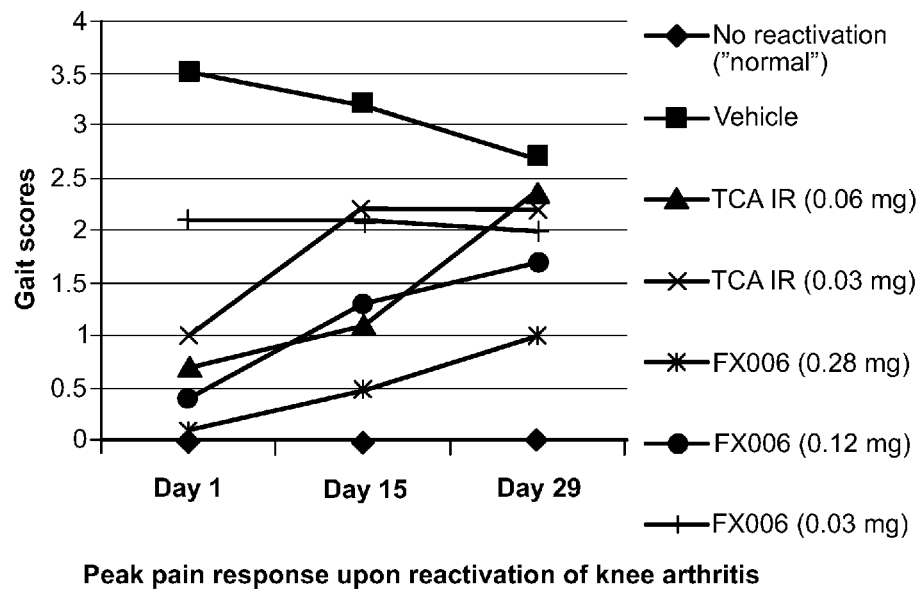
FIG. 45 is a graph depicting peak pain response following repeated reactivations of arthritis in the right knee. All treatments were administered as a single IA dose in the right knee on Day 0.
Figure 46:
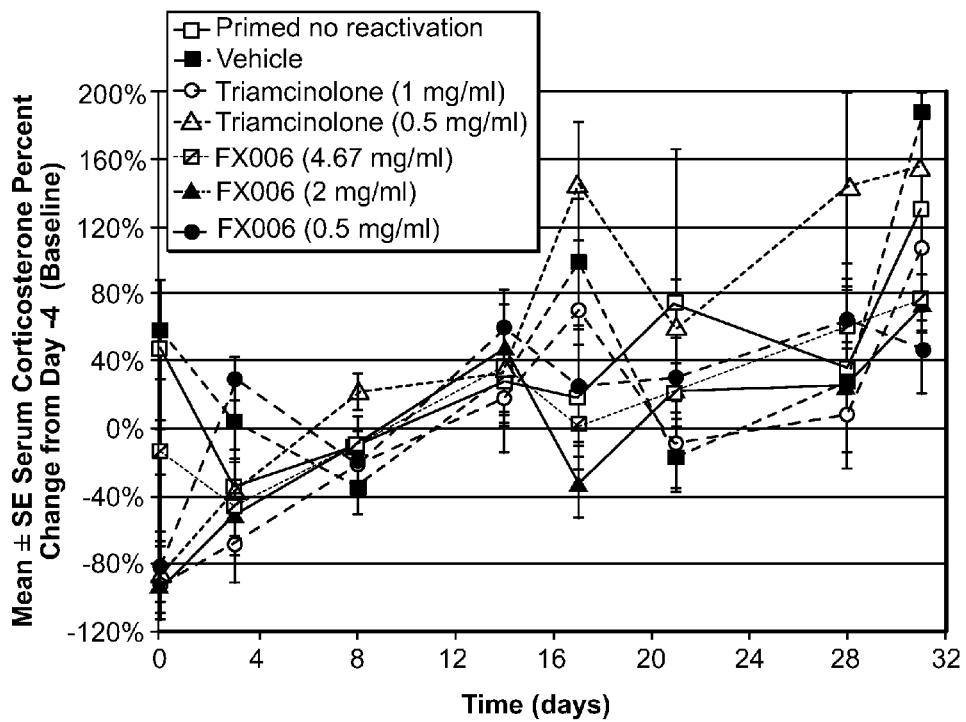
FIG. 46 is a graph depicting the time course of corticosterone recovery for various groups in the rat study in a model of osteoarthritis.

Overall, a clear dose-dependence of response was noted for both FX006 and TCA IR. Also, if less than 10% of this dose is available by the day after dosing (Day 1), it should be noted in FIG. 44B that the efficacy of FX006 at 0.28 mg (squares) is greater than TCA IR at 0.03 mg (triangles) at all evaluations. Further, the duration of efficacy of TCA (both FX006 and IR) appears to be a function of dose, however, the prolonged release of TCA from the PLGA microspheres in FX006 results in more sustained efficacy. This is more clearly depicted in another representation of the data in FIG. 45 in which peak response for each dose as determined by gait/pain scores on Day 1 following each reactivation (Days 1, 15 and 29) are plotted. FIG. 46 plots the time course of corticosterone recovery for all study groups. On balance, across all groups that received the corticosteroid, there was recovery.

Figure 47A:
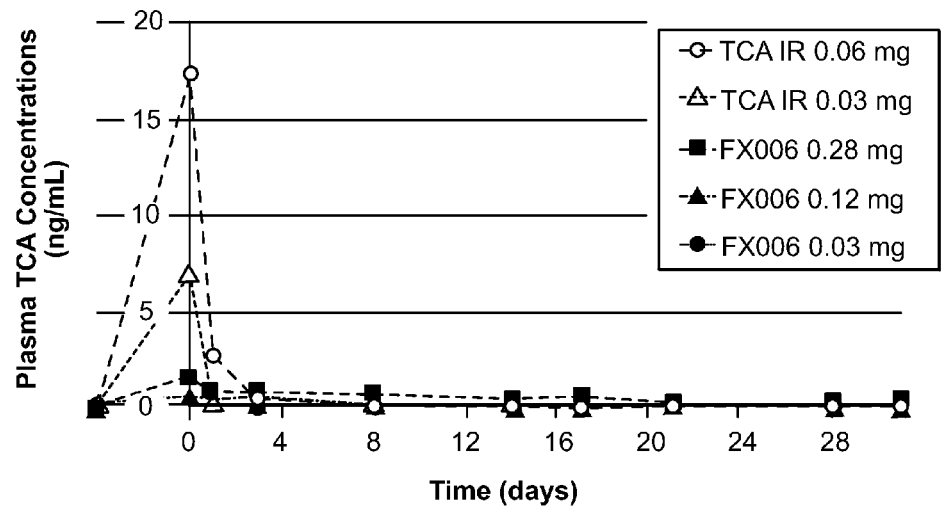
FIGS. 47A-47B are a series of graphs depicting the plasma TCA concentration-time data for various groups in the rat study in a model of osteoarthritis. Only the groups that received injections of TCA microparticles (FX006 groups) are shown in FIG. 47B on an expanded scale.
Figure 47B:
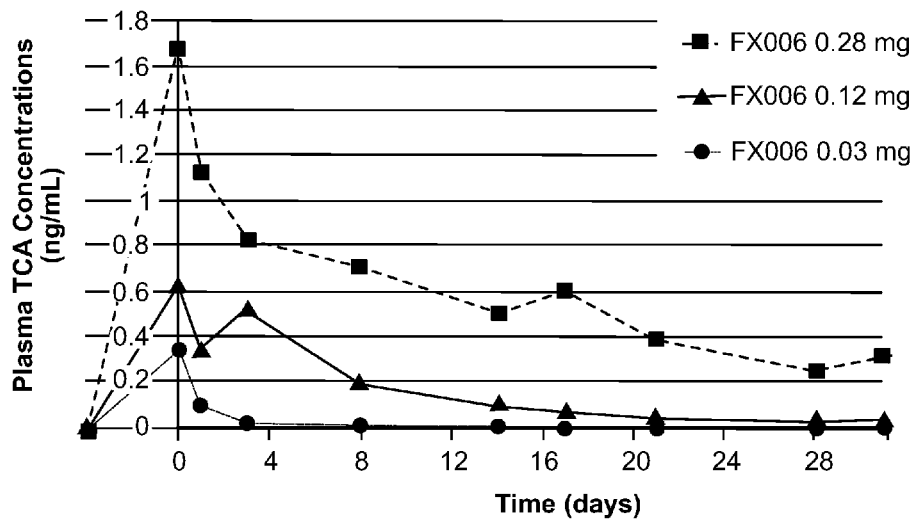

Plasma levels of TCA were measured in samples taken from all rats at baseline (Day −4), Days 0 (2 hr post dosing), 1, 3, 8, 14, 17, 21, 28, and 31. Concentration-time curves for all treatment groups are shown in FIG. 47A. FIG. 47B shows only the FX006 dose groups on a larger scale since maximal plasma concentrations with FX006 were far lower than those with TCA IR.

Figure 48:
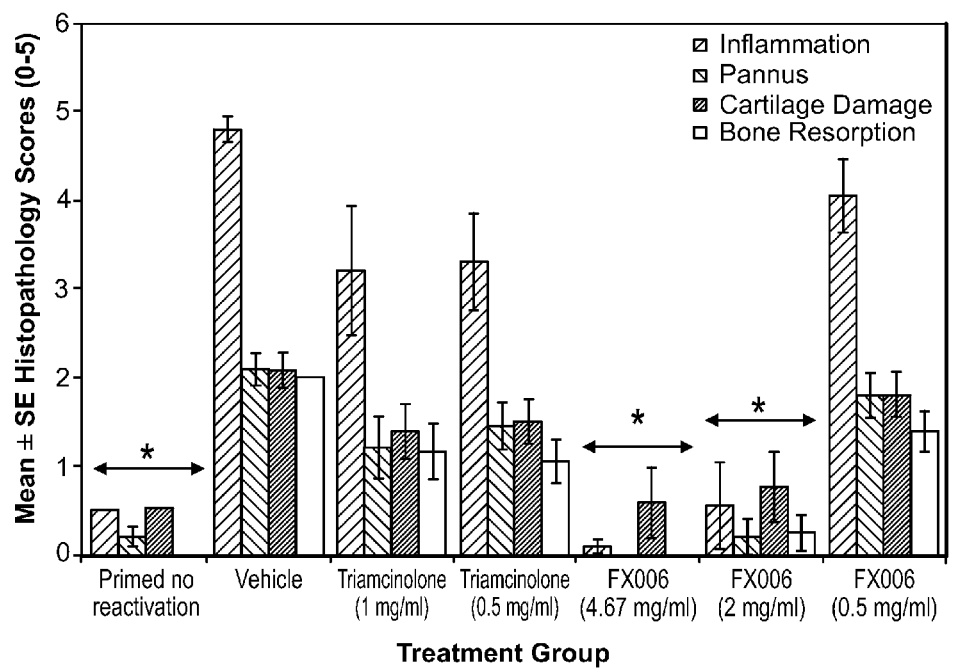
FIG. 48 is a graph depicting the end-of-study histopathology scores for various treatment groups in the rat study in a model of osteoarthritis.

Histopathological evaluation of the knees taken from all animals at the end of the study (Day 32 at the end of the $3^{rd}$ reactivation of arthritis) demonstrated statistically significant improvement by FX006 at the high and mid-range doses (0.28 and 0.12 mg) in the composite histological score and each component score (inflammation, pannus, cartilage damage and bone resorption) as shown in FIG. 48. As described above, the dose of 0.28 mg FX006 demonstrated strong efficacy (i.e. analgesic activity) throughout all 3 reactivations, whereas the dose of 0.12 mg was active but to a lesser degree through all 3 reactivations. At the doses of TCA IR used, the duration of efficacy was mostly through the first reactivation of arthritis, with partial efficacy of the higher (0.06 mg) dose in the second reactivation, and this also translated into a much smaller non-significant improvement in histological scores. Importantly, these data demonstrate that TCA has no deleterious effect on cartilage and as has been described in other settings, it actually reduces cartilage damage in an inflammatory milieu.

In conclusion, the prolonged residence of TCA in the joint upon IA dosing with FX006 resulted in extending the duration of efficacy in the rat PGPS model of arthritis with a significant histological improvement in inflammation, pannus formation, cartilage damage and bone resorption. FX006 had these effects without inhibiting HPA axis function as demonstrated by the return to baseline of corticosterone levels within 14 days after dosing. The clinical implications for the treatment of patients with osteoarthritis, rheumatoid arthritis and other inflammatory joint disorders are as follows:

Intra-articular injection of sustained release corticosteroid microparticle formulations provides prolonged pain relief relative to intra-articular injection of immediate release steroids.

Intra-articular injection of sustained release corticosteroid microparticle formulations is efficacious in reducing pain and inflammation at doses that do not inhibit the HPA axis.

The duration of efficacy of sustained release of intra-articular corticosteroid microparticle formulations is a function of dose.

Intra-articular injection of sustained release corticosteroid microparticle formulations slows, arrests, reverses, or otherwise inhibits structural damage to tissues caused by inflammation.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. Applicants reserve the right to pursue such inventions in later claims.

What is claimed is:

1. A method of manufacturing an injectable formulation comprising controlled- or sustained-release microparticles comprising triamcinolone acetonide (TCA) or a pharmaceutically-acceptable salt thereof and a poly(lactic-co-glycolic) acid copolymer (PLGA) matrix.; wherein the TCA comprises between 22% to 28% of the microparticle and wherein the PLGA has the following characteristics: (i) a molecular weight in the range or about 40 to 70 k Da; and (ii) a lactic acid: glycolic acid molar ratio of 80:20 to 60:40, the method comprising:
   (a) dispersing the TCA and the poly(laclic-co-glycolic) acid copolymer in an organic solution to produce a TCA-PLGA mixture, wherein the PLGA has a molecular weight in the range of about 40 to 70 kDa and a lactic acid: glycolic acid molar ratio of 80:20 to 60:40, and wherein the ratio of TCA to PLGA to organic solution in the TCA-PLGA mixture is 1:3:57;
   (b) atomizing the TCA-PLGA mixture into micro-droplets by adding the TCA-PLGA mixture to a spinning disk; and
   (c) treating the TCA-PLGA mixture to remove the solvent, thereby producing an injectable formulation comprising controlled- or sustained-release microparticle comprising TCA or a pharmaceutically-acceptable salt thereof and a PLGA matrix wherein the TCA comprises between 22% to 28% of the microparticles and wherein the PLGA has the following characteristics: (i) a molecular weight in the range or about 40 to 70 k Da; and (ii) a lactic acid: glycolic acid molar ratio of 80:20 to 60:40.

2. The method of claim 1, wherein step (c) comprises a solvent evaporation process to remove the solvent.

3. The method of claim 2, wherein the solvent evaporation process utilizes a drying chamber.

4. The method of claim 1, wherein the solvent is dichloromethane.

5. The method of claim 1 further comprising step (d) collecting the controlled- or sustained-release microparticles using a cyclone separator.

6. The method of claim 5 further comprising step (e) using a secondary drying step to remove residual solvents.

7. The method of claim 6 further comprising step (f) sieving the collected controlled- or sustained-release microparticles.

8. The method of clam 7, wherein step (f) uses a 150 μm sieve.

9. The method of claim 1, wherein the spinning disk rotates at a speed of approximately 3300 rpm inside temperature controlled chamber maintained at 38-45° C.

* * * * *